US012221439B2

(12) United States Patent
Mete et al.

(10) Patent No.: US 12,221,439 B2
(45) Date of Patent: Feb. 11, 2025

(54) TETRAHYDROPYRIDOPYRIMIDINE DERIVATIVES AS AhR MODULATORS

(71) Applicant: JAGUAHR THERAPEUTICS PTE LTD, Singapore (SG)

(72) Inventors: Antonio Mete, Leicestershire (GB); James Hitchin, Nottingham (GB); Mark Graham, Leicestershire (GB); John King-Underwood, Ledbury (GB); Philip Vellacott Thorne, Nottingham (GB)

(73) Assignee: JAGUAHR THERAPEUTICS PTE LTD, Singapore (SG)

( * ) Notice: Subject to any disclaimer, the term of this patent is extended or adjusted under 35 U.S.C. 154(b) by 846 days.

(21) Appl. No.: 17/270,626

(22) PCT Filed: Aug. 23, 2019

(86) PCT No.: PCT/EP2019/072641
§ 371 (c)(1),
(2) Date: Feb. 23, 2021

(87) PCT Pub. No.: WO2020/039093
PCT Pub. Date: Feb. 27, 2020

(65) Prior Publication Data
US 2021/0332041 A1 Oct. 28, 2021

(30) Foreign Application Priority Data
Aug. 24, 2018 (SG) .......................... 10201807244X

(51) Int. Cl.
C07D 471/04 (2006.01)
C07D 487/04 (2006.01)

(52) U.S. Cl.
CPC ......... *C07D 471/04* (2013.01); *C07D 487/04* (2013.01)

(58) Field of Classification Search
CPC .................................................. C07D 471/04
USPC ........................................................ 544/328
See application file for complete search history.

(56) References Cited

U.S. PATENT DOCUMENTS

| 2012/0136012 A1 | 5/2012 | Breslin et al. |
| 2023/0279000 A1 | 9/2023 | Graham et al. |

FOREIGN PATENT DOCUMENTS

| WO | 02/22607 A1 | 3/2002 |
| WO | 2005/014558 A1 | 2/2005 |
| WO | 2006/044762 A2 | 4/2006 |
| WO | 2010/059401 A2 | 5/2010 |
| WO | 2012/015914 A2 | 2/2012 |
| WO | 2016/154110 A1 | 9/2016 |
| WO | 2021/173082 A1 | 9/2021 |

OTHER PUBLICATIONS

Database Registry, "XP002795210", Chemical Abstracts Services, Database Accession No. 1331980-89-2, Compound with the Registry No. 1331980-89-2, 1 page, Sep. 13, 2011. (Year: 2011).*
Database Registry, "XP002795210", Chemical Abstracts Services, Database Accession No. 1331980-89-2, Compound with the Registry No. 1331980-89-2, 1 page, Sep. 13, 2011.
Database Registry, "XP002795211", Chemical Abstracts Services, Database Accession No. 1332109-12-2, Compound with the Registry Nos. 1332109-12-2 and 1332134-49-2, 2 pages, Sep. 14, 2011.
Database Registry, "XP002795212", Chemical Abstracts Services, Database Accession No. 1360232-40-1, Compound with the Registry Nos. 1360232-40-1, 1360253-78-6, 1360364-34-6, 1360407-66-4, 4 pages, Mar. 7, 2012.
Kuznetsov et al., "Synthesis of 2-Pyridyl-Substituted Derivatives of 7-Benzyl-5,6,7,8-Tetra-Hydropyrido[3,4-d]pyrimidine", Chemistry of Heterocyclic Compounds, vol. 43(10): 1320-1324, 2007.
Raheem et al., "Discovery of Tetrahydropyridopyrimidine Phosphodiesterase 10A Inhibitors for the Treatment of Schizophrenia", Bioorganic & Medicinal Chemistry Letters, vol. 22: 5903-5908, 2012.
Database Registry, 2012, "RN 1360407-66-4-Pyrido[3,4-d]pyrimidin-4-amine, 5,6,7,8-tetrahydro-N-[2-(1H-indol-3-yl)ethyl]-2-(2-pyridinyl)", "RN 1360388-65-3-5H-Pyrrolo[3,4-d]pyrimidin-4-amine, 6,7-dihydro-N-methyl-N-[(6-methyl-1H-benzimidazol-2-yl)methyl]-2-(3-pyridinyl)", "RN 1360364-34-6-Pyrido[3,4-d]pyrimidin-4-amine, 5,6,7,8-tetrahydro-N-[2-(1H-indol-3-yl)ethyl]-2-phenyl", "RN 1360253-78-6-5H-Pyrrolo[3,4-d]pyrimidin-4-amine, 6,7-dihydro-N-[2-(1H-indol-1-yl)ethyl]-N-methyl-2-(3-pyridinyl)", RN 1360232-40-1-5H-Pyrrolo[3,4-d]pyrimidin-4-amine, 6,7-dihydro-N-[2-(1H-.
Database Registry, 2011, "RN 1332207-45-0-Pyrido[3,4-d]pyrimidin-4-amine, 5,6,7,8-tetrahydro-N-[(6-methyl-1H-benzimidazol-2-yl)methyl]-2-(3-pyridinyl)", "RN 1332134-49-2-Pyrido[3,4-d]pyrimidin-4-amine, 5,6,7,8-tetrahydro-N-[2-(1H-indol-3-yl)ethyl]-2-(3-pyridinyl)", "RN 1332109-12-2-Pyrido[3,4-d]pyrimidin-4-amine, N-[2-(1H-benzimidazol-2-yl)ethyl]-5,6,7,8-tetrahydro-2-(3-pyridinyl)", "RN 1331980-89-2-Pyrido[3,4-d]pyrimidin-4-amine, N-[2-(1H-benzimidazol-2-yl)ethyl]-5,6,7,8-tetrahydro-2-(4-pyridinyl)", retrieved from STN international [online], 3 pages, retrieved on Jul. 11,.
Database Registry, 2012, "1394537-90-6-Pyrido[3,4-d]pyrimidin-4-amine, N-(2,1,3-benzoxadiazol-5-ylmethyl)-5,6,7,8-tetrahydro-2-(2-pyridinyl)", ChemBridge Corporation, XP055807788, 1 page, Sep. 18, 2012.
Database Registry, 2012, "RN 1378145-02-8-1(2H)-Phthalazione, 4-[[[6,7,8,9-tetrahydro-2-(2-pyridinyl)-5H-pyrimido[4,5-d]azepin-4-yl]amino]methyl]", ChemBridge Corporation, XP055807792, 1 page, Jun. 14, 2012.

(Continued)

*Primary Examiner* — Taofiq A Solola
(74) *Attorney, Agent, or Firm* — Prismatic Law Group, PLLC; Ronald J. Kamis

(57) ABSTRACT

The present disclosure relates to compounds of formula (I), which are suitable as AhR modulators, in particular AhR inhibitors. The disclosure also relates to compositions comprising said compounds and use of said compounds or compositions in treatment, in particular in the treatment of cancer. The disclosure further relates to methods of preparing said compounds.

20 Claims, No Drawings

(56) References Cited

OTHER PUBLICATIONS

Database Registry, 2012, "RN 1360407-66-4-Pyrido[3,4-d]pyrimidin-4-amine, 5,6,7,8-tetrahydro-N-[2-(1H-indol-3-yl)ethyl]-2-(2-pyridinyl)", ChemBridge Corporation, XP055807815, 1 page, Mar. 7, 2012.

Database Registry, 2012, "RN 1360388-65-3-5H-pyrrolo[3,4-d]pyrimidin-4-amine,6,7-dihydro-N-methyl-N-[(6-methyl-1H-benzimidazol-2-yl)methyl]-2-(3-pyridinyl)", "RN 1360364-34-6-Pyrido[3,4-d]pyrimidin-4-amine, 5,6,7,8-tetrahydro-N-[2-(1H-indol-3-yl)ethyl]-2-phenyl", "RN 1360289-84-4-5H-Pyrrolo[3,4-d]pyrimidin-4-amine, N-[(5-fluoro-1H-indol-2-yl)methyl]-6,7-dihydro-N-methyl-2-(4-pyridinyl)", "RN 1360264-95-4-5H-Pyrrolo[3,4-d]pyrimidin-4-amine, 2-cyclopentyl-6,7-dihydro-N-(pyrazolo[1,5-a]pyridin-3-ylmethyl)", RN 1360253-78-6-5H-Pyrrolo[3,4-d].

Database Registry, 2011, "1347555-34-3-Ethanone, 1-[4-[(5-fluro-1H-indzol-3-yl)amino]-5,8-dihydro-2-[2-(trifluoromethyl)phenyl]pyrido[3,4-d]pyrimidin-7(6H)-yl]", "RN 1347480-87-8-Pyrido[4,3-d]pyrimidin-4-amine, 2-(2-chlorophenyl)-N-(5-fluoro-1H-indazol-3-yl)-5,6,7,8-tetrahydro", GVK Bio, XP055807845, 1 page, Dec. 2, 2011.

\* cited by examiner

TETRAHYDROPYRIDOPYRIMIDINE DERIVATIVES AS AhR MODULATORS

CROSS-REFERENCE TO RELATED APPLICATIONS

This application is a 371 National Phase of International Patent Application No. PCT/EP2019/072641 filed on Aug. 23, 2019, which claims priority to Singapore Patent Application SG 10201807244X filed on Aug. 24, 2018, the content of each of which applications is incorporated herein by reference.

The present invention covers compounds of the general formula (I) as described and defined herein, methods for preparing said compounds, pharmaceutical compositions and combinations comprising said compounds and the use of said compounds and pharmaceutical compositions for the treatment or prevention of diseases, in particular cancer or conditions with dysregulated immune functions, or other conditions associated with aberrant AHR signalling, as a sole agent or in combination with other active ingredients. Such compounds may also be of utility in the expansion of hematopoietic stem cells (HSCs) and the use of HSCs in autologous or allogenic transplantation for the treatment of patients with inherited immunological and autoimmune diseases and diverse hematopoietic disorders.

BACKGROUND

The aryl hydrocarbon receptor (AhR) is a ligand-activated factor that belongs to the family of the basic helix-loop-helix-Per/ARNT/Sim family. Following ligand binding in the cytoplasm, AhR dissociates from its complex with Hsp90 and the AhR-interacting protein, XAP2, allowing ligated AhR to translocate to the nucleus. There, AhR dimerizes with the AhR nuclear translocator (ARNT), that then binds to xenobiotic response elements (XREs) promoting the up- or down-regulation of a multitude of target genes in many different tissues. The AhR is best known for binding to environmental toxins and inducing various members of the cytochrome P450 family including CYP1A1, CYP1A2 and CYP1B1 required for their elimination. Activation of AhR by xenobiotics has demonstrated that this receptor plays a role in a range of physiological processes including embryogenesis, tumourigenesis and inflammation (Esser & Rannug, Pharmacol Rev, 2015, 67:259; Roman et al., Pharmacol Ther, 2018, 185:50).

AhR is expressed in many immune cell types including dendritic cells, macrophages, T cells, NK cells and B cells and plays an important role in immunoregulation (Quintana & Sherr, Pharmacol Rev, 2013, 65:1148; Nguyen et al., Front Immunol, 2014, 5:551). The toxic/adverse effects of classical exogenous AhR agonists, such as 2,3,7,8-Tetrachlorodibenzo-p-dioxin (TCDD) are well known and include profound immunosuppression and initiation of malignancy (Esser et al., Trends Immunol, 2009, 30:447; Feng et al., Biochimica et Biophysica Acta, 2013, 1836: 197). Physiological effects of AhR agonists on immune cells include promotion of regulatory T cell (Treg) generation (Pot, Swiss Med Wkly, 2012, 142:w13592) and modulation of Th17 cell differentiation and activation (Baricza et al., Cell Mol Life Sci, 2016, 73:95). AhR also modulates the function of antigen presenting cells, such as dendritic cells and macrophages. AhR activation decreases the expression of class II major histocompatibility complex and co-stimulatory molecules and also the production of Th1 and Th17 polarizing cytokines by dendritic cells (Mezrich et al., J Immunol, 2010, 185:3190; Nguyen et al., Proc Natl Acad Sci USA, 2010, 107:19961; Quintana et al., 2010 Proc Natl Acad Sci USA, 107:20768). Indeed, AhR activation boosts the ability of DCs to promote the differentiation of Tregs (Jurado-Manzano et al., 2017, Immunol Lett, 190:84).

In addition to xenobiotics, the AhR can also bind metabolic products of tryptophan degradation including kynurenine (KYN) and kynurenic acid (KYNA). Indoleamine 2,3 dioxygenase 1 and 2 (IDO1/IDO2) and tryptophan 2,3-dioxygenase 2 (TDO2) catalyse the commitment step of the KYN metabolic pathway and are expressed in immune cells (IDO1) and a range of cancer cells (IDO1 and TDO2)(Pilotte et al., Proc Nat Acad Sci, 2012, 109:2497). Inhibitors of IDO1 have attracted much interest as potential new treatments to stimulate the immune system to recognize and eliminate cancer cells (Cheong & Sun, Trends Pharmacol Sci, 2018, 39:307). Traditionally the immunosuppressive effect of IDO1 has been attributed mainly to reduced levels of tryptophan, which activates the kinase GCN2 (general control non-derepressible 2) and inhibits T cell proliferation/activation both in tumour draining lymph nodes lymph nodes and in the tumour micro-environment. More recently it has become apparent that some of the efficacy of IDO inhibitors may be the result of decreased production of AhR agonists. These endogenously generated AhR agonists have been shown to elicit a range of effects on immune cells including upregulation of IDO1 in dendritic cells (Julliard et al., Front Immunol, 2014, 5:458), inhibition of human T cell proliferation (Frumento et al., J Exp Med, 2002; 196:459; Terness et al., J Exp Med, 2002; 196: 447; Opitz et al., Nature, 2011, 478:197) and up-regulation of PD-1 expression in cytotoxic T lymphocytes (Liu et al., Cancer Cell, 2018; 33:480). As highlighted above, IDO1 is not the only source of endogenous AhR agonists. TDO2 is predominately expressed in the liver but it is also constitutively expressed in some cancers, notably malignant glioma, hepatocellular carcinoma, melanoma, bladder, breast, lung and colorectal cancer (Opitz et al., Nature, 2011, 478:197; Pilotte et al., Proc Nat Acad Sci, 2012, 109:2497; D'Amato et al., Cancer Res, 2015, 75(21):4651; Hsu et al., Oncotarget, 2016, 7(19): 27584; Chen et al., Dis Markers, 2016, 2016:8169724). Such data suggests that AhR antagonists may have broader efficacy than selective IDO-1 inhibitors, as they will attenuate endogenous AhR agonist signalling regardless of its source.

In addition to their effects on immune cells, such endogenous agonists have also been implicated in cancer progression via direct effects on the tumour. For example, KYN increases human glioblastoma cell survival and migration (Opitz et al., Nature, 2011, 478:197). Several other studies also implicate the AhR in cancer progression in the absence of environmental ligands. The AhR-repressor (AHRR) protein acts as a tumour suppressor gene in several human cancers (Zudaire et al., J Clin Invest, 2008, 118:640). AhR expression and "constitutive" (endogenous ligand-driven) activity in breast cancer cells correlate with tumour aggressiveness (Schlezinger et al., Biol Chem, 2006, 387:1175; Yang et al., J Cell Biochem, 2008, 104:402) and control expression of genes associated with tumour invasion (Yang et al., Oncogene, 2005, 24:7869). Ectopic AhR expression in non-malignant human mammary epithelial cells induces an epithelial-to-mesenchymal transition and a >50% increase in cell growth rates (Brooks & Eltom, Curr Cancer Drug Targets, 2011, 11:654) and AhR knockdown induced gene changes in human breast cancer cell lines consistent with a mesenchymal to epithelial cell reversion to a less aggressive phenotype (Narasimhan et al., Int J Mol Sci, 2018, 19:1388).

AhR antagonists or AhR knockdown has been shown to reduce proliferation, survival, invasiveness and migration of human breast cancer cells in culture (Parks et al., Mol Pharmacol, 2014, 86:593; D'Amato et al., Cancer Res, 2015, 75(21):4651; Narasimhan et al., Int J Mol Sci, 2018, 19:1388) and to reduce survival of glioblastoma cells (Gramatzki et al., Oncogene, 2009, 28:2593; Opitz et al., Nature, 2011, 478:197; Guastella et al., J Neuro-oncol, 2018, in press). Finally, AhR antagonists block the formation of tumourspheres (Stanford et al., Mol Cancer Res, 2016, 14:696) which are formed by cancer stem cells (CSCs), a subset of tumour cells that drive the initiation, progression and metastasis of tumours.

Thus, AhR agonists released from immune cells and from tumour cells act in an autocrine and paracrine fashion to promote tumour growth. Agents that reduce or block these effects may therefore find utility in the treatment of cancer and/or conditions with dysregulated immune functions.

WO2017/202816 relates to compounds and compositions for the treatment or prophylaxis of cancer or conditions with dysregulated immune responses or other disorders associated with aberrant AhR signalling. In particular, WO2017/202816 relates inter alia to heterocyclic compounds capable of inhibiting AhR function.

WO2010/059401 relates to compounds and compositions for expanding the number of CD34+ cells for transplantation. In particular, WO 2010/059401 relates inter alia to heterocyclic compounds capable of down-regulating the activity and/or expression of AhR.

WO2012/015914 relates to compositions and methods for modulating AhR activity. In particular, WO2012/015914 relates inter alia to heterocyclic compounds that modulate AhR activity for use in therapeutic compositions to inhibit cancer cell proliferation and tumour cell invasion and metastasis.

SUMMARY OF THE DISCLOSURE

The present disclosure provides pyrimidine compounds of general formula (I) which inhibit the AhR. The disclosure is summarised in the following paragraphs:
1. A compound of formula (I)

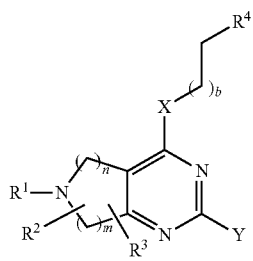

wherein:
Y is a 5 or 6 membered ring optionally comprising 1, 2, or 3 heteroatoms selected from N, O and S, substituted with $R^5$ and $R^6$;
$R^1$ is H, $C_{1-3}$ alkyl, ($-CH_2$)pCN, $-COC_{1-3}$ alkyl, $-CO(CH_2)qNR^7R^8$, $-SO_2C_{1-3}$ alkyl, $-SO_2NR^7R^8$, $-(CH_2)qPh$, $-C(O)Z$;
$R^2$ is H or $C_{1-3}$ alkyl;
$R^3$ is H or $C_{1-3}$ alkyl;
$R^4$ is a 9 or 10 membered heteroaryl with at least one heteroatom selected from N, O or S (such as Indol-3-yl or Benzimidazol-2-yl), with substituents $R^9$ and $R^{10}$;
$R^5$ is H, hydroxy, halogen (such as F, Cl), CN, $C_{1-3}$ alkyl, $-CO(CH_2)qNR^7R^8$, $-SO_2C_{1-3}$ alkyl, $-SO_2NR^7R^8$,
$R^6$ is H, hydroxy, halogen (such as F, Cl), CN, $C_{1-3}$ alkyl, $-CO(CH_2)qNR^7R^8$, $-SO_2C_{1-3}$ alkyl, $-SO_2NR^7R^8$,
$R^7$ is H or $C_{1-3}$ alkyl, such as $-CH_3$;
$R^8$ is H or $C_{1-3}$ alkyl, such as $-CH_3$;
$R^9$ is H, hydroxy, halogen (such as F, Cl), CN or a $C_{1-3}$ alkyl group, $-CO(CH_2)q NR^7R^8$, $-SO_2C_{1-3}$ alkyl, $-SO_2NR^7R^8$,
$R^{10}$ is H, hydroxy, halogen (such as F, Cl), CN, $C_{1-3}$ alkyl, $-CO(CH_2)q NR^7R^8$, $-SO_2C_{1-3}$ alkyl, $-SO_2NR^7R^8$,
$R^{11}$ is H or $C_{1-3}$ alkyl (such as $-CH_3$);
X is $NR^{11}$ or O;
Z is a 5 or 6 membered heteroaryl with at least one heteroatom selected from N, O and S, for example 1 or 2 nitrogens, wherein said heteroaryl optionally bears one or two substituents selected from hydroxy, halogen (such as F, Cl), CN, $C_{1-3}$ alkyl;
b is an integer 1 or 2 (for example 1);
n is an integer 1 or 2;
m is an integer 1 or 2;
p is an integer 1, 2 or 3 (such as 1);
q is 0, 1, 2 or 3 (such as 0 or 1),
or a pharmaceutically acceptable salt thereof.
2. A compound of formula (II)

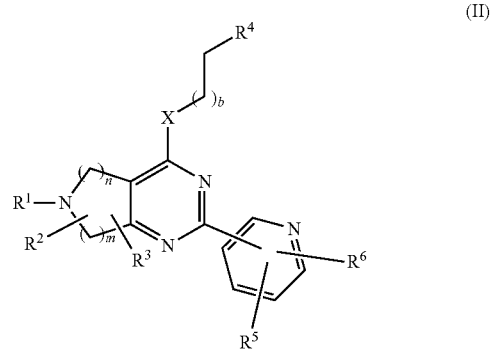

wherein X, $R^1$, $R^2$, $R^3$, $R^4$, $R^5$, $R^6$, b, m and n are defined above for compounds of formula (I) or a pharmaceutically acceptable salt thereof.
3. A compound of formula (III):

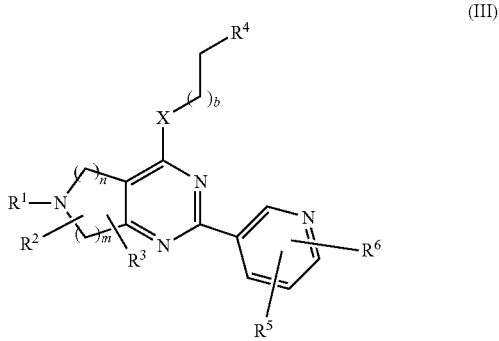

wherein X, R¹, R², R³, R⁴, R⁵, R⁶, b, m and n are defined above for compounds of formula (I) or a pharmaceutically acceptable salt thereof.

4. A compound according to any one of paragraphs 1 to 3 wherein n is 2.

5. A compound according to any one of paragraphs 1 to 3, wherein n is 1.

6. A compound according to any one of paragraphs 1 to 5, wherein m is 2.

7. A compound according to any one of paragraphs 1 to 5, wherein m is 1.

8. A compound according to any one of paragraphs 1 to 3, of formula (IV):

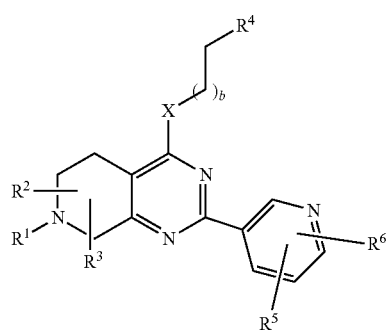

(IV)

wherein X, R¹, R², R³, R⁴, R⁵, R⁶ and b, are defined above for compounds of formula (I) or a pharmaceutically acceptable salt thereof.

9. A compound according to any one of paragraphs 1 to 3, of formula (V):

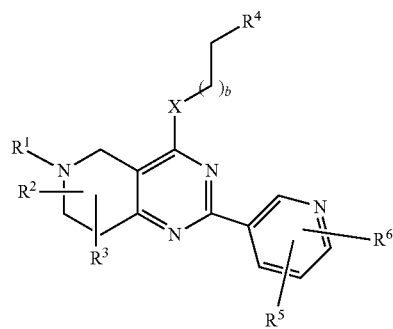

(V)

wherein X, R¹, R², R³, R⁴, R⁵, R⁶ and b, are defined above for compounds of formula (I) or a pharmaceutically acceptable salt thereof.

10. A compound according to any one of paragraphs 1 to 3, of formula (V):

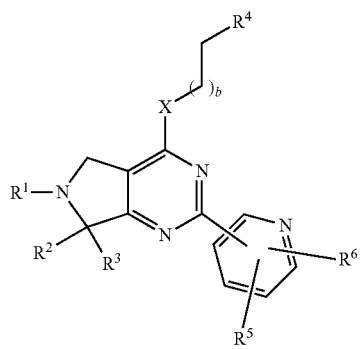

(VI)

wherein X, R¹, R², R³, R⁴, R⁵, R⁶ and b, are defined above for compounds of formula (I) or a pharmaceutically acceptable salt thereof.

11. A compound according to any one of paragraphs 1 to 3, of formula (VII):

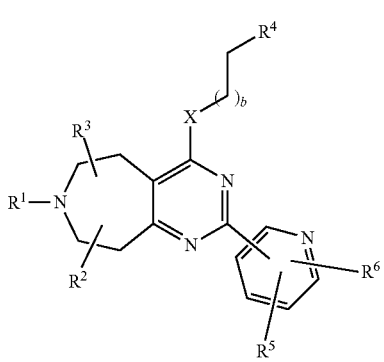

(VII)

wherein X, R¹, R², R³, R⁴, R⁵, R⁶ and b, are defined above for compounds of formula (I) or a pharmaceutically acceptable salt thereof.

12. A compound according to any one of paragraphs 1 to 11, wherein R¹ is independently selected from H, CH₃, —CH₂CH₃, —CH₂CH₂CH₃, —CH(CH₃)₂, —C(O)CH₃, C(O)NH₂, —C(O)NHCH₃. —C(O)N(CH₃)₂, —CH₂CN, —SO₂NH₂, —SO₂CH₃, —SO₂N(CH₃)₂, —CH₂Ph, —C(O)1-Me-Pyrazol-5-yl.

13. A compound according to any one of paragraphs 1 to 11, wherein R¹ is independently selected from H, CH₃, —CH₂CH₃, —CH₂CH₂CH₃, —CH(CH₃)₂, —C(O)NH₂, —C(O)NHCH₃. —C(O)N(CH₃)₂, —CH₂CN, —SO₂NH₂, —SO₂CH₃, —SO₂N(CH₃)₂, —CH₂Ph, —C(O)1-Me-Pyrazol-5-yl.

14. A compound according to paragraph 14, wherein R¹ is selected from H, —CH₂CN, —SO₂CH₃, and —SO₂N(CH₃)₂, —C(O)N(CH₃)₂.

15. A compound according to paragraphs 13 or 14, wherein the R¹ is H.

16. A compound according to any one of paragraphs 1 to 11, wherein R¹ is $C_{1-3}$ alkyl.

17. A compound according to any one of paragraphs 1 to 16, wherein R² is H or —CH₃.

18. A compound according to claim 17, wherein R² is H.

19. A compound according to any one of paragraphs 1 to 18, wherein $R^3$ is H or —$CH_3$.
20. A compound according to paragraph 19, wherein $R^3$ is H.
21. A compound according to any one of paragraphs 1 to 18, wherein $R^4$ is selected from indolyl (such as indol-3-yl, in particular 5-fluoro-1H-indol-3-yl) and benzimidazolyl (such as benzimidazole-2-yl), each independently bearing $R^9$ and $R^{10}$.
22. A compound according to any one of paragraphs 1 to 21, wherein $R^5$ is selected from H, F, Cl, CN and —$CH_3$.
23. A compound according to paragraph 22, wherein $R^5$ is H.
24. A compound according to paragraph 22, wherein $R^5$ is F.
25. A compound according to any one of paragraphs 1 to 24, wherein $R^6$ is H, F, Cl, CN or —$CH_3$.
26. A compound according to paragraph 25, wherein $R^6$ is H.
27. A compound according to any one of paragraphs 1 to 26, wherein $R^7$ is selected from H and —$CH_3$;
28. A compound according to paragraph 27, wherein $R^7$ is —$CH_3$.
29. A compound according to paragraph 27, wherein $R^7$ is H.
30. A compound according to any one of paragraphs 1 to 29, wherein $R^8$ is selected from H and —$CH_3$.
31. A compound according to paragraph 30, wherein $R^8$ is H.
32. A compound according to paragraph 30, wherein $R^8$ is —$CH_3$.
33. A compound according to any one of paragraphs 1 to 32, wherein $R^9$ is H or F.
34. A compound according to paragraph 33, wherein $R^9$ is H.
35. A compound according to paragraph 33, wherein $R^9$ is F.
36. A compound according to any one of paragraph 1 to 35, wherein $R^{10}$ is H.
37. A compound according to any one of paragraphs 1 to 36, wherein $R^{11}$ is H.
38. A compound according to any one of paragraphs 1 to 37, wherein b is 1.
39. A compound according to any one of paragraphs 1 to 38, wherein p is 1.
40. A compound according to any one of paragraphs 1 to 39, wherein q is 1.
41. A compound according to any one of paragraphs 1 to 39, wherein q is 0.
42. A pharmaceutical composition comprising a compound according to any one of paragraphs 1 to 41 and an excipient, diluent or carrier.
43. A compound according to any one of paragraphs 1 to 41 or a pharmaceutical composition according to paragraph 42, for use in treatment.
44. A compound or composition for use according to paragraph 43, for use in the treatment of cancer.
45. A method of treating a patient comprising administering a therapeutically effective amount of a compound as defined in any one of paragraphs 1 to 41 or a composition as defined in paragraph 42.
46. Use of a compound according to any one of paragraphs 1 to 41 or a composition according to paragraph 42, for the manufacture of a medicament for the treatment of cancer.

In one embodiment m is 1 and n is 1. In one embodiment m is 1 and n is 2. In one embodiment m is 2 and n is 1. In one embodiment m is 2 and n is 2.

In one embodiment Y is pyrimidine, including pyrimidine substituted by $R^5$ and $R^6$.

In one embodiment Z is unsubstituted.

In particular, the compounds of the present invention have surprisingly been found to effectively inhibit AhR. Said compounds are useful for the treatment or prophylaxis of conditions where exogenous and endogenous AhR ligands induce dysregulated immune responses, for example: uncontrolled cell growth, proliferation and/or survival of tumour cells, immunosuppression. This dysregulation may be observed in the context of cancer, inappropriate cellular immune responses, and inappropriate cellular inflammatory responses.

In one embodiment the compounds of the present disclosure are useful in the treatment of cancer for example, liquid and/or solid tumours, and/or metastases thereof. Examples of cancers include head and neck cancer (such as brain tumours and brain metastases), cancer of the thorax including non-small cell and small cell lung cancer, gastrointestinal cancer (including stomach, oesophageal, colon, and colorectal), biliary tract cancer, pancreatic cancer, liver cancer, endocrine cancer, breast cancer, ovarian cancer, bladder cancer, kidney cancer, prostate cancer, bone cancer and skin cancer.

In one embodiment the cancer is an epithelial cancer. In one embodiment the cancer is a sarcoma. In one embodiment the cancer is a metastatic.

DETAILED DISCLOSURE

A 5 or 6 membered ring as optionally comprising 1, 2 or 3 heteroatoms selected from nitrogen, oxygen and sulfur, refers to a saturated, partially saturated or aromatic ring containing 5 or 6 atoms, including wherein all the atoms are carbon or where there are 1, 2 or 3 heteroatoms independently selected from nitrogen, oxygen and sulfur, for example cyclopentadiene, phenyl, thiophene, furan, pyrrole, pyrazole, imidazole, oxazole, thiazole, isothiazole, triazole, pyridine, pyrazine, triazine, thiazine, oxazine, cyclopentane, cyclohexane, pyrrolidine, pyrroline, pyrazolidine, imidazoline, tetrahydrofuran, tetrahydrothiophene, piperidine, piperazine, tetrahydrapyran, thiane, thiopyran, morpholine, or thiomorpholine.

In one embodiment the ring is 5 membered.

In one embodiment the ring is 6 membered.

In one embodiment the 5 or 6 membered ring is unsaturated or aromatic.

In one embodiment the 5 or 6 membered ring is selected from cyclopentadiene, phenyl, pyridine and pyrazine, such as phenyl and pyridine.

$C_{1-3}$ alkyl as employed herein refers to straight or branched chain alkyl, for example methyl, ethyl, propyl or isopropyl.

Halogen as employed herein includes fluoro, chloro, bromo or iodo.

CO represents carbonyl.

9 or 10 membered heteroaryl as employed herein refers to a bicyclic ring system containing 9 or 10 atoms, wherein at least one ring is aromatic and at least one ring contains a heteroatom, for example containing 1, 2, 3, or 4 heteroatoms independently selected from nitrogen, oxygen and sulfur, such as indoline, indole, isoindole, indolizine, indazole, benzimidazole, azaindole, pyrazolopyrimidine, purine, benzofuran, isobenzofuran, benzothiophene, benzoisooxazole, benzoisothiazole, benzoxazole, benzothiadiazole, adenine, guanine, tetrahydroquinoline, dihydroisoquinoline, quinoline, isoquinoline, quinolizine, quinoxaline, phthalazine, cinnoline, napthrhyridine, pyridopyrimidine, pyridopyrazine, pyridopyrazine, pteridine, chromene, isochromene, chromenone, benzoxazine, quinolinone, and isoquinolinone.

In one embodiment the 9 or 10 membered heteroaryl is selected from indolylyl and benzimidazolyl, such as indol-3-yl or benzimidazole-2-yl.

5 or 6 membered heteroaryl as employed herein is a ring containing 5 or 6 atoms wherein at least one atom is a heteroatom, for example selected from nitrogen, oxygen or sulphur, such as pyrrole, pyrazole, imidazole, thiophene, oxazole, isothiazole, thiazole, pyridine, pyridazine, pyrimidine, pyrazine, triazine, thiopyran, oxazine and thiazine, such as pyrrole, pyrazole and pyridine and pyrimidine.

The compounds of the present disclosure can be prepared by methods described herein.

GENERIC ROUTE 1 can be employed to make certain compounds of the present disclosure:

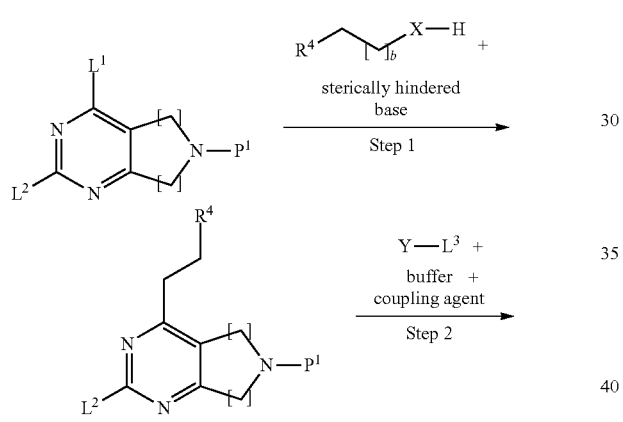

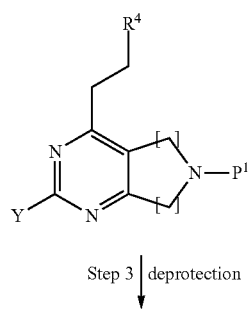

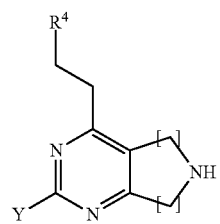

wherein
$L^1$ and $L^2$ are leaving groups, for example halogen, such as chloro;
$L^3$ is a leaving group, for example boronic acid;
$P^1$ is a protecting group, for example Boc; and
$R^4$ and Y are defined above for compounds of formula (I).

GENERIC ROUTE 2 can be employed to make certain compounds of the present disclosure:

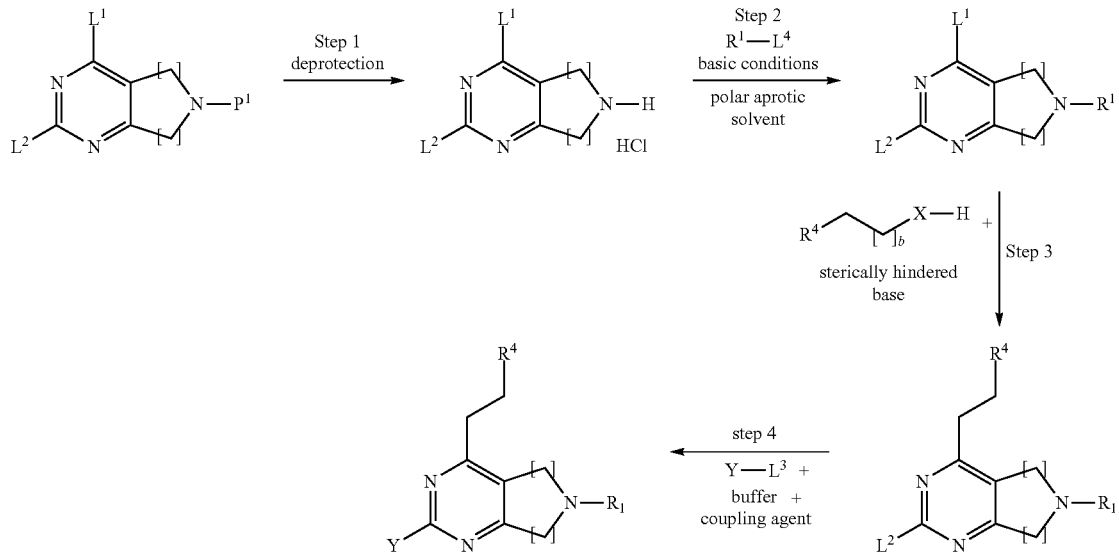

$L^1$ and $L^2$ are leaving groups, for example halogen, such as chloro;

$L^3$ is a leaving group, for example boronic acid;

$L^4$ is a leaving groups, for example halogen, such as bromo;

$P^1$ is a protecting group, for example Boc; and $R^1$, $R^4$ and Y are defined above for compounds of formula (I).

An example of a sterically hindered base is triethylamine, which may be employed in step 1 of scheme 1 and step 3 of scheme 2 with tryptamine.

A suitable buffer in step 2 of scheme 1 is aryl boronic acid and potassium carbonate, for example in a solvent, such as dioxan and water.

Coupling agents may require performing the reaction under nitrogen. Suitable coupling agents in for step 2 of scheme 1 and step 4 of scheme 2 include bis(diphenylphosphino)ferrocene]dichloropalladium (II) dichlorine.

Deprotection in step 3 of scheme 1 and step 1 of scheme 2 may be effected using, for example TFA, in particular in dichloromethane.

Step 2 of scheme 2 may be performed in the presence of a sterically hindered organic base, such as a triethylamine. A suitable polar aprotic solvent for the reaction is dichloromethane.

Protecting groups may be required to protect chemically sensitive groups during one or more of the reactions described above, to ensure that the process is efficient. Thus, if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; $4^{th}$ Rev Ed., 2006, ISBN-10: 0471697540.

Examples of salts of compound of the present disclosure include all pharmaceutically acceptable salts, such as, without limitation, acid addition salts of strong mineral acids such as HCl and HBr salts and addition salts of strong organic acids, such as a methansulfonic acid salt.

The present disclosure extends to solvates of the compounds disclosed herein. Examples of solvates include hydrates.

Novel intermediates are an aspect of the invention.

A further aspect of the present disclosure is methods of making the compounds disclosed herein.

Also provided herein a pharmaceutically composition comprising a compound according to the present disclosure and an excipient, diluent or carrier. A thorough discussion of pharmaceutically acceptable carriers is available in Remington's Pharmaceutical Sciences (Mack Publishing Company, N.J. 1991).

The pharmaceutical compositions of this disclosure may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

In one embodiment the therapeutic compositions may be prepared as injectables, either as liquid solutions or suspensions. Solid forms suitable for solution in, or suspension in, liquid vehicles prior to injection may also be prepared. Suitable liquids for reconstitution of such solid forms (including lyophilised solids) may be selected from aqueous solutions, for example saline, dextrose or water for injection and the like. In one embodiment the reconstituted liquid formulation is isotonic.

In one embodiment the pharmaceutical composition according to the present disclosure is provided as a tablet or a capsule for oral administration.

Treatment

The present disclosure also extends to methods of treating a patient comprising administering a therapeutically effective amount of a compound of the present disclosure (or a pharmaceutical composition comprising the same), for example for the treatment of cancer.

Also provide is a compound according to the present disclosure (or a pharmaceutical composition comprising the same) for use in treatment, for example for use in the treatment of cancer.

In a further aspect there is provided a compound of the present disclosure (or a pharmaceutical composition comprising the same) for use in the manufacture of a medicament for the treatment of cancer.

In one embodiment the cancer is an epithelial cancer, for example selected from example is selected from liver cancer (such as hepatocellular carcinoma), biliary tract cancer, breast cancer (such as none ER+ breast cancer), prostate cancer, colorectal cancer, ovarian cancer, cervical cancer, lung cancer, gastric cancer, pancreatic, bone cancer, bladder cancer, head and neck cancer, thyroid cancer, skin cancer, renal cancer, and oesophagus cancer, for example gastric cancer.

In one embodiment the cancer is selected from selected from the group comprising hepatocellular carcinoma, cholangiocarcinoma, breast cancer, prostate cancer, colorecetal cancer, ovarian cancer, lung cancer, gastric cancer, pancreatic and oesophagus cancer.

In one embodiment the biliary duct cancer is in a location selected from intrahepatic bile ducts, left hepatic duct, right hepatic duct, common hepatic duct, cystic duct, common bile duct, Ampulla of Vater and combinations thereof.

In one embodiment the biliary duct cancer is in an intrahepatic bile duct. In one embodiment the biliary duct cancer is in a left hepatic duct. In one embodiment the biliary duct cancer is in a right hepatic duct. In one embodiment the biliary duct cancer is in a common hepatic duct. In one embodiment the biliary duct cancer is in a cystic duct. In one embodiment the biliary duct cancer is in a common bile duct. In one embodiment the biliary duct cancer is in an Ampulla of Vater. In one embodiment the epithelial cancer is a carcinoma.

In one embodiment the treatment according to the disclosure is adjuvant therapy, for example after surgery.

In one embodiment the therapy according to the disclosure is neoadjuvant treatment, for example to shrink a tumour before surgery.

In one embodiment the tumour is a solid tumour. In one embodiment the cancer is a primary cancer, secondary cancer, metastasis or combination thereof. In one embodiment the treatment according to the present disclosure is suitable for the treatment of secondary tumours.

In one embodiment the cancer is metastatic cancer. In one embodiment the treatment according to the present disclosure is suitable for the treatment of primary cancer and metastases. In one embodiment the treatment according to the present disclosure is suitable for the treatment of secondary cancer and metastases. In one embodiment the treatment according to the present disclosure is suitable for the treatment of primary cancer, secondary cancer and metastases.

In one embodiment the treatment according to the present disclosure is suitable for the treatment of cancerous cells in a lymph node.

In one embodiment the liver cancer is primary liver cancer. In one embodiment the liver cancer is secondary liver cancer. In one embodiment the liver cancer is stage 1, 2, 3A, 3B, 3C, 4A or 4B.

In one embodiment the gastric cancer is stage 0, I, II, III or IV.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 1000 mg/kg, for example 0.1 mg/kg to 500 mg/kg. Pharmaceutical compositions may be conveniently presented in unit dose forms containing a predetermined amount of an active agent of the invention per dose.

Combination Therapy

In one embodiment the compound of the present disclosure is employed in combination therapy, for example wherein the further therapy is an anticancer therapy.

In one embodiment the anticancer therapy is a chemotherapy.

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, parp inhibitors and other antitumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent selected from nitrogen mustards, nitrosoureas, tetrazines, aziridines, platins and derivatives, and non-classical alkylating agents.

Platinum containing chemotherapeutic agent (also referred to as platins) includes, for example cisplatin, carboplatin, oxaliplatin, satraplatin, picoplatin, nedaplatin, triplatin and lipoplatin (a liposomal version of cisplatin), in particular cisplatin, carboplatin and oxaliplatin.

The dose for cisplatin ranges from about 20 to about 270 mg/m² depending on the exact cancer. Often the dose is in the range about 70 to about 100 mg/m².

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathipurine, mercap-topurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed(tomudex) hydrochloride, cladribine and 6-azauracil.

Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin (currently used only to treat bladder cancer) and mitoxantrone an anthracycline analog, in particular doxorubicin.

Examples of anti-microtubule agents, which may be employed in the method of the present disclosure, include vinca alkaloids and taxanes.

Vinca alkaloids include completely natural chemicals, for example vincristine and vinblastine and also semi-synthetic vinca alkaloids, for example vinorelbine, vindesine, and vinflunine Taxanes include paclitaxel, docetaxel, abraxane, carbazitaxel and derivatives of thereof. Derivatives of taxanes as employed herein includes reformulations of taxanes like taxol, for example in a micellar formulations, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

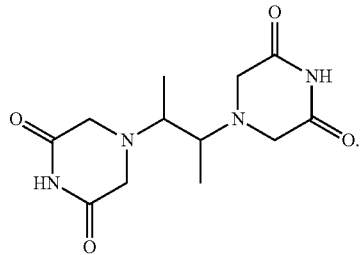 [SMILES: CC(C(C)N1CC(=O)NC(=O)C1)N1CC(=O)NC(=O)C1]

Type II poisons include amsacrine, etoposide, etoposide phosphate, teniposide and doxorubicin and fluoroquinolones.

In one embodiment a combination of chemotherapeutic agents employed is, for example a platin and 5-FU or a prodrug thereof, for example cisplatin or oxaplatin and capecitabine or gemcitabine, such as FOLFOX.

In one embodiment the chemotherapy comprises a combination of chemotherapy agents, in particular cytotoxic chemotherapeutic agents.

In one embodiment the chemotherapy combination comprises a platin, such as cisplatin and fluorouracil or capecitabine.

In one embodiment the chemotherapy combination in capecitabine and oxaliplatin (Xelox).

In one embodiment the chemotherapy is a combination of folinic acid and 5-FU, optionally in combination with oxaliplatin.

In one embodiment the chemotherapy is a combination of folinic acid, 5-FU and irinotecan (FOLFIRI), optionally in combination with oxaliplatin (FOLFIRINOX). The regimen consists of: irinotecan (180 mg/m² IV over 90 minutes) concurrently with folinic acid (400 mg/m² [or 2×250 mg/m²] IV over 120 minutes); followed by fluorouracil (400-500 mg/m² IV bolus) then fluorouracil (2400-3000 mg/m² intravenous infusion over 46 hours). This cycle is typically repeated every two weeks. The dosages shown above may vary from cycle to cycle.

In one embodiment the chemotherapy combination employs a microtubule inhibitor, for example vincristine sulphate, epothilone A, N-[2-[(4-Hydroxyphenyl)amino]-3-pyridinyl]-4-methoxybenzenesulfonamide (ABT-751), a taxol derived chemotherapeutic agent, for example paclitaxel, abraxane, or docetaxel or a combination thereof.

In one embodiment the chemotherapy combination comprises an antimetabolite such as capecitabine (xeloda), fludarabine phosphate, fludarabine (fludara), decitabine, raltitrexed (tomudex), gemcitabine hydrochloride and cladribine.

In one embodiment the anticancer therapy combination employs an mTor inhibitor. Examples of mTor inhibitors include: everolimus (RAD001), WYE-354, KU-0063794, papamycin (Sirolimus), Temsirolimus, Deforolimus (MK-8669), AZD8055 and BEZ235 (NVP-BEZ235).

In one embodiment the anticancer therapy combination employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one embodiment the chemotherapy combination employs an AKT inhibitor. Examples of AKT inhibitors include: MK-2206 and AT7867.

In one embodiment the anticancer therapy employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one embodiment the chemotherapy combination employs a p38 inhibitor, for example as disclosed in WO2010/038086, such as N-[4-({4-[3-(3-tert-Butyl-1-p-tolyl-1H-pyrazol-5-yl)ureido]naphthalen-1-yloxy}methyl)pyridin-2-yl]-2-methoxyacetamide.

In one embodiment the combination employs a Bcl-2 inhibitor. Examples of Bcl-2 inhibitors include: obatoclax mesylate, ABT-737, ABT-263 (navitoclax) and TW-37.

In one embodiment the chemotherapy combination comprises ganciclovir, which may assist in controlling immune responses and/or tumour vasculation.

In one embodiment the anticancer therapy includes a PARP inhibitor.

In one embodiment the anticancer therapy includes an inhibitor of cancer metabolism with specific inhibition of the activity of the DHODH enzyme.

In one embodiment one or more therapies employed in the method herein are metronomic, that is a continuous or frequent treatment with low doses of anticancer drugs, often given concomitant with other methods of therapy.

In one embodiment, there is provided the use of multiple cycles of treatment (such as chemotherapy) for example 2, 3, 4, 5, 6, 7 or 8.

Comprising" in the context of the present specification is intended to mean "including". Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The present application claims priority from SG10201807244X filed 24 Aug. 2018 and incorporated herein by reference. This application may be used as the basis for making corrections.

The invention will now be described with reference to the following examples, which are merely illustrative and should not be construed as limiting the scope of the present invention.

EXAMPLES

General Method A (Tryptamine)

A suitable round bottom flask or reacti-vial was charged with aryl halide (1 equiv.), tryptamine (1.1 equiv.), IPA (10 mL/mmol) and triethylamine (2 equiv.) and heated at 100° C. for 3 h (reaction monitored by UPLC analysis). On cooling the reaction mixture was evaporated to dryness and the resultant residue partitioned between ethyl acetate and water. The organic phase was separated and sequentially washed with saturated bicarbonate solution, water, brine, then dried over sodium sulfate, filtered and evaporated. Purification, if required was performed by chromatography or trituration.

General Method B (Suzuki)

A suitable round bottom flask or reacti-vial was charged with aryl halide (1 equiv.), aryl boronic acid (1.5-2.0 equiv.), potassium carbonate (1.5-2.0 equiv.), dioxane/water ([5:1] about 60 vol).

Head space was flushed with nitrogen gas, then [1,1'-Bis(diphenylphosphino)ferrocene]dichloropalladium(II) dichloride (0.2-0.3 equiv.) was added. The reaction mixture was heated under nitrogen at 100° C. for 2-24 h until complete as determined by UPLC analysis. The reaction mixture was evaporated to dryness and applied to a silica column as a slurry in DCM; or preabsorbed onto celite, which was loaded in to a dry load unit and placed in series with a silica cartridge. The desired product was eluted with a gradient of ethyl acetate in hexane, sometimes more polar eluent of methanol (0-10%) in ethyl acetate may be required. Further chromatography on silica eluting with 7M ammonia in methanol (0-10%) in DCM may be required. Trituration with diethyl ether and subsequent filtration afforded the desired product.

General Method C (TFA deBOC)

TFA (0.2-0.5 mL) was added to a solution of BOC compound (20-200 mg) in DCM (3-10 mL). Once complete as judged by UPLC, the reaction mixture was loaded on to an SCX resin cartridge (0.5 g or 1.0 g). The cartridge was washed through with methanol (10 mL). The product was eluted as the free base, eluting with 7M ammonia in methanol (10 mL). The free based material was evaporated, triturated with ether and collected by filtration. Dried in a desiccator <10 mbar.

Example 1 Preparation of 1-(4-((2-(1H-indol-3-yl)ethyl)amino)-2-(5-fluoropyridin-3-yl)-5,8-dihydropyrido [3,4-d]pyrimidin-7(6H)-yl)ethan-1-one

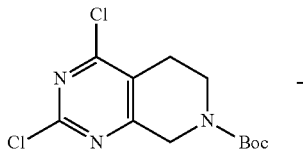

Chemical Formula: $C_{12}H_{15}Cl_2N_3O_2$
Molecular Weight: 304.17

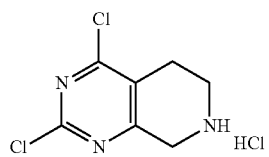

Chemical Formula: $C_7H_8Cl_3N_3$
Molecular Weight: 240.51

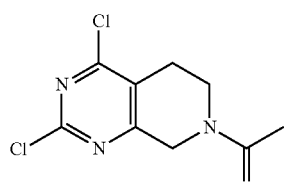

Chemical Formula: $C_9H_9Cl_2N_3O$
Molecular Weight: 246.09

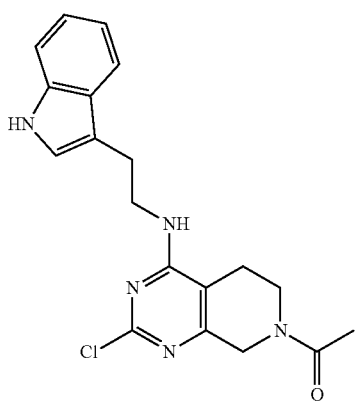

Chemical Formula: $C_{19}H_{20}ClN_5O$
Molecular Weight: 369.85

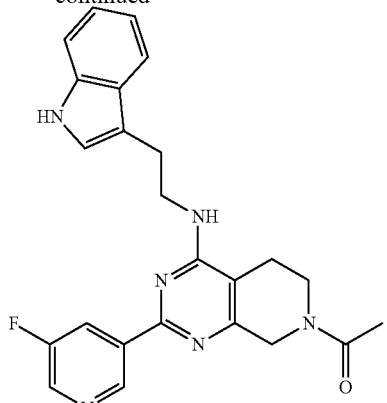

Chemical Formula: $C_{24}H_{23}FN_6O$
Molecular Weight: 430.49

Step 1 2,4-dichloro-5,6,7,8-tetrahydropyrido[3,4-d]pyrimidine hydrochloride

To a solution of t-butyl 2,4-dichloro-5,6-dihydropyrido[3,4-d]pyrimidine-7(8H)carboxylate (5.2 g) in DCM (10 mL) was added HCl (4N in dioxane) (4 mL). The reaction mixture was stirred at ambient temperature. After completion (reaction monitored by TLC), solvent was evaporated under reduce pressure. The obtained solid was then successively triturated with ethyl acetate, then diethyl ether and dried to give the desired product as a beige solid (3.5 g, 85%)

UPLC-MS (Basic Method, 2 min): rt 0.79 min, m/z 204/206/208 [M−H]⁻

$^1$H NMR (400 MHz, DMSO-d$_6$) δ ppm 3.00 (t, J=6.15 Hz, 2H) 3.43 (t, J=6.16 Hz, 2H) 4.35 (s, 2H) 10.08 (br s, 2H)

Step 2 (2,4-Dichloro-5,8-dihydropyrido[3,4-d]pyrimidin-7(6H)-yl)ethan-1-one

Triethylamine (60 µL, 2 equiv.) was added to a suspension of 2,4-dichloro-5,6,7,8-tetrahydropyrido[3,4-d]pyrimidine hydrochloride (50 mg, 1 equiv.) in DCM (500 µL). After stirring for few minutes acetic anhydride (30 µL, 1.5 equiv.) was added. The mixture became cloudy. After completion (reaction monitored by UPLC analysis), DCM was added followed by water. The isolated organic phase was then dried over sodium sulfate, filtered and evaporated, to give the desired product as crude as a solid (46 mg, 90%).

UPLC-MS (Acidic Method, 2 min): rt 0.75 min, m/z 246/248/250 [M+H]⁺

$^1$H NMR (400 MHz, CHLOROFORM-d) δ ppm 2.15-2.21 (m, 3H) 2.80-2.86 (m, 1H) 2.87-2.94 (m, 1H) 3.73-3.80 (m, 1H) 3.86-3.94 (m, 1H) 4.62-4.69 (m, 1H) 4.76-4.83 (m, 1H) (All peaks duplicate due to the presence of rotamers)

Step 3 1-(4-((2-(1H-indol-3-yl)ethyl)amino)-2-chloro-5,8-dihydropyrido[3,4-d]pyrimidin-7(6H)-yl)ethan-1-one Prepared according to general method A, using 1-(2,4-dichloro-5,8-dihydropyrido[3,4-d]pyrimidin-7(6H)-yl)ethan-1-one (46 mg) to give the desired product as crude as an orange solid (69 mg, 100%)

UPLC-MS (Acidic Method, 2 min): rt 0.92 min, m/z 370/371 [M+H]⁺

¹H NMR (400 MHz, CHLOROFORM-d+drop of METHANOL-d₄) δ ppm 7.48-7.60 (m, 1H), 7.30-7.36 (m, 1H), 7.08-7.16 (m, 1H), 6.98-7.07 (m, 2H), 4.26-4.55 (m, 2H), 3.60-3.72 (m, 2H), 3.30-3.34 (m, 2H), 2.94-3.07 (m, 2H), 2.08-2.16 (m, 2H), 1.93-2.08 (m, 3H)

Step 4 1-(4-((2-(1H-indol-3-yl)ethyl)amino)-2-(5-fluoropyridin-3-yl)-5,8-dihydropyrido[3,4-d]pyrimidin-7(6H)-yl)ethan-1-one Prepared according to general method B, using 1-(4-((2-(1H-indol-3-yl)ethyl)amino)-2-chloro-5,8-dihydropyrido[3,4-d]pyrimidin-7(6H)-yl)ethan-1-one (84 mg) and 5-fluoropyridine-3-boronic acid (80 mg) to give the desired product as a white solid (45 mg, 46%).

UPLC-MS (Acidic Method, 4 min): rt 1.40 min, m/z 431.2 [M+H]⁺

¹⁹F NMR (400 MHz, DMSO-d₆) δ ppm −127.64 proton decoupled

¹H NMR (400 MHz, DMSO-d₆) δ ppm 10.83 (br s, 1H), 9.34 (t, J=1.8 Hz, 1H), 8.68 (t, J=2.4 Hz, 1H), 8.26-8.45 (m, 1H), 7.60 (d, J=8.0 Hz, 1H), 7.33-7.37 (m, 1H), 7.29-7.32 (m, 1H), 7.22 (d, J=2.0 Hz, 1H), 7.04-7.11 (m, 1H), 6.98 (ddd, J=7.8, 7.0, 1.0 Hz, 1H), 4.53 (br d, J=13.8 Hz, 2H), 3.77-3.85 (m, 2H), 3.73-3.78 (m, 2H), 3.04 (br t, J=7.5 Hz, 2H), 2.53 (br s, 1H), 2.42 (br t, J=5.5 Hz, 1H), 2.12 (d, J=6.5 Hz, 3H).

Example 2 Preparation of N-(2-(1H-indol-3-yl)ethyl)-2-(5-fluoropyridin-3-yl)-7-(methylsulfonyl)-5,6,7,8-tetrahydropyrido[3,4-d]pyrimidin-4-amine

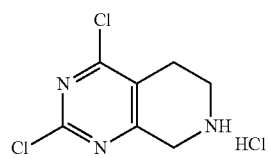

Chemical Formula: C₇H₈Cl₃N₃
Molecular Weight: 240.51

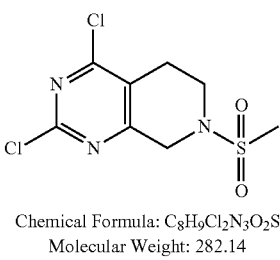

Chemical Formula: C₈H₉Cl₂N₃O₂S
Molecular Weight: 282.14

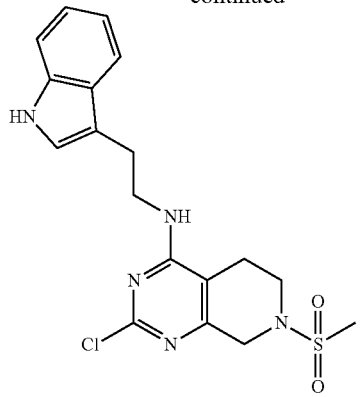

Chemical Formula: C₁₈H₂₀ClN₅O₂S
Molecular Weight: 405.90

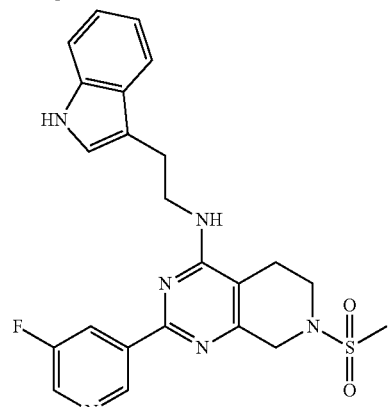

Chemical Formula: C₂₃H₂₃FN₆O₂S
Molecular Weight: 466.54

Step 1 2,4-dichloro-7-(methylsulfonyl)-5,6,7,8-tetrahydropyrido[3,4-d]pyrimidine Triethylamine (60 μL, 2 equiv.) was added to a suspension of 2,4-dichloro-5,6,7,8-tetrahydropyrido[3,4-d]pyrimidine hydrochloride (50 mg, 1 equiv.) in DCM (500 μL). After stirring for few minutes methyl sulfonylchloride (25 μL, 1.5 equiv.) was added. The mixture became cloudy. After completion (reaction monitored by UPLC analysis), DCM was added followed by water. The organic phase was then dried over sodium sulfate, filtered and evaporated, to give the desired product as a solid (57 mg, 98%). UPLC-MS (Acidic Method, 2 min): rt 0.83 min, m/z 282/284 [M+H]⁺

¹H NMR (400 MHz, CHLOROFORM-d) δ ppm 4.36-4.60 (m, 2H), 3.70-3.70 (m, 1H), 3.57-3.67 (m, 2H), 2.94-3.01 (m, 2H)

Step 2 N-(2-(1H-indol-3-yl)ethyl)-2-chloro-7-(methylsulfonyl)-5,6,7,8-tetrahydropyrido[3,4-d]pyrimidin-4-amine Prepared according to general method A, using 2,4-dichloro-7-(methylsulfonyl)-5,6,7,8-tetrahydropyrido[3,4-d]pyrimidine (57 mg) to give the desired product as crude as an orange solid (78 mg, 95%). UPLC-MS (Acidic Method, 2 min): rt 0.97 min, m/z 406/408 [M+H]⁺

¹H NMR (400 MHz, CHLOROFORM-d+drop of METHANOL-d₄) δ ppm 7.51-7.63 (m, 1H), 7.32-7.39 (m, 1H), 7.12-7.20 (m, 1H), 7.04-7.10 (m, 1H), 6.99-7.03 (m, 1H), 3.61-3.82 (m, 2H), 3.37-3.54 (m, 2H), 2.98-3.10 (m, 2H), 2.82-2.84 (m, 2H), 2.78-2.81 (m, 3H), 2.15-2.25 (m, 2H).

Step 3 N-(2-(1H-indol-3-yl)ethyl)-2-(5-fluoropyridin-3-yl)-7-(methylsulfonyl)-5,6,7,8-tetrahydropyrido[3,4-d]pyrimidin-4-amine Prepared according to general method B, using N-(2-(1H-indol-3-yl)ethyl)-2-chloro-7-(methylsulfonyl)-5,6,7,8-tetrahydropyrido[3,4-d]pyrimidin-4-amine (78 mg) and 5-fluoropyridine-3-boronic acid (60 mg) to give the desired product as a white solid (58 mg, 62%).

UPLC-MS (Acidic Method, 4 min): rt 1.58 min, m/z 467.1 [M+H]$^+$ $^{19}$F NMR (400 MHz, DMSO-d$_6$) δ ppm −127.59 proton decoupled $^1$H NMR (400 MHz, DMSO-d$_6$) δ ppm 10.83 (br d, J=1.3 Hz, 1H), 9.33 (t, J=1.8 Hz, 1H), 8.69 (d, J=2.8 Hz, 1H), 8.30-8.35 (m, 1H), 7.61 (d, J=7.5 Hz, 1H), 7.38 (t, J=5.9 Hz, 1H), 7.34 (dt, J=8.1, 1.0 Hz, 1H), 7.22 (d, J=2.3 Hz, 1H), 7.07 (ddd, J=8.1, 6.8, 1.1 Hz, 1H), 6.98 (ddd, J=7.8, 7.0, 1.0 Hz, 1H), 4.27 (s, 1H), 3.75-3.89 (m, 2H), 3.52 (t, J=5.9 Hz, 1H), 2.97-3.13 (m, 5H), 2.58 (br t, J=5.9 Hz, 1H).

Example 3 Preparation of 5-(4-((2-(1H-indol-3-yl)ethyl)amino)-7-(cyanomethyl)-5,6,7,8-tetrahydropyrido[3,4-d]pyrimidin-2-yl)nicotinonitrile

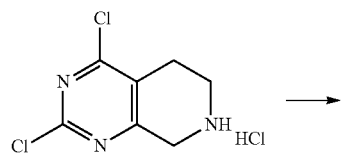

Chemical Formula: C$_7$H$_8$Cl$_3$N$_3$
Molecular Weight: 240.51

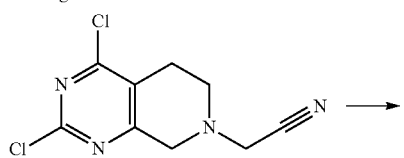

Chemical Formula: C$_9$H$_8$Cl$_2$N$_4$
Molecular Weight: 243.09

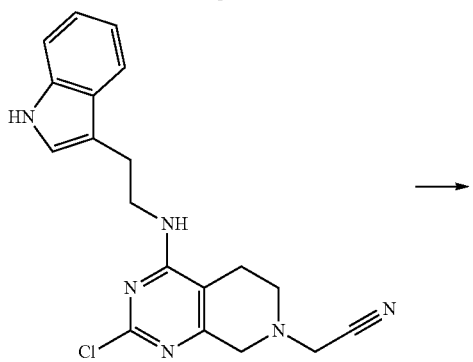

Chemical Formula: C$_{19}$H$_{19}$ClN$_6$
Molecular Weight: 366.85

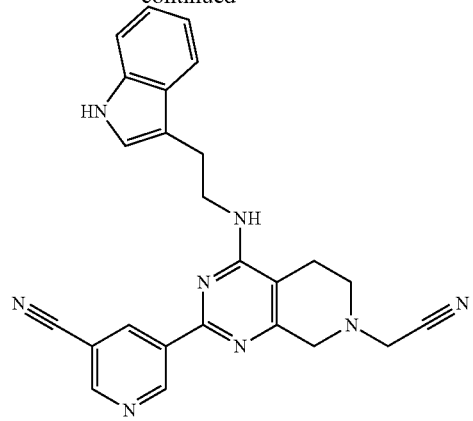

Chemical Formula: C$_{25}$H$_{22}$N$_8$
Molecular Weight: 434.51

Step 1 2-(2,4-dichloro-5,8-dihydropyrido[3,4-d]pyrimidin-7(6H)-yl)acetonitrile

Triethylamine (1.4 mL, 2.5 equiv.) was added to a suspension of 2,4-dichloro-5,6,7,8-tetrahydropyrido[3,4-d]pyrimidine hydrochloride (0.99 g, 1 equiv.) in DCM (500 µL). After stirring for few minutes bromoacetonitrile (315 µL, 1.5 equiv.) was added. After completion (reaction monitored by UPLC analysis), DCM was added followed by water. The organic phase was then dried over sodium sulfate, filtered and evaporated, to give a sticky oil. Purification on silica, eluting with a gradient of methanol 0-5% in DCM, gave the desired impure product as a foam (540 mg).

UPLC-MS (Acidic Method, 2 min): rt 0.86 min, m/z 243 [M+H]$^+$ $^1$H NMR (400 MHz, CHLOROFORM-d) δ ppm No $^1$H NMR was run at this stage.

Step 2 2-(4-((2-(1H-indol-3-yl)ethyl)amino)-2-chloro-5,8-dihydropyrido[3,4-d]pyrimidin-7(6H)-yl)acetonitrile Prepared according to general method A, using 2-(2,4-dichloro-5,8-dihydropyrido[3,4-d]pyrimidin-7(6H)-yl)acetonitrile (500 mg). Purification on silica (Telos 20 g column cartridge), eluting with a gradient of methanol 0-5% in DCM to give the desired product, as a pale yellow solid (249 mg).

UPLC-MS (Acidic Method, 2 min): rt 0.98 min, m/z 367 [M+H]$^+$ $^1$H NMR (400 MHz, CHLOROFORM-d+drop of METHANOL-d$_4$) δ ppm 8.04-8.21 (m, 1H), 7.57-7.70 (m, 1H), 7.35-7.44 (m, 1H), 7.20-7.26 (m, 1H), 7.11-7.18 (m, 1H), 7.04-7.09 (m, 1H), 4.74-4.94 (m, 1H), 3.81-3.90 (m, 2H), 3.68-3.68 (m, 1H), 3.64-3.69 (m, 1H), 3.58-3.62 (m, 2H), 3.06-3.14 (m, 2H), 2.78-2.84 (m, 2H), 2.13-2.27 (m, 2H).

Step 3 5-(4-((2-(1H-indol-3-yl)ethyl)amino)-7-(cyanomethyl)-5,6,7,8-tetrahydropyrido[3,4-d]pyrimidin-2-yl)nicotinonitrile Prepared according to general method B, using 2-(4-((2-(1H-indol-3-yl)ethyl)amino)-2-chloro-5,8-dihydropyrido[3,4-d]pyrimidin-7(6H)-yl)acetonitrile (120 mg) and 5-cyano- 3-pyridinyl boronic acid (70 mg) to give the desired product as a beige solid (57 mg, 40%).

UPLC-MS (Acidic Method, 4 min): rt 1.47 min, m/z 428 [M+H]+

$^1$H NMR (400 MHz, DMSO-d$_6$) δ ppm 10.70-10.95 (m, 1H), 9.20-9.39 (m, 1H), 8.61-8.82 (m, 1H), 8.23-8.38 (m, 1H), 7.53-7.68 (m, 1H), 7.28-7.47 (m, 2H), 7.16-7.24 (m, 1H), 7.02-7.11 (m, 1H), 6.92-7.01 (m, 1H), 3.92-4.05 (m, 2H), 3.73-3.85 (m, 2H), 3.56-3.65 (m, 2H), 2.99-3.10 (m, 2H), 2.78-2.90 (m, 2H).

Example 4 Preparation of 2-(4-((2-(1H-indol-3-yl)ethyl)amino)-2-(5-fluoropyridin-3-yl)-5,8-dihydropyrido[3,4-d]pyrimidin-7(6H)-yl)acetonitrile

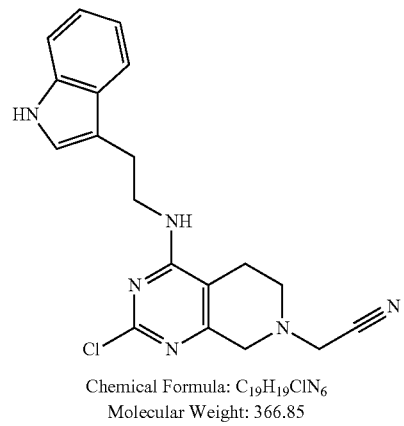

Chemical Formula: C$_{19}$H$_{19}$ClN$_6$
Molecular Weight: 366.85

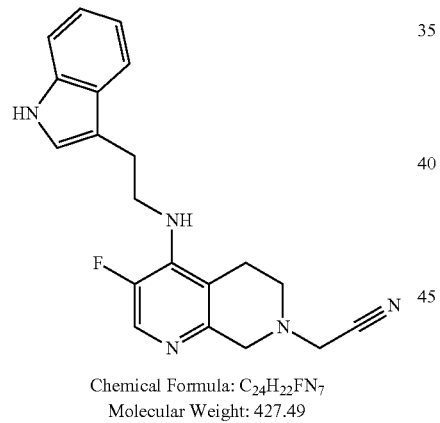

Chemical Formula: C$_{24}$H$_{22}$FN$_7$
Molecular Weight: 427.49

Step 3 2-(4-((2-(1H-indol-3-yl)ethyl)amino)-2-(5-fluoropyridin-3-yl)-5,8-dihydropyrido[3,4-d]pyrimidin-7(6H)-yl)acetonitrile Prepared according to general method B, using 2-(4-((2-(1H-indol-3-yl)ethyl)amino)-2-chloro-5,8-dihydropyrido[3,4-d]pyrimidin-7(6H)-yl)acetonitrile (120 mg) and 5-fluoropyridine-3-boronic acid (70 mg) to give the desired product as a white solid (10 mg, 7%).

UPLC-MS (Acidic Method, 4 min): rt 1.55 min, m/z 435 [M+H]+

$^1$H NMR (400 MHz, CHLOROFORM-d) δ ppm 8.68-8.87 (m, 1H), 8.05-8.16 (m, 1H), 7.90-8.01 (m, 1H), 6.71-6.82 (m, 1H), 6.41-6.52 (m, 1H), 6.19-6.30 (m, 3H), 3.06-3.14 (m, 4H), 2.82-2.89 (m, 2H), 2.63-2.75 (m, 3H), 2.27-2.35 (m, 2H), 2.05-2.16 (m, 2H), 1.65-1.76 (m, 2H).

Example 5 Preparation of N-(2-(1H-indol-3-yl)ethyl)-2-(5-fluoropyridin-3-yl)-7-isopropyl-5,6,7,8-tetrahydropyrido[3,4-d]pyrimidin-4-amine

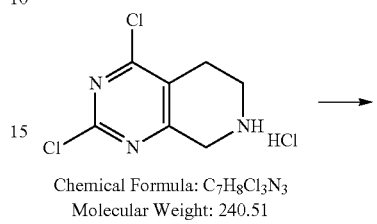

Chemical Formula: C$_7$H$_8$Cl$_3$N$_3$
Molecular Weight: 240.51

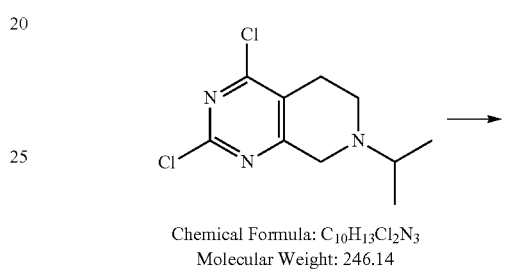

Chemical Formula: C$_{10}$H$_{13}$Cl$_2$N$_3$
Molecular Weight: 246.14

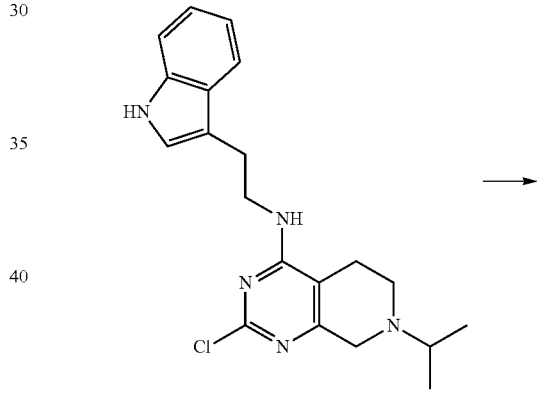

Chemical Formula: C$_{20}$H$_{24}$ClN$_5$
Molecular Weight: 369.90

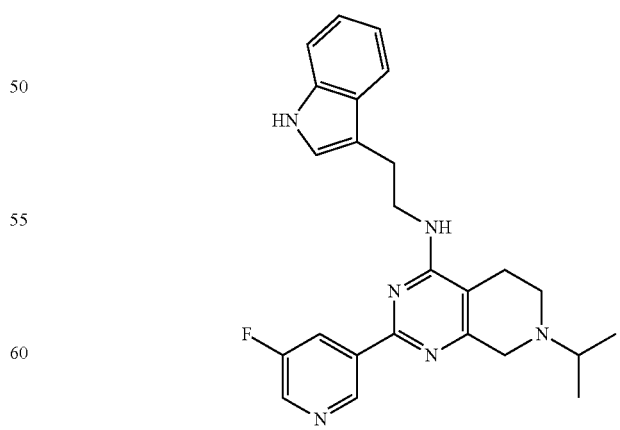

Chemical Formula: C$_{25}$H$_{27}$FN$_6$
Molecular Weight: 430.53

Step 1 2,4-dichloro-7-isopropyl-5,6,7,8-tetrahydropyrido[3,4-d]pyrimidine

Triethylamine (1 mL, 2 equiv.) was added to a suspension of 2,4-dichloro-5,6,7,8-tetrahydropyrido[3,4-d]pyrimidine hydrochloride (0.9 g, 1 equiv.) in DCM (20 mL). After stirring for 10-15 minutes at ambient temperature, acetic acid (630 µL, 3 equiv.) was added, followed by acetone (540 µL). The stirring was continued for 10 minutes before addition of sodium triacetoxyborohydride (1.24 g, 1.6 equiv.). After 1 day, the reaction mixture was diluted with DCM and was washed with a saturated solution of sodium bicarbonate. The organic phase was then dried over sodium sulfate, filtered and evaporated to give a brown oil. Purification on silica (Telos 40 g cartridge) eluting with a gradient of ethyl acetate 0 to 50% in Hexane, afforded the desired product as a yellow oil (536 mg, 54%).

UPLC-MS (Basic Method, 2 min): rt 1.01 min, m/z 246/248 [M+H]$^+$ $^1$H NMR (400 MHz, CHLOROFORM-d) δ ppm 3.73-3.78 (m, 2H), 2.90-3.03 (m, 1H), 2.80-2.85 (m, 4H), 1.08-1.16 (m, 6H).

Step 2 N-(2-(1H-indol-3-yl)ethyl)-2-chloro-7-isopropyl-5,6,7,8-tetrahydropyrido[3,4-d]pyrimidin-4-amine Prepared according to general method A, using 2,4-dichloro-7-isopropyl-5,6,7,8-tetrahydropyrido[3,4-d]pyrimidine (150 mg). Purification on silica (Telos 4 g cartridge), eluting with a gradient of MeOH 0 to 5% in DCM, afforded the desired product as a beige foam (160 mg, 90%). UPLC-MS (Acidic Method, 2 min): rt 0.72 min, m/z 370/372 [M+H]$^+$ $^1$H NMR (400 MHz, CHLOROFORM-d+drop of METHANOL-d$_4$) δ ppm 7.98-8.10 (m, 1H), 7.63-7.68 (m, 1H), 7.38-7.43 (m, 1H), 7.21-7.26 (m, 1H), 7.12-7.18 (m, 1H), 7.03-7.06 (m, 1H), 4.71-4.79 (m, 1H), 3.81-3.88 (m, 2H), 3.55-3.59 (m, 2H), 3.06-3.13 (m, 2H), 2.84-2.92 (m, 1H), 2.70-2.75 (m, 2H), 2.14-2.20 (m, 2H), 1.08-1.12 (m, 6H)

Step 3 N-(2-(1H-indol-3-yl)ethyl)-2-(5-fluoropyridin-3-yl)-7-isopropyl-5,6,7,8-tetrahydropyrido[3,4-d]pyrimidin-4-amine Prepared according to general method B, using N-(2-(1H-indol-3-yl)ethyl)-2-chloro-7-isopropyl-5,6,7,8-tetrahydropyrido[3,4-d]pyrimidin-4-amine (65 mg) and 5-fluoropyridine-3-boronic acid (60 mg) to give the desired product as a white solid (50 mg, 66%).

UPLC-MS (Acidic Method, 4 min): rt 1.07 min, m/z 431.2 [M+H]$^+$ $^{19}$F NMR (400 MHz, DMSO-d$_6$) δ ppm −127.79 proton decoupled $^1$H NMR (400 MHz, DMSO-d$_6$) δ ppm 10.83 (br d, J=1.5 Hz, 1H), 9.32 (t, J=1.8 Hz, 1H), 8.66 (d, J=2.8 Hz, 1H), 8.24-8.37 (m, 1H), 7.61 (d, J=7.3 Hz, 1H), 7.35 (dt, J=8.0, 0.9 Hz, 1H), 7.21 (d, J=2.3 Hz, 1H), 7.14 (br t, J=5.8 Hz, 1H), 7.08 (ddd, J=8.1, 7.0, 1.3 Hz, 1H), 6.98 (ddd, J=8.0, 7.0, 1.1 Hz, 1H), 3.72-3.83 (m, 1H), 3.54 (s, 1H), 2.99-3.09 (m, 1H), 2.91 (dt, J=13.1, 6.4 Hz, 1H), 2.76 (br t, J=5.6 Hz, 1H), 2.42 (br t, J=5.5 Hz, 1H), 1.08 (d, J=6.5 Hz, 1H).

Example 6 Preparation of N-(2-(1H-indol-3-yl)ethyl)-2-(5-fluoropyridin-3-yl)-7-methyl-5,6,7,8-tetrahydropyrido[3,4-d]pyrimidin-4-amine

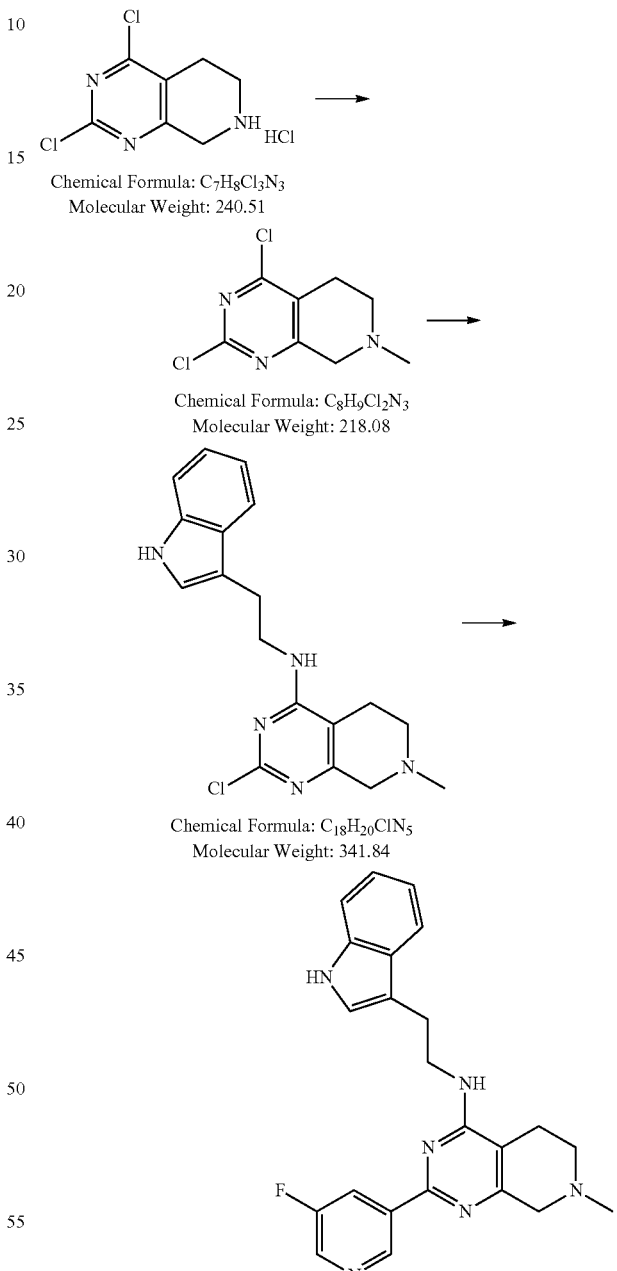

Chemical Formula: C$_7$H$_8$Cl$_3$N$_3$
Molecular Weight: 240.51

Chemical Formula: C$_8$H$_9$Cl$_2$N$_3$
Molecular Weight: 218.08

Chemical Formula: C$_{18}$H$_{20}$ClN$_5$
Molecular Weight: 341.84

Chemical Formula: C$_{23}$H$_{23}$FN$_6$
Molecular Weight: 402.48

Step 1 2,4-dichloro-7-methyl-5,6,7,8-tetrahydropyrido[3,4-d]pyrimidine

Triethylamine (1.1 mL, 2 equiv.) was added to a suspension of 2,4-dichloro-5,6,7,8-tetrahydropyrido[3,4-d]pyrimidine hydrochloride (1.0 g, 1 equiv.) in DCM (20 mL). After stirring for 10-15 minutes at ambient temperature, acetic acid (720 μL, 3 equiv.) was added, followed by formaldehyde solution (37 wt % in H2O) (720 μL). The stirring was continued for 10 minutes before addition of sodium triacetoxyborohydride (1.41 g, 1.6 equiv.). After 3 hours, the reaction mixture was diluted with DCM and was washed with a saturated solution of sodium bicarbonate. The organic phase was then dried over sodium sulfate, filtered and evaporated to give a brown oil (1.08 g). Purification on silica (Telos 40 g cartridge) eluting with a gradient of ethyl acetate 5 to 100% in hexane, afforded the desired product as a yellow oil (677 mg, 68%).

UPLC-MS (Basic Method, 2 min): rt 0.83 min, m/z 218/220/222 [M+H]$^+$ $^1$H NMR (400 MHz, CHLOROFORM-d) δ ppm 3.60-3.63 (m, 2H), 2.83-2.88 (m, 2H), 2.73-2.78 (m, 2H), 2.47-2.51 (m, 3H).

Step 2 N-(2-(1H-indol-3-yl)ethyl)-2-chloro-7-methyl-5,6,7,8-tetrahydropyrido[3,4-d]pyrimidin-4-amine Prepared according to general method A, using 2,4-dichloro-7-methyl-5,6,7,8-tetrahydropyrido[3,4-d]pyrimidine (150 mg). Purification on silica (Telos 4 g cartridge), eluting with a gradient of MeOH 5 to 10% in DCM, afforded the desired product as a beige foam (175 mg, 74%). UPLC-MS (Acidic Method, 2 min): rt 0.71 min, m/z 342/344 [M+H]$^+$ $^1$H NMR (400 MHz, CHLOROFORM-d+drop of METHANOL-d$_4$) δ ppm 7.61-7.68 (m, 1H), 7.36-7.44 (m, 1H), 7.21-7.26 (m, 1H), 7.12-7.18 (m, 1H), 7.03-7.06 (m, 1H), 4.72-4.80 (m, 1H), 3.81-3.88 (m, 2H), 3.41-3.44 (m, 2H), 3.07-3.13 (m, 2H), 2.61-2.67 (m, 2H), 2.41-2.45 (m, 3H), 2.15-2.21 (m, 2H).

Step 3 N-(2-(1H-indol-3-yl)ethyl)-2-(5-fluoropyridin-3-yl)-7-methyl-5,6,7,8-tetrahydropyrido[3,4-d]pyrimidin-4-amine Prepared according to general method B, using N-(2-(1H-indol-3-yl)ethyl)-2-chloro-7-methyl-5,6,7,8-tetrahydropyrido[3,4-d]pyrimidin-4-amine (70 mg) and 5-fluoropyridine-3-boronic acid (70 mg) to give the desired product as a buff solid (50 mg, 60%).

UPLC-MS (Acidic Method, 4 min): rt 1.04 min, m/z 403.2 [M+H]$^+$ $^{19}$F NMR (400 MHz, DMSO-d$_6$) δ ppm −127.76 proton decoupled $^1$H NMR (400 MHz, DMSO-d$_6$) δ ppm 10.83 (br s, 1H), 9.32 (s, 1H), 8.66 (d, J=2.8 Hz, 1H), 8.27-8.38 (m, 1H), 7.61 (d, J=7.5 Hz, 1H), 7.35 (d, J=8.0 Hz, 1H), 7.21 (d, J=2.3 Hz, 1H), 7.17 (br t, J=5.5 Hz, 1H), 7.07 (t, J=7.2 Hz, 1H), 6.94-7.01 (m, 1H), 3.69-3.87 (m, 2H), 3.40 (s, 2H), 3.04 (br t, J=7.5 Hz, 2H), 2.64-2.69 (m, 2H), 2.43-2.48 (m, 2H), 2.37 (s, 3H).

Example 7 Preparation of N-(2-(1H-indol-3-yl)ethyl)-2-(pyridin-3-yl)-5,6,7,8-tetrahydropyrido[4,3-d]pyrimidin-4-amine

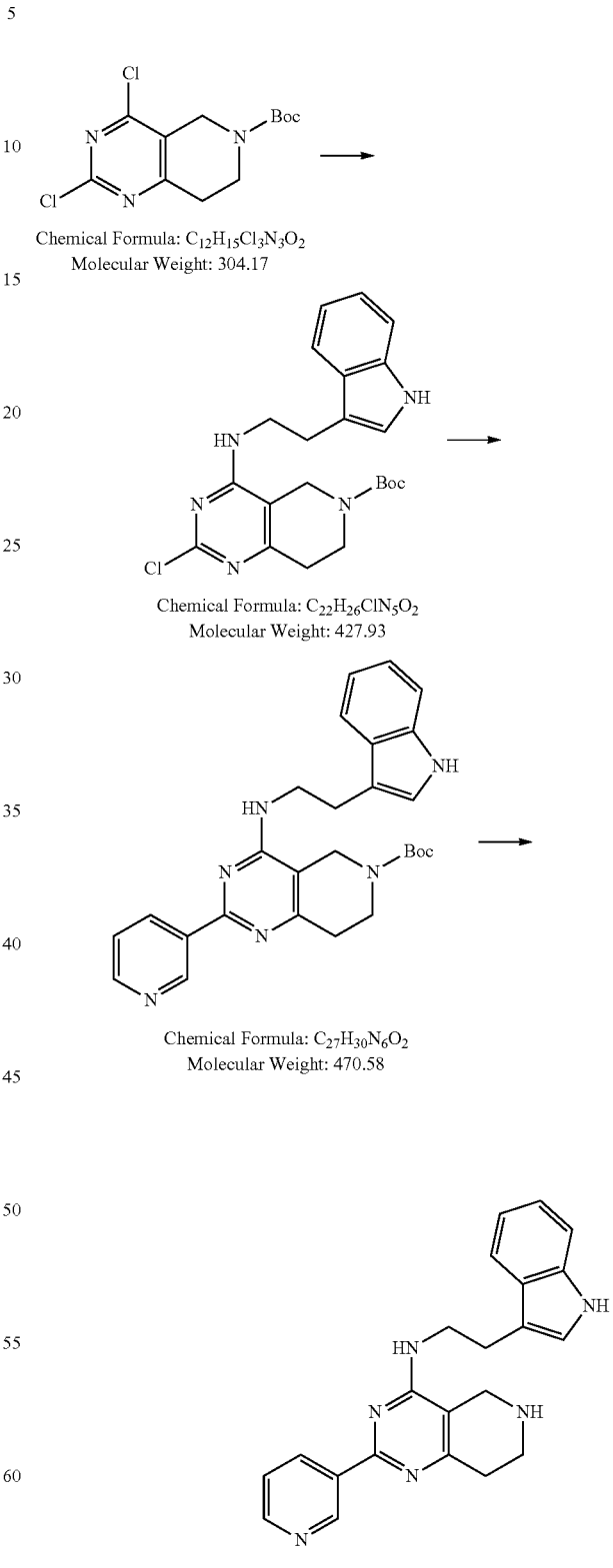

Step 1 t-Butyl 4-((2-(1H-indol-3-yl)ethyl)amino)-2-chloro-7,8-dihydropyrido[4,3-d]pyrimidine-6(5H)-carboxylate Prepared according to general method A, using t-butyl 2,4-dichloro-7,8-dihydropyrido[4,3-d]pyrimidine-6(5H)-carboxylate (410 mg) to give the desired product as a solid (630 mg, >100%)

UPLC-MS (Acidic Method, 2 min): rt 1.21 min, m/z 428/430 [M+H]$^+$ $^1$H NMR (400 MHz, CHLOROFORM-d) δ ppm 7.97-8.18 (m, 1H), 7.59-7.68 (m, 1H), 7.34-7.44 (m, 1H), 7.19-7.26 (m, 1H), 7.11-7.18 (m, 1H), 7.05-7.09 (m, 1H), 4.09-4.17 (m, 2H), 3.79-3.90 (m, 2H), 3.59-3.68 (m, 2H), 3.04-3.15 (m, 2H), 2.70-2.80 (m, 2H), 1.46-1.52 (m, 9H).

Step 2 t-Butyl 4-((2-(1H-indol-3-yl)ethyl)amino)-2-(pyridin-3-yl)-7,8-dihydropyrido[4,3-d]pyrimidine-6(5H)-carboxylate Prepared according to general method B, using t-butyl 4-((2-(1H-indol-3-yl)ethyl)amino)-2-chloro-7,8-dihydropyrido[4,3-d]pyrimidine-6(5H)-carboxylate (200 mg) and pyridine-3-boronic acid (80 mg) to give the desired product as a residue (70 mg, 30%).

UPLC-MS (Basic Method, 2 min): rt 1.21 min, m/z 471.2 [M+H]$^+$ $^1$H NMR (400 MHz, CHLOROFORM-d) δ ppm 9.64 (d, J=1.8 Hz, 1H), 8.61-8.72 (m, 2H), 8.12 (br s, 1H), 7.65 (d, J=8.0 Hz, 1H), 7.35-7.45 (m, 2H), 7.21-7.27 (m, 1H), 7.16 (td, J=7.5, 1.0 Hz, 1H), 7.06-7.14 (m, 1H), 4.55-4.64 (m, 1H), 4.06-4.18 (m, 2H), 3.95-4.05 (m, 2H), 3.69-3.75 (m, 2H), 3.18 (br t, J=5.9 Hz, 2H), 2.84-2.92 (m, 2H), 1.48-1.55 (m, 9H). Best interpretation

Step 3 N-(2-(1H-indol-3-yl)ethyl)-2-(pyridin-3-yl)-5,6,7,8-tetrahydropyrido[4,3-d]pyrimidin-4-amine 5N HCl in IPA (2 mL) was added to a solution of t-butyl 4-((2-(1H-indol-3-yl)ethyl)amino)-2-(pyridin-3-yl)-7,8-dihydropyrido[4,3-d]pyrimidine-6(5H)-carboxylate (70 mg) in DCM (10 mL). A transient solid formed and the reaction mixture darkened in colour. After 18h the DCM was evaporated and the IPA residue diluted with methanol/water [1:1] (2 mL). The mixture was loaded onto a 0.5 g SCX cartridge and washed through with methanol/water [1:1] (10 mL), then methanol (2×10 mL). The product was eluted as the free base, eluting with 7M ammonia in methanol (10 mL). The free based material was evaporated, then purified on silica, eluting with a gradient of 7M ammonia in methanol (1-10%) in DCM, to afford the desired product as a white solid (30 mg, 54%). UPLC-MS (Basic Method, 2 min): rt 0.95 min, m/z 371.2 [M+H]$^+$ $^1$H NMR (400 MHz, DMSO-d$_6$) δ ppm 10.83 (br s, 1H), 9.47 (dd, J=2.1, 0.9 Hz, 1H), 8.64 (dd, J=4.8, 1.8 Hz, 1H), 8.57 (dt, J=8.1, 1.9 Hz, 1H), 7.61 (d, J=8.0 Hz, 1H), 7.48 (ddd, J=7.9, 4.8, 0.9 Hz, 1H), 7.35 (dt, J=8.0, 0.9 Hz, 1H), 7.21 (d, J=2.3 Hz, 1H), 7.08 (ddd, J=8.1, 7.1, 1.1 Hz, 1H), 6.99 (ddd, J=7.9, 6.9, 1.0 Hz, 1H), 6.91 (t, J=5.6 Hz, 1H), 3.71-3.82 (m, 1H), 3.57 (s, 1H), 3.02-3.07 (m, 2H), 2.99 (t, J=5.6 Hz, 2H), 2.64 (br t, J=5.6 Hz, 2H).

Example 8 Preparation of N-(2-(1H-indol-3-yl)ethyl)-2-(5-fluoropyridin-3-yl)-5,6,7,8-tetrahydropyrido[3,4-d]pyrimidin-4-amine

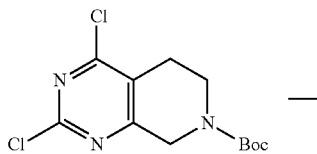

Chemical Formula: C$_{12}$H$_{15}$Cl$_3$N$_3$O$_2$
Molecular Weight: 304.17

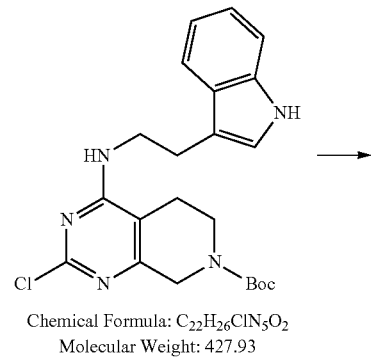

Chemical Formula: C$_{22}$H$_{26}$ClN$_5$O$_2$
Molecular Weight: 427.93

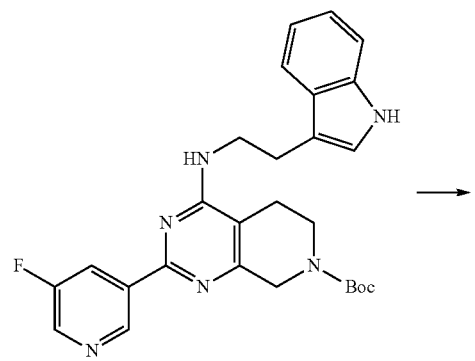

Chemical Formula: C$_{27}$H$_{29}$FN$_6$O$_2$
Molecular Weight: 488.57

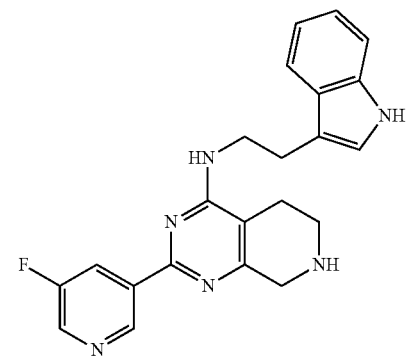

Chemical Formula: C$_{22}$H$_{22}$FN$_6$
Molecular Weight: 388.45

Step 1 t-Butyl 4-((2-(1H-indol-3-yl)ethyl)amino)-2-chloro-5,8-dihydropyrido[3,4-d]pyrimidine-7(6H)-carboxylate Prepared according to general method A, using t-butyl 2,4-dichloro-5,8-dihydropyrido[3,4-d]pyrimidine-7(6H)-carboxylate (470 mg) and purification by trituration with DCM, to give the desired product as a beige solid (370 mg, 55%).

UPLC-MS (acidic Method, 2 min): rt 1.22 min, m/z 428.2/430.2 [M+H]$^+$ $^1$H NMR (400 MHz, DMSO-d$_6$) δ ppm 10.82 (br s, 1H), 7.65 (d, J=7.8 Hz, 1H), 7.54 (br s, 1H), 7.34 (d, J=8.0 Hz, 1H), 7.19 (d, J=2.3 Hz, 1H), 7.07 (td, J=7.5, 1.0 Hz, 1H), 6.98 (td, J=7.5, 1.0 Hz, 1H), 4.27 (br s, 2H), 3.49-3.70 (m, 4H), 2.95 (t, J=13.8 Hz, 2H), 2.36 (br t, J=5.8 Hz, 2H), 1.39-1.49 (m, 9H).

Step 2 t-Butyl 4-((2-(1H-indol-3-yl)ethyl)amino)-2-(5-fluoropyridin-3-yl)-5,8-dihydropyrido[3,4-d]pyrimidine-7(6H)-carboxylate Prepared according to general method B, using t-butyl 4-((2-(1H-indol-3-yl)ethyl)amino)-2-chloro-5,8-dihydropyrido[3,4-d]pyrimidine-7(6H)-carboxylate (160 mg) and 5-fluoropyridine-3-boronic acid (90 mg) to give the desired product as a residue (85 mg, 46%).

UPLC-MS (acidic Method, 4 min): rt 2.16 min, m/z 489.2 [M+H]$^+$ $^1$H NMR (400 MHz, DMSO-d$_6$) δ ppm 10.83 (s, 1H), 9.33 (t, J=1.5 Hz, 1H), 8.68 (d, J=2.8 Hz, 1H), 8.24-8.38 (m, 1H), 7.60 (d, J=7.8 Hz, 1H), 7.34 (d, J=8.0 Hz, 1H), 7.30 (br s, 1H), 7.21 (d, J=2.3 Hz, 1H), 7.07 (td, J=7.5, 1.0 Hz, 1H), 6.92-7.00 (m, 1H), 4.41 (s, 2H), 3.74-3.87 (m, 2H), 3.65 (br t, J=5.4 Hz, 2H), 3.04 (t, J=7.5 Hz, 2H), 2.45 (br t, J=5.5 Hz, 2H), 1.35-1.54 (m, 9H).

Step 3 N-(2-(1H-indol-3-yl)ethyl)-2-(5-fluoropyridin-3-yl)-5,6,7,8-tetrahydropyrido[3,4-d]pyrimidin-4-amine 5N HCl in IPA (5 mL) was added to a solution of t-butyl 4-((2-(1H-indol-3-yl)ethyl)amino)-2-(5-fluoropyridin-3-yl)-5,8-dihydropyrido[3,4-d]pyrimidine-7(6H)-carboxylate (80 mg) in methanol (5 mL). The reaction mixture darkened in colour. After 18h the reaction mixture was evaporated. Loose SCX resin (1 g) was added followed by water (5 mL) and methanol (5 mL). Spin to mix for about 10 min, then load into a fritted tube and allow to drain. The SCX cartridge so formed was washed through with methanol/water [1:1] (10 mL), then methanol (2×10 mL). The product was eluted as the free base, eluting with 7M ammonia in methanol (20 mL). The free based material was evaporated, then triturated with diethyl ether and filtered to afford the desired product as a brown solid (35 mg, 54%). UPLC-MS (Basic Method, 4 min): rt 1.61 min, m/z 389.2 [M+H]$^+$ $^{19}$F NMR (400 MHz, DMSO-d$_6$) δ ppm −127.75 proton decoupled $^1$H NMR (400 MHz, DMSO-d$_6$) δ ppm 10.86 (s, 1H), 9.32 (t, J=1.5 Hz, 1H), 8.67 (d, J=3.0 Hz, 1H), 8.26-8.39 (m, 1H), 7.62 (d, J=8.0 Hz, 1H), 7.35 (d, J=8.0 Hz, 1H), 7.22 (d, J=2.0 Hz, 1H), 7.15 (br t, J=5.6 Hz, 1H), 7.05-7.10 (m, 1H), 6.91-7.01 (m, 1H), 3.74-3.85 (m, 2H), 3.72 (s, 2H), 2.90-3.09 (m, 4H), 2.75-2.85 (m, 1H), 2.33 (br t, J=5.5 Hz, 2H).

Example 9 Preparation of N-(2-(1H-indol-3-yl)ethyl)-2-(pyridin-3-yl)-5,6,7,8-tetrahydro pyrido[3,4-d]pyrimidin-4-amine

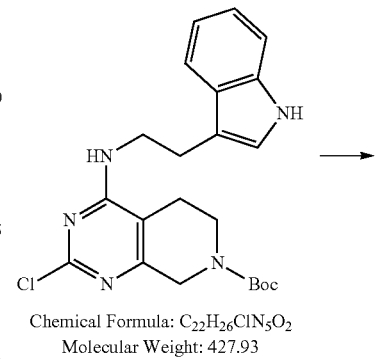

Chemical Formula: C$_{22}$H$_{26}$ClN$_5$O$_2$
Molecular Weight: 427.93

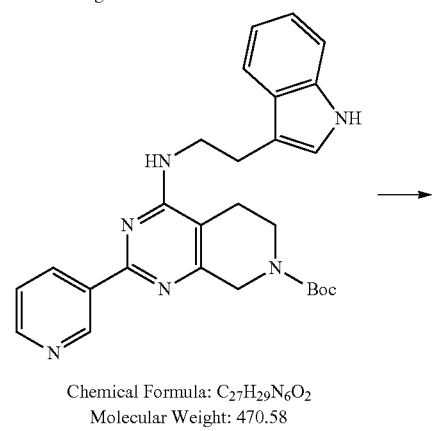

Chemical Formula: C$_{27}$H$_{29}$N$_6$O$_2$
Molecular Weight: 470.58

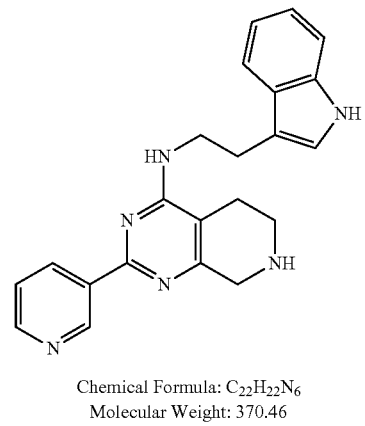

Chemical Formula: C$_{22}$H$_{22}$N$_6$
Molecular Weight: 370.46

Step 1 t-Butyl 4-((2-(1H-indol-3-yl)ethyl)amino)-2-(pyridin-3-yl)-5,8-dihydropyrido[3,4-d]pyrimidine-7(6H)-carboxylate Prepared according to general method B, using t-butyl 4-((2-(1H-indol-3-yl)ethyl)amino)-2-chloro-5,8-dihydropyrido[3,4-d]pyrimidine-7(6H)-carboxylate (200 mg) and pyridine-3-boronic acid (100 mg) to give the desired product as a residue (110 mg, 46%).

UPLC-MS (acidic Method, 2 min): rt 1.15 min, m/z 471.2 [M+H]$^+$ $^1$H NMR (400 MHz, DMSO-d$_6$) δ ppm 10.83 (s, 1H), 9.36-9.53 (m, 1H), 8.65 (dd, J=4.8, 1.8 Hz, 1H), 8.57 (dt, J=8.0, 1.9 Hz, 1H), 7.60 (d, J=8.0 Hz, 1H), 7.45-7.53 (m, 1H), 7.35 (d, J=8.3 Hz, 1H), 7.22 (d, J=2.3 Hz, 2H), 7.04-7.13 (m, 1H), 6.89-7.01 (m, 1H), 4.40 (s, 2H), 3.76-3.85 (m, 2H), 3.65 (br t, J=5.1 Hz, 2H), 3.05 (br t, J=7.5 Hz, 2H), 2.45 (br t, J=5.5 Hz, 2H), 1.37-1.53 (m, 9H).

Step 2 N-(2-(1H-indol-3-yl)ethyl)-2-(pyridin-3-yl)-5,6,7,8-tetrahydropyrido[3,4-d]pyrimidin-4-amine 5N HCl in IPA (3 mL) was added to a solution of t-butyl 4-((2-(1H-indol-3-yl)ethyl)amino)-2-(pyridin-3-yl)-5,8-dihydropyrido[3,4-d]pyrimidine-7(6H)-carboxylate (100 mg) in methanol (1m L). The reaction mixture darkened in colour. After 18 h the reaction mixture was evaporated. Loose SCX resin (1 g) was added followed by water (5 mL) and methanol (10 mL). Spin to mix for about 10 min, then load into a fritted tube and allow to drain. The SCX cartridge so formed was washed through with methanol/water [1:1] (10 mL), then methanol (2×10 mL). The product was eluted as the free base, eluting with 7M ammonia in methanol (20 mL). The free based material was evaporated, then triturated with diethyl ether and filtered to afford the desired product as a white solid (41 mg, 52%). UPLC-MS (Acidic Method, 4 min): rt 1.46 min, m/z 371.2 [M+H]$^+$ $^1$H NMR (400 MHz, DMSO-d$_6$) δ ppm 10.86 (s, 1H), 9.46 (dd, J=2.0, 0.8 Hz, 1H), 8.64 (dd, J=4.8, 1.8 Hz, 1H), 8.56 (dt, J=8.0, 1.9 Hz, 1H), 7.61 (d, J=7.8 Hz, 1H), 7.48 (ddd, J=8.0, 4.8, 0.8 Hz, 1H), 7.35 (d, J=8.0 Hz, 1H), 7.22 (d, J=2.3 Hz, 1H), 7.04-7.11 (m, 2H), 6.99 (td, J=7.5, 0.9 Hz, 1H), 3.74-3.84 (m, 2H), 3.72 (s, 2H), 2.95-3.09 (m, 5H), 2.33 (br t, J=4.6 Hz, 2H).

Example 10 Preparation of N-(2-(1H-indol-3-yl)ethyl)-2-(pyridin-3-yl)-6,7-dihydro-5H-pyrrolo[3,4-d]pyrimidin-4-amine

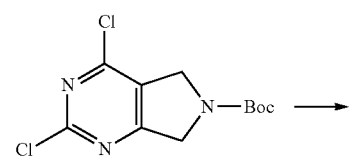

Chemical Formula: C$_{11}$H$_{13}$Cl$_3$N$_3$O$_2$
Molecular Weight: 290.14

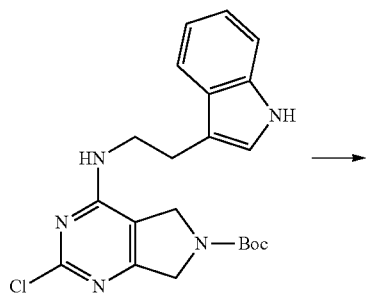

Chemical Formula: C$_{21}$H$_{24}$ClN$_5$O$_2$
Molecular Weight: 413.91

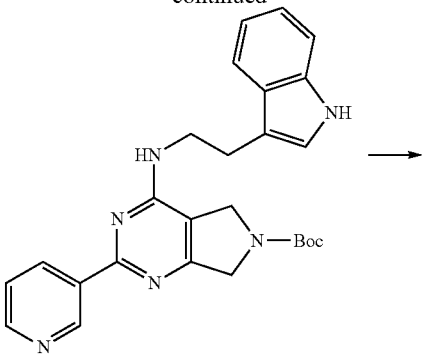

Chemical Formula: C$_{26}$H$_{28}$N$_6$O$_2$
Molecular Weight: 456.55

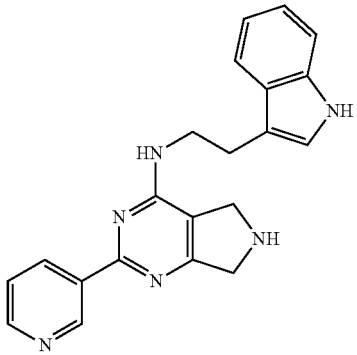

Chemical Formula: C$_{21}$H$_{20}$N$_6$
Molecular Weight: 356.43

Step 1 t-Butyl 4-((2-(1H-indol-3-yl)ethyl)amino)-2-chloro-5,7-dihydro-6H-pyrrolo[3,4-d]pyrimidine-6-carboxylate Prepared according to general method A, using t-butyl 2,4-dichloro-5,7-dihydro-6H-pyrrolo[3,4-d]pyrimidine-6-carboxylate (630 mg) and work up of evaporation, trituration with water, collect by filtration and dry in desiccator to give the desired product as a white solid (900 mg, quantitative). Agilent LC-MS (acidic fast 4 min pos): rt 2.26 min, m/z 414.2/416.2 [M+H]$^+$ $^1$H NMR (400 MHz, CHLOROFORM-d) δ ppm 8.05-8.33 (m, 1H), 7.64 (dd, J=7.9, 3.1 Hz, 1H), 7.35-7.50 (m, 1H), 7.25 (q, J=6.9 Hz, 1H), 7.12-7.20 (m, 1H), 7.06 (dd, J=15.2, 2.1 Hz, 1H), 4.74-4.87 (m, 1H), 4.42-4.57 (m, 2H), 4.18-4.33 (m, 2H), 3.73-3.92 (m, 2H), 3.05-3.15 (m, 2H), 1.51 (d, J=1.8 Hz, 9H).

Step 2 t-Butyl 4-((2-(1H-indol-3-yl)ethyl)amino)-2-(pyridin-3-yl)-5,7-dihydro-6H-pyrrolo[3,4-d]pyrimidine-6-carboxylate Prepared according to general method B, using t-butyl 4-((2-(1H-indol-3-yl)ethyl)amino)-2-chloro-5,7-dihydro-6H-pyrrolo[3,4-d]pyrimidine-6-carboxylate (130 mg) and pyridine-3-boronic acid (90 mg) to give the desired product as a white solid (100 mg, 68%).

UPLC-MS (acidic Method, 2 min): rt 1.08 min, m/z 457.2 [M+H]$^+$ $^1$H NMR (400 MHz, DMSO-d$_6$) δ ppm 10.83 (s, 1H), 9.46 (s, 1H), 8.66 (dd, J=4.8, 1.5 Hz, 1H), 8.56 (ddt, J=7.9, 3.9, 2.0 Hz, 1H), 7.63-7.72 (m, 1H), 7.59 (br d, J=7.8 Hz, 1H), 7.45-7.52 (m, 1H), 7.35 (d, J=8.0 Hz, 1H), 7.22 (d, J=2.3 Hz, 1H), 7.03-7.13 (m, 1H), 6.99 (td, J=7.4, 1.0 Hz, 1H), 4.45 (br dd, J=19.2, 12.9 Hz, 4H), 3.79 (q, J=6.4 Hz, 2H), 3.05 (t, J=7.4 Hz, 2H), 1.44-1.56 (m, 9H).

Step 3 N-(2-(1H-indol-3-yl)ethyl)-2-(pyridin-3-yl)-6,7-dihydro-5H-pyrrolo[3,4-d]pyrimidin-4-amine 5N HCl in IPA (5 mL) was added to a solution of t-butyl 4-((2-(1H-indol-3-yl)ethyl)amino)-2-(pyridin-3-yl)-5,7-dihydro-6H-pyrrolo[3,4-d]pyrimidine-6-carboxylate (70 mg) in methanol (3 mL). The reaction mixture darkened in colour, but still heterogeneous. DCM (3 mL) was added to aid solubility. After 18h the reaction mixture was evaporated, loaded onto a SCX resin cartridge (1 g) in methanol/water [1:1]. The SCX cartridge was washed through with methanol/water [1:1] (10 mL), then methanol (2×10 mL). The product was eluted as the free base, eluting with 7M ammonia in methanol (20 mL). The free based material was evaporated, then triturated with diethyl ether and filtered to afford the desired product as a white solid (30 mg, 55%).

UPLC-MS (Basic Method, 4 min): rt 1.40 min, m/z 357.2 [M+H]$^+$ $^1$H NMR (400 MHz, DMSO-d$_6$) δ ppm 10.83 (br s, 1H), 9.48 (dd, J=2.3, 0.8 Hz, 1H), 8.65 (dd, J=4.8, 1.8 Hz, 1H), 8.58 (dt, J=8.2, 1.8 Hz, 1H), 7.61 (d, J=7.8 Hz, 1H), 7.49 (ddd, J=7.8, 4.8, 0.9 Hz, 1H), 7.30-7.41 (m, 2H), 7.22 (d, J=2.3 Hz, 1H), 7.08 (td, J=7.5, 1.3 Hz, 1H), 6.99 (td, J=7.4, 1.0 Hz, 1H), 4.41-4.56 (m, 1H), 3.92-4.07 (m, 4H), 3.73-3.84 (m, 2H), 3.05 (t, J=7.5 Hz, 2H).

Example 11 Preparation of 4-(2-(1H-indol-3-yl)ethoxy)-2-(5-fluoropyridin-3-yl)-5,6,7,8-tetrahydropyrido[3,4-d]pyrimidine

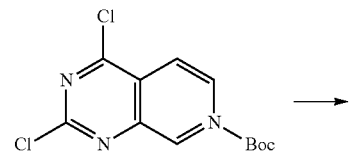

Chemical Formula: C$_{12}$H$_{15}$Cl$_2$N$_3$O$_2$
Molecular Weight: 304.17

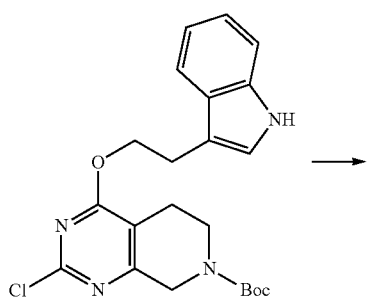

Chemical Formula: C$_{22}$H$_{25}$ClN$_4$O$_3$
Molecular Weight: 428.92

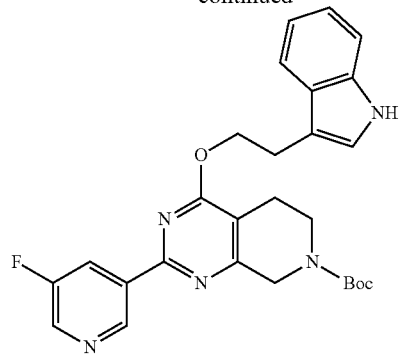

Chemical Formula: C$_{27}$H$_{28}$FN$_5$O$_3$
Molecular Weight: 489.55

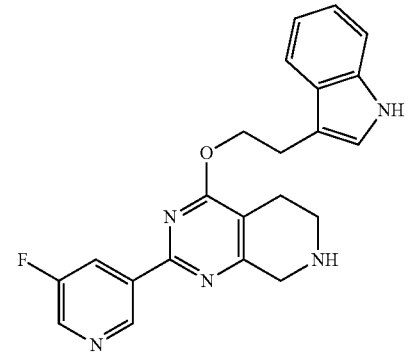

Chemical Formula: C$_{22}$H$_{22}$FN$_5$O
Molecular Weight: 389.43

Step 1 tert-butyl 4-(2-(1H-indol-3-yl)ethoxy)-2-chloro-5,8-dihydropyrido[3,4-d]pyrimidine-7(6H)-carboxylate 60% Sodium hydride in oil (70 mg, 1.6 equiv.) was added to a solution of tryptophol (210 mg, 1.1 equiv.) in THF (8 mL), observe gas evolution. After 10 minutes a solution of tert-butyl 2,4-dichloro-5,8-dihydropyrido[3,4-d]pyrimidine-7(6H)-carboxylate (360 mg) in THF (8 mL) was added. Stir at ambient temperature for 2 days. The reaction mixture was quenched with water and extracted into ethyl acetate. The organic phase was dried over sodium sulphate and then evaporated to give a slurry. Purification using Biotage (10 g cartridge) eluting with a gradient of MeOH (0-5%) in DCM, to afford the desired product as an orange gum (140 mg) in 1:3 mixture with tryptophol. UPLC-MS (Basic Method, 2 min): rt 1.33 min, m/z 429/431 [M+H]$^+$ $^1$H NMR (400 MHz, CDCl$_3$-d) δ ppm 8.16 (br s, 1H), 7.69 (d, J=7.3 Hz, 1H), 7.35-7.41 (m, 1H), 7.20-7.25 (m, 1H), 7.11-7.19 (m, 1H), 7.05-7.10 (m, 1H), 4.63-4.71 (m, 2H), 4.48-4.55 (m, 2H), 3.59-3.69 (m, 2H), 3.22-3.31 (m, 2H), 2.56-2.65 (m, 2H), 1.50 (s, 9H).

Step 2 tert-butyl 4-(2-(1H-indol-3-yl)ethoxy)-2-(5-fluoropyridin-3-yl)-5,8-dihydro pyrido[3,4-d]pyrimidine-7(6H)-carboxylate Prepared according to general method B, using tert-butyl 4-(2-(1H-indol-3-yl)ethoxy)-2-chloro-5,8-dihydropyrido[3,4-d]pyrimidine-7(6H)-carboxylate:tryptophol [1:3] (140 mg) and 5-fluoropyridine-3-boronic acid (80 mg) to give the desired product as a residue (20 mg, 26%).

UPLC-MS (acidic Method, 2 min): rt 1.38 min, m/z 490.3 [M+H]+

19F NMR (400 MHz, CDCl3-d) δ ppm −125.54 proton decoupled

1H NMR (400 MHz, CDCl3-d) δ ppm 9.39 (s, 1H), 8.57 (d, J=2.5 Hz, 1H), 8.53 (br d, J=9.3 Hz, 1H), 8.20 (br s, 1H), 7.66 (d, J=8.3 Hz, 1H), 7.37-7.41 (m, 1H), 7.21 (td, J=7.5, 1.3 Hz, 1H), 7.12-7.18 (m, 2H), 4.81 (t, J=6.8 Hz, 2H), 4.61 (s, 2H), 3.72 (t, J=5.8 Hz, 2H), 3.33 (t, J=6.7 Hz, 2H), 2.74 (br t, J=5.5 Hz, 2H), 1.54 (s, 9H).

Step 3 4-(2-(1H-indol-3-yl)ethoxy)-2-(5-fluoropyridin-3-yl)-5,6,7,8-tetrahydropyrido[3,4-d]pyrimidine Prepared according to general method C, using tert-butyl 4-(2-(1H-indol-3-yl)ethoxy)-2-(5-fluoropyridin-3-yl)-5,8-dihydropyrido[3,4-d]pyrimidine-7(6H)-carboxylate (20 mg) to give the desired product as a residue (16 mg, 100%).

UPLC-MS (acidic Method, 4 min): rt 1.35 min, m/z 390.2 [M+H]+

19F NMR (400 MHz, DMSO-d6) δ ppm −127.34 proton decoupled

1H NMR (400 MHz, DMSO-d6) δ ppm 10.88 (br s, 1H), 9.31 (t, J=1.6 Hz, 1H), 8.70 (d, J=2.9 Hz, 1H), 8.29-8.41 (m, 1H), 7.61 (d, J=7.9 Hz, 1H), 7.35 (d, J=8.2 Hz, 1H), 7.26 (d, J=2.3 Hz, 1H), 7.08 (td, J=7.5, 1.1 Hz, 1H), 6.99 (td, J=7.5, 1.0 Hz, 1H), 4.76 (t, J=6.9 Hz, 2H), 3.84 (s, 2H), 3.22 (t, J=6.9 Hz, 2H), 2.97 (t, J=5.8 Hz, 2H), 2.53 (br s, 2H). 1H exchangeable not seen.

Example 12 Preparation of 4-((2-(1H-indol-3-yl)ethyl)amino)-2-(5-fluoropyridin-3-yl)-N,N-dimethyl-5,8-dihydropyrido[3,4-d]pyrimidine-7(6H)-sulfonamide

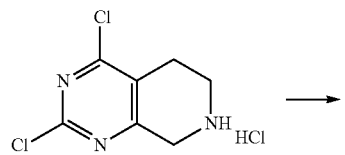

Chemical Formula: C7H8Cl3N3
Molecular Weight: 240.51

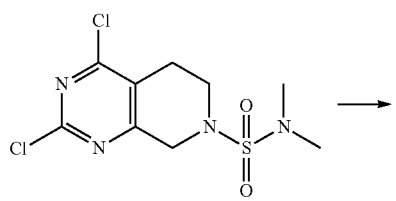

Chemical Formula: C9H12Cl2N4O2S
Molecular Weight: 311.18

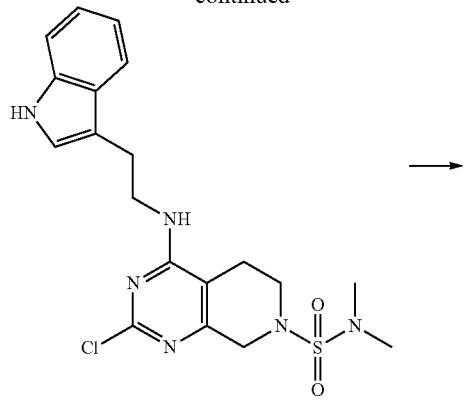

Chemical Formula: C19H23ClN6O2S
Molecular Weight: 434.94

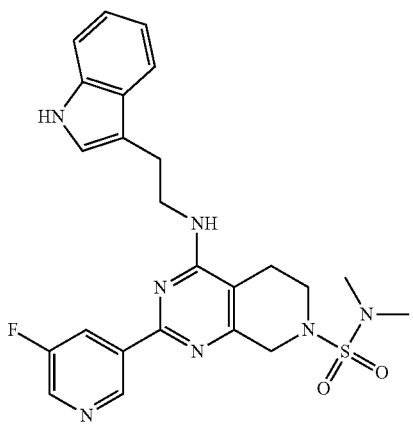

Chemical Formula: C24H26FN7O2S
Molecular Weight: 495.58

Step 1 2,4-dichloro-N,N-dimethyl-5,8-dihydropyrido[3,4-d]pyrimidine-7(6H)-sulfonamide Triethylamine (115 μL, 2 equiv.) was added to a suspension of 2,4-dichloro-5,6,7,8-tetrahydropyrido[3,4-d]pyrimidine hydrochloride (100 mg, 1 equiv.) in DCM (1 mL). After stirring for few minutes dimethylsulfamoyl chloride (70 μL, 1.5 equiv.) was added. The mixture became cloudy. After completion (reaction monitored by UPLC analysis), DCM was added followed by water. The organic phase was then dried over sodium sulfate, filtered and evaporated, to give the desired product as a solid (130 mg, 100%).

UPLC-MS (Acidic Method, 2 min): rt 0.93 min, m/z 311/313[M+H]+

1H NMR (400 MHz, CDCl3-d) δ ppm 4.39 (s, 2H), 3.57-3.64 (m, 2H), 2.90-2.95 (m, 2H), 2.86 (s, 6H).

Step 2 4-((2-(1H-indol-3-yl)ethyl)amino)-2-chloro-N,N-dimethyl-5,8-dihydropyrido[3,4-d]pyrimidine-7(6H)-sulfonamide Prepared according to general method A, using 2,4-dichloro-N,N-dimethyl-5,8-dihydropyrido[3,4-d]pyrimidine-7(6H)-sulfonamide (130 mg) to give the desired product after purification using Biotage (Telos column 10 g, Eluent Hexane-EtOAc 5 to 30 to 50%) as a white solid (107 mg, 59%) UPLC-MS (Acidic Method, 2 min): rt 1.03 min, m/z 435 [M+H]$^+$ $^1$H NMR (400 MHz, CDCl$_3$-d) δ ppm 8.04-8.22 (m, 1H), 7.60-7.65 (m, 1H), 7.38-7.44 (m, 1H), 7.21-7.26 (m, 1H), 7.11-7.17 (m, 1H), 7.05-7.08 (m, 1H), 4.79-4.88 (m, 1H), 4.19 (s, 2H), 3.81-3.89 (m, 2H), 3.48-3.54 (m, 2H), 3.07-3.14 (m, 2H), 2.84 (s, 6H), 2.17-2.25 (m, 2H)

Step 3 4-((2-(1H-indol-3-yl)ethyl)amino)-2-(5-fluoropyridin-3-yl)-N,N-dimethyl-5,8-dihydropyrido[3,4-d]pyrimidine-7(6H)-sulfonamide Prepared according to general method B, using 4-((2-(1H-indol-3-yl)ethyl)amino)-2-chloro-N,N-dimethyl-5,8-dihydropyrido[3,4-d]pyrimidine-7(6H)-sulfonamide (105 mg) and 5-fluoropyridine-3-boronic acid (60 mg) to give the desired product as a white solid (66 mg, 62%).

UPLC-MS (Acidic Method, 4 min): rt 1.71 min, m/z 496.2 [M+H]$^+$ $^{19}$F NMR (400 MHz, DMSO-d$_6$) δ ppm −127.63 proton decoupled $^1$H NMR (400 MHz, DMSO-d$_6$) δ ppm 10.83 (s, 1H), 9.33 (t, J=1.6 Hz, 1H), 8.68 (d, J=2.9 Hz, 1H), 8.26-8.44 (m, 1H), 7.60 (d, J=7.9 Hz, 1H), 7.29-7.41 (m, 2H), 7.22 (d, J=2.1 Hz, 1H), 7.08 (td, J=7.6, 1.1 Hz, 1H), 6.98 (td, J=7.4, 1.0 Hz, 1H), 4.27 (s, 2H), 3.73-3.87 (m, 2H), 3.58 (t, J=5.8 Hz, 2H), 3.05 (t, J=7.5 Hz, 2H), 2.77-2.86 (s, 6H), 2.52-2.56 (m, 2H)

Example 13 Preparation of 4-((2-(1H-indol-3-yl)ethyl)amino)-2-(5-fluoropyridin-3-yl)-N,N-dimethyl-5,8-dihydropyrido[3,4-d]pyrimidine-7(6H)-carboxamide

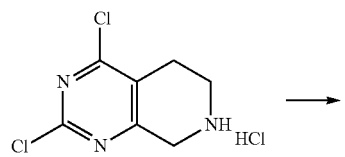

Chemical Formula: C$_7$H$_8$Cl$_3$N$_3$
Molecular Weight: 240.51

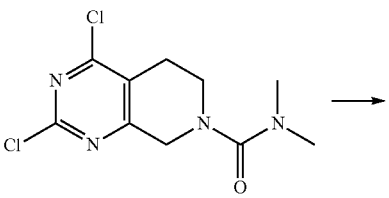

Chemical Formula: C$_{10}$H$_{12}$Cl$_2$N$_4$O
Molecular Weight: 275.13

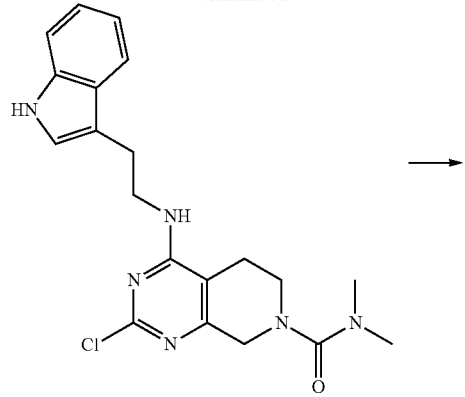

Chemical Formula: C$_{20}$H$_{23}$ClN$_6$O
Molecular Weight: 398.89

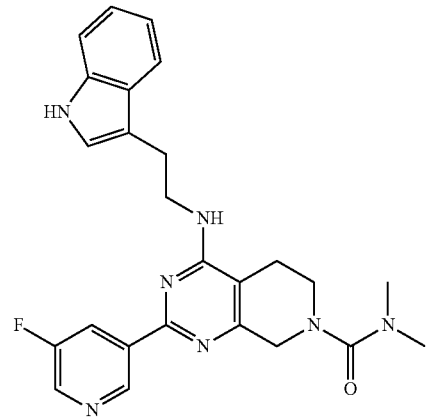

Chemical Formula: C$_{25}$H$_{26}$FN$_7$O
Molecular Weight: 459.53

Step 1 2,4-dichloro-N,N-dimethyl-5,8-dihydropyrido[3,4-d]pyrimidine-7(6H)-carboxamide Triethylamine (115 μL, 2 equiv.) was added to a suspension of 2,4-dichloro-5,6,7,8-tetrahydropyrido[3,4-d]pyrimidine hydrochloride (100 mg, 1 equiv.) in DCM (1 mL). After stirring for few minutes dimethyl carbamoyl chloride (80 μL, 1.5 equiv.) was added. The mixture became cloudy. After completion (reaction monitored by UPLC analysis), DCM was added followed by water. The organic phase was then dried over sodium sulfate, filtered and evaporated, to give the desired product as a pale orange oil (115 mg, 100%).

UPLC-MS (Acidic Method, 2 min): rt 0.84 min, m/z 275/277 [M+H]$^+$ $^1$H NMR (400 MHz, CDCl$_3$-d) δ ppm 4.42 (s, 2H), 3.53 (s, 2H), 2.88 (m, 8H).

Step 2 4-((2-(1H-indol-3-yl)ethyl)amino)-2-chloro-N,N-dimethyl-5,8-dihydropyrido[3,4-d]pyrimidine-7(6H)-carboxamide Prepared according to general method A, using 2,4-dichloro-N,N-dimethyl-5,8-dihydropyrido[3,4-d]pyrimidine-7(6H)-carboxamide (114 mg) to give the desired product after purification using Biotage (Telos column 4 g, Eluent Hexane-EtOAc 50 to 100%) as foam (137 mg, 83%)
UPLC-MS (Acidic Method, 2 min): rt 0.97 min, m/z 399/401 [M+H]⁺

¹H NMR (400 MHz, CDCl₃-d) δ ppm 7.99-8.20 (m, 1H), 7.61-7.67 (m, 1H), 7.36-7.43 (m, 1H), 7.19-7.26 (m, 1H), 7.10-7.17 (m, 1H), 7.03-7.08 (m, 1H), 4.25 (s, 1H), 3.84 (d, J=5.8 Hz, 1H), 3.58 (d, J=5.6 Hz, 1H), 3.42-3.48 (m, 1H), 3.07-3.13 (m, 1H), 2.97-3.03 (m, 1H), 2.80-2.87 (m, 6H), 2.19-2.25 (m, 1H), 1.23-1.30 (m, 1H).

Step 3 4-((2-(1H-indol-3-yl)ethyl)amino)-2-(5-fluoropyridin-3-yl)-N,N-dimethyl-5,8-dihydropyrido[3,4-d]pyrimidine-7(6H)-carboxamide Prepared according to general method B, using 4-((2-(1H-indol-3-yl)ethyl)amino)-2-chloro-N,N-dimethyl-5,8-dihydropyrido[3,4-d]pyrimidine-7(6H)-carboxamide (135 mg) and 5-fluoropyridine-3-boronic acid (60 mg) to give the desired product as a white solid (30 mg, 20%).

UPLC-MS (Acidic Method, 4 min): rt 1.44 min, m/z 460.3 [M+H]⁺

¹⁹F NMR (400 MHz, DMSO-d₆) δ ppm −127.71 proton decoupled

¹H NMR (400 MHz, DMSO-d₆) δ ppm 10.83 (s, 1H), 9.33 (t, J=1.6 Hz, 1H), 8.67 (d, J=2.9 Hz, 1H), 8.28-8.39 (m, 1H), 7.60 (d, J=7.8 Hz, 1H), 7.35 (d, J=8.0 Hz, 1H), 7.26 (t, J=5.7 Hz, 1H), 7.22 (d, J=2.3 Hz, 1H), 7.07 (td, J=7.6, 1.1 Hz, 1H), 6.94-7.03 (m, 1H), 4.22 (s, 2H), 3.75-3.87 (m, 2H), 3.46 (t, J=5.6 Hz, 2H), 3.04 (t, J=7.6 Hz, 2H), 2.81 (s, 6H) 2H under DMSO.

Example 14 Preparation of 4-((2-(1H-indol-3-yl)ethyl)amino)-2-(5-fluoropyridin-3-yl)-N-methyl-5,8-dihydropyrido[3,4-d]pyrimidine-7(6H)-carboxamide

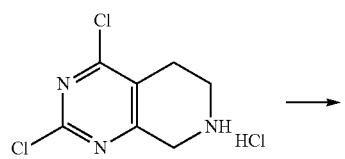

Chemical Formula: C₇H₈Cl₃N₃
Molecular Weight: 240.51

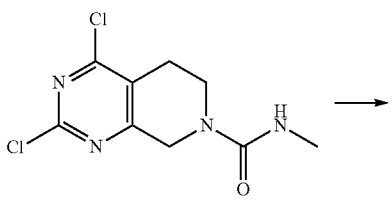

Chemical Formula: C₉H₁₀Cl₂N₄O
Molecular Weight: 261.11

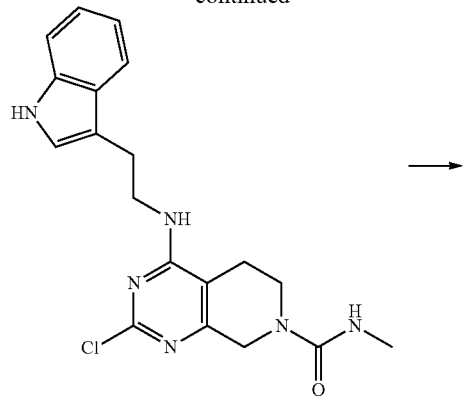

Chemical Formula: C₁₉H₂₁ClN₆O
Molecular Weight: 384.87

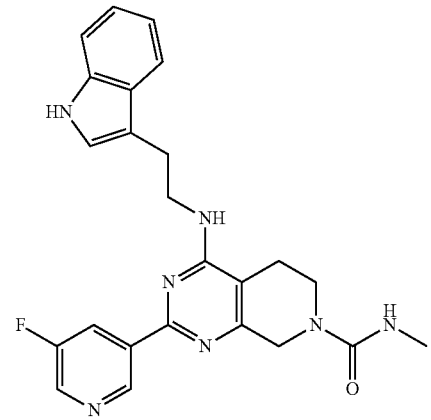

Chemical Formula: C₂₄H₂₄FN₇O
Molecular Weight: 445.50

Step 1 2,4-dichloro-N-methyl-5,8-dihydropyrido[3,4-d]pyrimidine-7(6H)-carboxamide Triethylamine (120 μL, 2 equiv.) was added to a suspension of 2,4-dichloro-5,6,7,8-tetrahydropyrido[3,4-d]pyrimidine hydrochloride (100 mg, 1 equiv.) in DCM (1 mL). After stirring for few minutes N-methylcarbamoyl chloride (40 mg, 1.5 equiv.) was added. The mixture became cloudy. After completion (reaction monitored by UPLC analysis), DCM was added followed by water. The organic phase was then dried over sodium sulfate, filtered and evaporated, to give the desired product as a pale yellow foam (98 mg, 91%).

UPLC-MS (Acidic Method, 2 min): rt 0.75 min, m/z 261/263 [M+H]⁺

¹H NMR (400 MHz, CDCl₃-d) δ ppm 4.69-4.80 (m, 1H), 4.57 (s, 2H), 3.73 (s, 2H), 2.85 (d, J=4.5 Hz, 5H).

Step 2 4-((2-(1H-indol-3-yl)ethyl)amino)-2-chloro-N-methyl-5,8-dihydropyrido[3,4-d]pyrimidine-7(6H)-carboxamide Prepared according to general method A, using 2,4-dichloro-N-methyl-5,8-dihydropyrido[3,4-d]pyrimidine-7(6H)-carboxamide (98 mg) to give the desired product after purification using Biotage (Telos column 10 g, Eluent DCM-MeOH 0 to 5 to 20%), followed by trituration in DCM as a solid (74 mg, 51%). UPLC-MS (Acidic Method, 2 min): rt 0.91 min, m/z 385 [M+H]⁺

¹H NMR (400 MHz, DMSO-d₆) δ ppm 10.74-10.87 (m, 1H), 7.61-7.68 (m, 1H), 7.45-7.54 (m, 1H), 7.31-7.36 (m, 1H), 7.14-7.21 (m, 1H), 7.02-7.10 (m, 1H), 6.94-7.01 (m, 1H), 6.58-6.68 (m, 1H), 4.18-4.30 (m, 2H), 3.49-3.66 (m, 4H), 2.89-3.00 (m, 2H), 2.56-2.63 (m, 3H), 2.27-2.36 (m, 2H).

Step 3 4-((2-(1H-indol-3-yl)ethyl)amino)-2-(5-fluoropyridin-3-yl)-N-methyl-5,8-dihydropyrido[3,4-d]pyrimidine-7(6H)-carboxamide Prepared according to general method B, using 4-((2-(1H-indol-3-yl)ethyl)amino)-2-chloro-N-methyl-5,8-dihydropyrido[3,4-d]pyrimidine-7(6H)-carboxamide (70 mg) and 5-fluoropyridine-3-boronic acid (50 mg) to give the desired product as an off-white solid (48 mg, 62%).

UPLC-MS (Acidic Method, 4 min): rt 1.44 min, m/z 446.3 [M+H]⁺

¹⁹F NMR (400 MHz, DMSO-d₆) δ ppm −127.64 proton decoupled

¹H NMR (400 MHz, DMSO-d₆) δ ppm 10.83 (s, 1H), 9.33 (t, J=1.6 Hz, 1H), 8.68 (d, J=2.9 Hz, 1H), 8.26-8.41 (m, 1H), 7.60 (d, J=7.8 Hz, 1H), 7.34 (d, J=8.0 Hz, 1H), 7.28 (t, J=5.6 Hz, 1H), 7.21 (d, J=2.3 Hz, 1H), 7.07 (td, J=7.6, 1.1 Hz, 1H), 6.97 (td, J=7.4, 1.0 Hz, 1H), 6.68 (q, J=3.9 Hz, 1H), 4.39 (s, 2H), 3.73-3.87 (m, 2H), 3.63 (t, J=5.6 Hz, 2H), 3.04 (t, J=7.5 Hz, 2H), 2.61 (d, J=4.4 Hz, 3H), 2.42 (br t, J=5.5 Hz, 2H).

Example 15 Preparation of (4-((2-(1H-indol-3-yl)ethyl)amino)-2-(5-fluoropyridin-3-yl)-5,8-dihydropyrido[3,4-d]pyrimidin-7(6H)-yl)(1-methyl-1H-pyrazol-5-yl)methanone

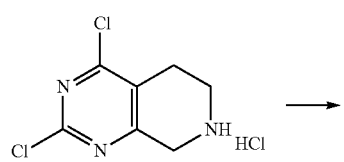

Chemical Formula: C₇H₈Cl₃N₃
Molecular Weight: 240.51

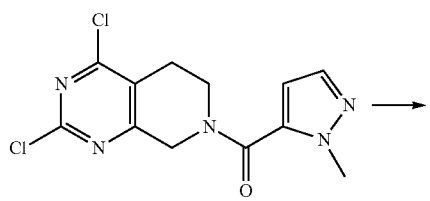

Chemical Formula: C₁₂H₁₁Cl₂N₅O
Molecular Weight: 312.15

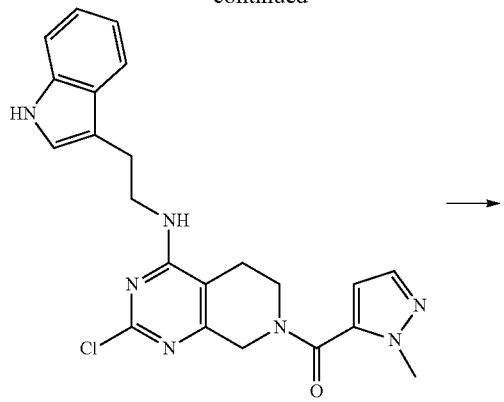

Chemical Formula: C₂₂H₂₂ClN₇O
Molecular Weight: 435.92

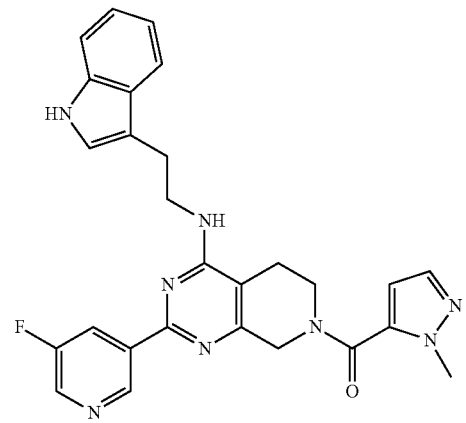

Chemical Formula: C₂₇H₂₅FN₈O
Molecular Weight: 496.55

Step 1 (2,4-dichloro-5,8-dihydropyrido[3,4-d]pyrimidin-7(6H)-yl)(1-methyl-1H-pyrazol-5-yl)methanone A suspension of 2-methyl-2H-pyrazole-3-carboxylic acid (105 mg, 1 equiv.), CDI (200 mg, 1.5 equiv) in DCM (10 mL) was stirred for 1 hour at ambient temperature under N₂ atmosphere. Then, 2,4-dichloro-5,6,7,8-tetrahydropyrido[3,4-d]pyrimidine hydrochloride (200 mg, 1 equiv.) and triethylamine (175 µL, 1.5 equiv.) were added and the reaction mixture was stirred overnight. After completion (reaction monitored by UPLC analysis), DCM was added followed by water. The organic phase was then dried over sodium sulfate, filtered and evaporated, to give the desired product after purification using Biotage (Telos column 10 g, Eluent DCM-MeOH 0 to 5%) as a white solid (208 mg, taken on as crude product). Two peaks were seen by UPLC with same mass UPLC-MS (Acidic Method, 2 min): rt 0.84 and 0.88 min, m/z 312/314 [M+H]⁺

¹H NMR (400 MHz, CDCl₃-d) δ ppm

Step 2 (4-((2-(1H-indol-3-yl)ethyl)amino)-2-chloro-5,8-dihydropyrido[3,4-d]pyrimidin-7(6H)-yl)(1-methyl-1H-pyrazol-5-yl)methanone Prepared according to general method A, using (2,4-dichloro-5,8-dihydropyrido[3,4-d]pyrimidin-7(6H)-yl)(1- methyl-1H-pyrazol-5-yl)methanone (200 mg) to give the desired product after purification using Biotage (Telos column 10 g, Eluent DCM-MeOH 0 to 5%) as a yellow foam (150 mg, taken on as crude product). UPLC-MS (Acidic Method, 2 min): rt 0.96 min, m/z 436 [M+H]$^+$ $^1$H NMR (400 MHz, CDCl$_3$-d) δ ppm 8.32 (br s, 1H), 7.56-7.63 (m, 1H), 7.44-7.52 (m, 1H), 7.36-7.42 (m, 1H), 7.18-7.25 (m, 1H), 7.08-7.16 (m, 1H), 7.04-7.08 (m, 1H), 4.59-4.76 (m, 2H), 3.75-4.05 (m, 7H), 3.04-3.15 (m, 2H), 2.12-2.37 (m, 2H) 2H exchangeable not seen Step 3 (4-((2-(1H-indol-3-yl)ethyl)amino)-2-(5-fluoropyridin-3-yl)-5,8-dihydro pyrido[3,4-d]pyrimidin-7(6H)-yl)(1-methyl-1H-pyrazol-5-yl) methanone Prepared according to general method B, using (4-((2-(1H-indol-3-yl)ethyl)amino)-2-chloro-5,8-dihydropyrido[3,4-d]pyrimidin-7(6H)-yl)(1-methyl-1H-pyrazol-5-yl)methanone (150 mg) and 5-fluoropyridine-3-boronic acid (90 mg). It was isolated and put back on 3 times to achieve complete conversion, to give the desired product as a white solid (6 mg, 4%).

UPLC-MS (Acidic Method, 4 min): rt 1.69 min, m/z 497.3 [M+H]$^+$ $^{19}$F NMR (400 MHz, DMSO-d$_6$) δ ppm −127.62 proton decoupled $^1$H NMR (400 MHz, DMSO-d$_6$) δ ppm 10.84 (s, 1H), 9.23-9.40 (m, 1H), 8.68 (br s, 1H), 8.25-8.42 (m, 1H), 7.60 (d, J=7.9 Hz, 1H), 7.54 (d, J=1.8 Hz, 1H), 7.29-7.43 (m, 2H), 7.23 (d, J=2.3 Hz, 1H), 7.04-7.10 (m, 1H), 6.95-7.01 (m, 1H), 6.54-6.68 (m, 1H), 4.56-4.76 (m, 2H), 3.71-4.01 (m, 7H), 3.05 (br t, J=7.5 Hz, 2H), 2.56 (br s, 2H).

Example 16 Preparation of 1-(4-((2-(1H-indol-3-yl)ethyl)amino)-2-(5-fluoropyridin-3-yl)-5,8-dihydropyrido[3,4-d]pyrimidin-7(6H)-yl)-2-aminoethan-1-one

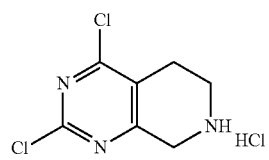

Chemical Formula: C$_7$H$_8$Cl$_3$N$_3$
Molecular Weight: 240.51

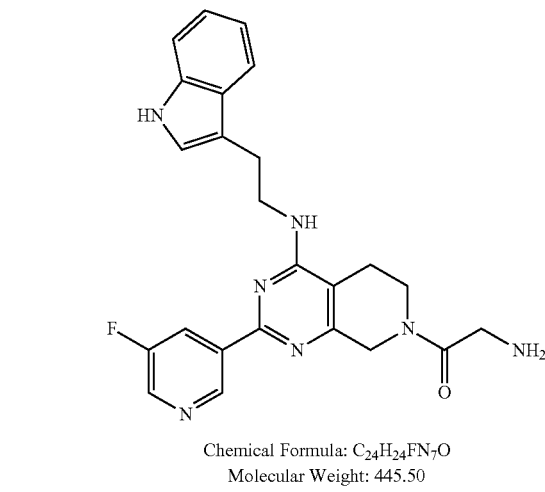 [SMILES: NCC(=O)N1CCc2c(nc(-c3cncc(F)c3)nc2NCCc2c[nH]c3ccccc23)C1]

Chemical Formula: C$_{14}$H$_{18}$Cl$_2$N$_4$O$_3$
Molecular Weight: 361.22

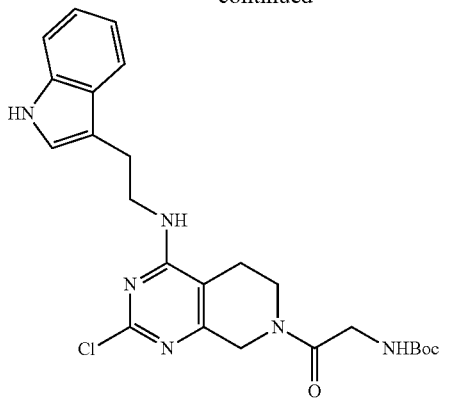

Chemical Formula: C$_{24}$H$_{29}$ClN$_6$O$_3$
Molecular Weight: 484.99

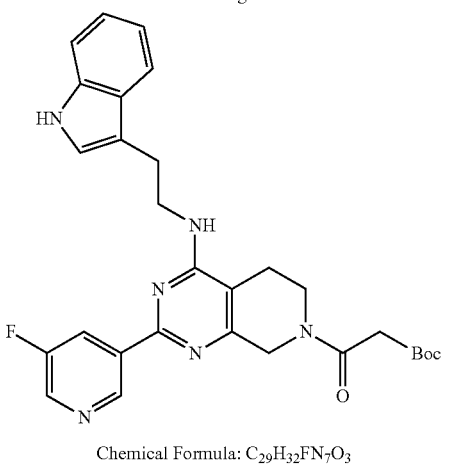

Chemical Formula: C$_{29}$H$_{32}$FN$_7$O$_3$
Molecular Weight: 545.62

Chemical Formula: C$_{24}$H$_{24}$FN$_7$O
Molecular Weight: 445.50

Step 1 tert-butyl (2-(2,4-dichloro-5,8-dihydropyrido[3,4-d]pyrimidin-7(6H)-yl)-2-oxoethyl)carbamate A reacti-vial was charged with 2,4-dichloro-5,6,7,8-tetrahydropyrido[3,4-d]pyrimidine hydrochloride (200 mg, 1 equiv.), BocGlyOH (146 mg, 1 equiv.), Et$_3$N (120 μL, 1.1 equiv.) and DCM (4 mL). To this suspension was added slowly T3P (50% in EtOAc) (500 μL, 2 equiv.) and the reaction mixture was heated at 40° C. After completion (reaction monitored by UPLC analysis), EtOAc was added followed by water. The organic phase was then washed with brine and dried over sodium sulphate, filtered and evaporated, to give the desired product as a yellow foam (415 mg, 92%). The product was used in the next stage without any further purification UPLC-MS (Acidic Method, 2 min): rt 1.03 min, m/z 305/307 (-tBu) 261 (-Boc) [M+H]+

$^{1}$H NMR (400 MHz, CDCl$_3$-d) δ ppm 5.34-5.52 (m, 1H), 4.83 (s, 1H), 4.61 (s, 1H), 3.88-4.12 (m, 3H), 3.67-3.81 (m, 1H), 2.80-2.99 (m, 2H), 1.44-1.48 (m, 9H)

Step 2 tert-butyl (2-(4-((2-(1H-indol-3-yl)ethyl)amino)-2-chloro-5,8-dihydropyrido [3,4-d]pyrimidin-7(6H)-yl)-2-oxoethyl)carbamate Prepared according to general method A, using tert-butyl (2-(2,4-dichloro-5,8-dihydropyrido[3,4-d]pyrimidin-7(6H)-yl)-2-oxoethyl)carbamate (415 mg) to give the desired product after purification using Biotage (Telos column 20 g, Eluent DCM-MeOH 0 to 5%) as a yellow foam (246 mg). Another batch (236) containing the product and the corresponding regioisomer (20%) was also isolated. UPLC-MS (Acidic Method, 2 min): rt 1.10 min, m/z 485/487 [M+H]+

$^{1}$H NMR (400 MHz, CDCl$_3$-d) δ ppm 8.11-8.27 (m, 1H), 7.54-7.65 (m, 1H), 7.40 (br d, J=8.2 Hz, 1H), 7.23 (s, 1H), 7.09-7.17 (m, 1H), 7.06 (d, J=2.0 Hz, 1H), 5.32-5.57 (m, 1H), 4.72-4.94 (m, 1H), 4.59 (s, 1H), 4.35 (s, 1H), 3.93-4.04 (m, 2H), 3.74-3.90 (m, 3H), 3.49-3.59 (m, 1H), 3.10 (s, 2H), 2.13 (s, 2H), 1.46 (s, 9H).

Step 3 tert-butyl (2-(4-((2-(1H-indol-3-yl)ethyl)amino)-2-(5-fluoropyridin-3-yl)-5,8-dihydropyrido[3,4-d]pyrimidin-7(6H)-yl)-2-oxoethyl)carbamate Prepared according to general method B, using tert-butyl (2-(4-((2-(1H-indol-3-yl)ethyl)amino)-2-chloro-5,8-dihydropyrido[3,4-d]pyrimidin-7(6H)-yl)-2-oxoethyl)carbamate (240 mg) and 5-fluoropyridine-3-boronic acid (140 mg). To give the desired product as a tan solid (170 mg, 62%).

UPLC-MS (Acidic Method, 2 min): rt 1.83 min, m/z 546.2 [M+H]+

$^{19}$F NMR (400 MHz, DMSO-d$_6$) δ ppm −127.64 proton decoupled $^{1}$H NMR (400 MHz, DMSO-d$_6$) δ ppm 10.78-10.87 (m, 1H), 9.30-9.35 (m, 1H), 8.64-8.70 (m, 1H), 8.28-8.36 (m, 1H), 7.58 (s, 1H), 7.34 (d, J=8.0 Hz, 2H), 7.21 (d, J=2.3 Hz, 1H), 7.07 (s, 1H), 6.93-7.00 (m, 1H), 6.78-6.88 (m, 1H), 4.51 (br s, 2H), 3.86-3.98 (m, 2H), 3.71-3.85 (m, 4H), 3.34-3.44 (m, 2H), 2.99-3.09 (m, 2H), 1.39 (s, 9H)

Step 4 1-(4-((2-(1H-indol-3-yl)ethyl)amino)-2-(5-fluoropyridin-3-yl)-5,8-dihydropyrido[3,4-d]pyrimidin-7(6H)-yl)-2-aminoethan-1-one Prepared according to general method C, using tert-butyl (2-(4-((2-(1H-indol-3-yl)ethyl)amino)-2-(5-fluoropyridin-3-yl)-5,8-dihydropyrido[3,4-d]pyrimidin-7(6H)-yl)-2-oxoethyl)carbamate (160 mg) to give the desired product as a residue (58 mg, 50%).

UPLC-MS (acidic Method, 4 min): rt 1.25 min, m/z 446.3 [M+H]+

$^{19}$F NMR (400 MHz, DMSO-d$_6$) δ ppm −127.64 proton decoupled $^{1}$H NMR (400 MHz, DMSO-d$_6$) δ ppm 10.75-10.90 (m, 1H), 9.28-9.38 (m, 1H), 8.62-8.71 (m, 1H), 8.27-8.38 (m, 1H), 7.54-7.63 (m, 1H), 7.26-7.39 (m, 2H), 7.17-7.24 (m, 1H), 7.02-7.11 (m, 1H), 6.92-7.00 (m, 1H), 4.53 (br s, 2H), 3.62-3.85 (m, 4H), 3.41-3.53 (m, 2H), 2.98-3.08 (m, 2H), 2.37-2.46 (m, 1H), 1.64-1.94 (m, 2H) 1H exchangeable not seen.

Example 17 Preparation of both N-(2-(1H-indol-3-yl)ethyl)-2-(5-fluoropyridin-3-yl)-6,7,8,9-tetrahydro-5H-pyrimido[4,5-d]azepin-4-amine (Example 17a) and N-(2-(1H-indol-3-yl)ethyl)-7-ethyl-2-(5-fluoropyridin-3-yl)-6,7,8,9-tetrahydro-5H-pyrimido[4,5-d]azepin-4-amine (Example 17b)

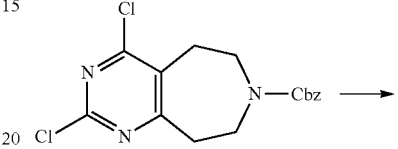

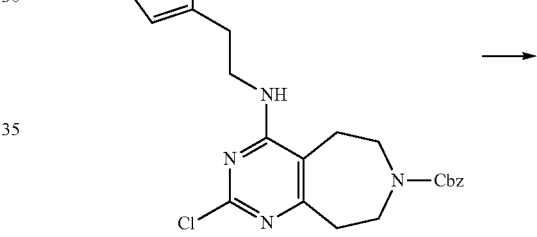

Chemical Formula: C$_{26}$H$_{26}$ClN$_5$O$_2$
Molecular Weight: 475.98

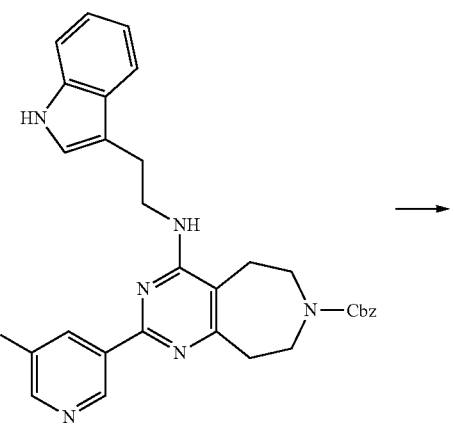

Chemical Formula: C$_{31}$H$_{29}$FN$_6$O$_2$
Molecular Weight: 536.61

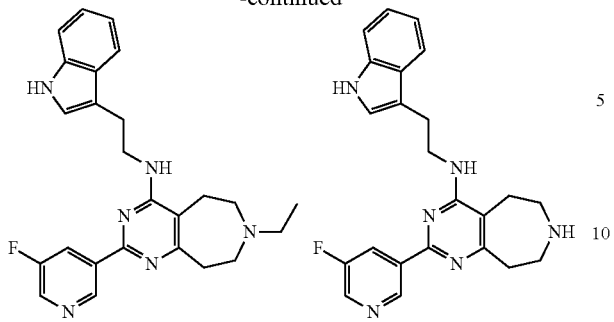

Chemical Formula: C$_{25}$H$_{27}$FN$_6$
Molecular Weight: 430.53
17b

Chemical Formula: C$_{23}$H$_{23}$FN$_6$
Molecular Weight: 402.48
17a

Step 1 benzyl 4-((2-(1H-indol-3-yl)ethyl)amino)-2-chloro-5,6,8,9-tetrahydro-7H-pyrimido[4,5-d]azepine-7-carboxylate Prepared according to general method A, using benzyl 2,4-dichloro-5,6,8,9-tetrahydro-7H-pyrimido[4,5-d]azepine-7-carboxylate (270 mg) to give the desired product and corresponding regioisomer after purification using Biotage (Telos column 10 g, Eluent Hexane-EtOAc 10 to 50 to 70%) as a white solid (227 mg, taken on as crude product).

UPLC-MS (Acidic Method, 2 min): rt 1.12 (78%) and 1.19 (21%) min, m/z 476/478 [M+H]$^+$
$^1$H NMR (400 MHz, DMSO-d6) δ ppm 10.72-10.86 (m, 1H), 7.59-7.70 (m, 1H), 7.42-7.54 (m, 1H), 7.25-7.41 (m, 6H), 7.13-7.20 (m, 1H), 7.02-7.10 (m, 1H), 6.93-7.02 (m, 1H), 5.10 (s, 2H), 3.46-3.69 (m, 6H), 2.85-3.01 (m, 4H), 2.62-2.73 (m, 2H)

Step 2 benzyl 4-((2-(1H-indol-3-yl)ethyl)amino)-2-(5-fluoropyridin-3-yl)-5,6,8,9-tetrahydro-7H-pyrimido[4,5-d]azepine-7-carboxylate Prepared according to general method B, using benzyl 4-((2-(1H-indol-3-yl)ethyl)amino)-2-chloro-5,6,8,9-tetrahydro-7H-pyrimido[4,5-d]azepine-7-carboxylate (227 mg) to give the desired product as a dry film (80 mg, 30%). UPLC-MS (Acidic Method, 2 min): rt 1.12 min, m/z 537.2 [M+H]$^+$
$^1$H NMR (400 MHz, CDCl$_3$-d) δ ppm: 9.42 (br s, 1H), 8.52-8.69 (m, 1H), 8.14-9.00 (m, 3H), 7.51-7.68 (m, 1H), 7.31-7.47 (m, 7H), 7.00-7.26 (m, 3H), 5.06-5.29 (m, 2H), 3.95-4.09 (m, 2H), 3.76-3.93 (m, 2H), 3.40-3.91 (m, 4H), 3.12-3.30 (m, 2H), 2.45-2.70 (m, 2H)

Step 3 N-(2-(1H-indol-3-yl)ethyl)-7-ethyl-2-(5-fluoropyridin-3-yl)-6,7,8,9-tetrahydro-5H-pyrimido[4,5-d]azepin-4-amine and N-(2-(1H-indol-3-yl)ethyl)-2-(5-fluoropyridin-3-yl)-6,7,8,9-tetrahydro-5H-pyrimido[4,5-d]azepin-4-amine A slurry of 10% palladium on carbon (20 mg) in ethanol (2 mL) was added, under nitrogen to a solution of benzyl 4-((2-(1H-indol-3-yl)ethyl)amino)-2-(5-fluoropyridin-3-yl)-5,6,8,9-tetrahydro-7H-pyrimido[4,5-d]azepine-7-carboxylate (60 mg) in THF (2 mL) and ethanol (8 mL). The mixture was hydrogenated at 1 atm for 24 hours. The catalyst was filtered off through a celite plug and washed through with further ethanol. The filtrate was evaporated to a minimal volume and was loaded directly onto a SCX cartridge (0.5 g) under gravity. The cartridge was washed with methanol (10 mL) and then eluted with 7M ammonia in methanol (10 mL). The elute fraction was evaporated. Purification on silica (4 g cartridge), eluting with a gradient of 7M ammonia in methanol (0-10%) in DCM, afforded N-(2-(1H-indol-3-yl)ethyl)-2-(5-fluoropyridin-3-yl)-6,7,8,9-tetrahydro-5H-pyrimido[4,5-d]azepin-4-amine (8 mg, 18%) and N-(2-(1H-indol-3-yl)ethyl)-7-ethyl-2-(5-fluoropyridin-3-yl)-6,7,8,9-tetrahydro-5H-pyrimido[4,5-d]azepin-4-amine (18 mg, 40%).

Data for N-(2-(1H-indol-3-yl)ethyl)-2-(5-fluoropyridin-3-yl)-6,7,8,9-tetrahydro-5H-pyrimido[4,5-d]azepin-4-amine (Example 17a)

UPLC-MS (Acidic Method, 4 min): rt 1.20 min, m/z 403.3 [M+H]$^+$
$^{19}$F NMR (400 MHz, DMSO-d$_6$) δ ppm −127.80 proton decoupled
$^1$H NMR (400 MHz, DMSO-d6) δ ppm: 10.83 (br s, 1H), 9.34 (t, J=1.6 Hz, 1H), 8.66 (d, J=2.9 Hz, 1H), 8.26-8.41 (m, 1H), 7.59 (d, J=7.9 Hz, 1H), 7.35 (d, J=8.0 Hz, 1H), 7.24 (t, J=5.5 Hz, 1H), 7.20 (d, J=2.3 Hz, 1H), 7.04-7.11 (m, 1H), 6.92-7.02 (m, 1H), 3.69-3.81 (m, 2H), 2.99-3.09 (m, 2H), 2.92-2.99 (m, 2H), 2.82-2.89 (m, 2H), 2.70-2.81 (m, 4H) (1H exchangeable not seen).

Data for N-(2-(1H-indol-3-yl)ethyl)-7-ethyl-2-(5-fluoropyridin-3-yl)-6,7,8,9-tetrahydro-5H-pyrimido[4,5-d]azepin-4-amine (Example 17b)

UPLC-MS (Acidic Method, 4 min): rt 1.25 min, m/z 431.3 [M+H]$^+$
$^{19}$F NMR (400 MHz, DMSO-d$_6$) δ ppm −127.78 proton decoupled
$^1$H NMR (400 MHz, DMSO-d6) δ ppm: 10.83 (s, 1H), 9.34 (t, J=1.6 Hz, 1H), 8.66 (d, J=2.9 Hz, 1H), 8.26-8.39 (m, 1H), 7.58 (d, J=7.9 Hz, 1H), 7.34 (d, J=8.0 Hz, 1H), 7.29 (t, J=5.5 Hz, 1H), 7.20 (d, J=2.1 Hz, 1H), 7.07 (td, J=7.5, 1.1 Hz, 1H), 6.93-7.03 (m, 1H), 3.66-3.85 (m, 2H), 2.99-3.08 (m, 2H), 2.91-2.99 (m, 2H), 2.70-2.79 (m, 2H), 2.57-2.66 (m, 2H), 2.53 (br d, J=3.4 Hz, 2H), 2.49 (br s, 2H), 1.03 (t, J=7.2 Hz, 3H)
$^{19}$F NMR (400 MHz, CDCl$_3$-d) δ ppm −127.82 proton decoupled
$^1$H NMR (CDCl$_3$-d) δ ppm: 9.46 (t, J=1.6 Hz, 1H), 8.55 (d, J=2.9 Hz, 1H), 8.35-8.42 (m, 1H), 8.22 (br s, 1H), 7.60 (d, J=7.9 Hz, 1H), 7.42 (d, J=8.2 Hz, 1H), 7.23 (td, J=7.6, 1.1 Hz, 1H), 7.05-7.16 (m, 2H), 5.09 (br s, 1H), 3.96 (q, J=6.4 Hz, 2H), 2.54-3.47 (m, 12H), 1.23-1.51 (m, 3H).

Example 18 Preparation of N-(2-(1H-indol-3-yl)ethyl)-7-benzyl-2-(5-fluoropyridin-3-yl)-8,8-dimethyl-5,6,7,8-tetrahydropyrido[3,4-d]pyrimidin-4-amine (Example 18a) and N-(2-(1H-indol-3-yl)ethyl)-2-(5-fluoropyridin-3-yl)-8,8-dimethyl-5,6,7,8-tetrahydropyrido[3,4-d]pyrimidin-4-amine (Example 18b)

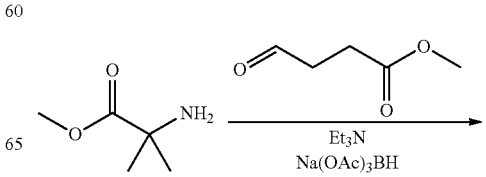

-continued

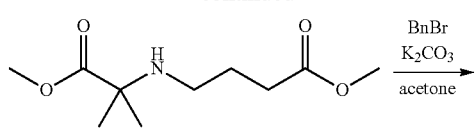

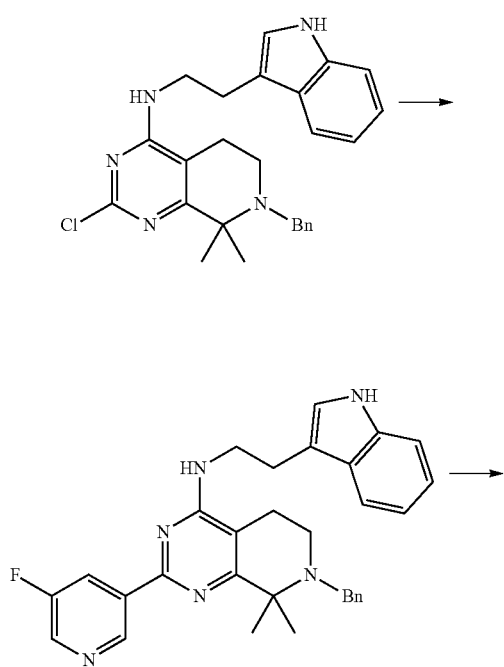

-continued

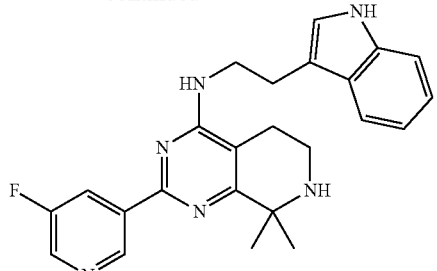

Chemical Formula: $C_{24}H_{25}FN_6$
Molecular Weight: 416.50

Step 1: Methyl 4-((1-methoxy-2-methyl-1-oxopropan-2-yl)amino)butanoate

A solution of methyl 2-amino-2-methylpropanoate (500 mg, 3.25 mmol) in dichloroethane was stirred at room temperature, then triethylamine (1.6 equiv., 5.2 mmol), Na(OAc)$_3$BH (2.5 equiv., 8.1 mmol) and Methyl 4-oxobutanoate (0.9 equiv., 2.9 mmol) were added under N$_2$ and the resulting mixture was stirred at room temperature for 18 h. The reaction mixture was quenched with NaHCO$_3$ solution for 30 minutes then aqueous solution was extracted twice with DCM. The organic solution was dried over Na$_2$SO$_4$ and evaporated under reduced pressure. The crude was purified by column chromatography on silica gel using ethyl acetate in hexane as mobile phase to give Methyl 4-((1-methoxy-2-methyl-1-oxopropan-2-yl)amino)butanoate (0.466 g, 74%) as a yellowish oil. UPLC-MS (Basic Method, 2 min): rt 0.84 min, m/z 218.2 [M+H]$^+$ $^1$H NMR (DMSO-d6) δ ppm: 3.60 (s, 3H), 3.57 (s, 3H), 2.29-2.39 (m, 4H), 1.54-1.64 (m, 2H), 1.17 (t, J=7.0 Hz, 6H)

Step 2: Methyl 4-(benzyl(1-methoxy-2-methyl-1-oxopropan-2-yl)amino)butanoate

A solution of Methyl 4-((1-methoxy-2-methyl-1-oxopropan-2-yl)amino)butanoate (466 mg, 2.15 mmol) in acetone was stirred and degassed at room temperature under N$_2$ then potassium carbonate (1.2 equiv., 2.6 mmol) and benzyl bromide (1.5 equiv., 3.2 mmol) were added and the resulting mixture was stirred at 70° C. for 72 h. The solvent was evaporated under reduced pressure and the residue was diluted in water and extracted twice with EtOAc. The organic solution was washed with brine, dried over Na$_2$SO$_4$ and evaporated under reduced pressure. The crude was purified by column chromatography on silica gel using ethyl acetate in hexane as mobile phase to give Methyl 4-(benzyl (1-methoxy-2-methyl-1-oxopropan-2-yl)amino)butanoate (0.59 g, 89%) as a yellowish oil. UPLC-MS (Basic Method, 2 min): rt 1.26 min, m/z 308.1 [M+H]$^+$ $^1$H NMR (400 MHz, DMSO-d6) δ ppm: 7.32-7.38 (m, 2H), 7.29 (t, J=7.6 Hz, 2H), 7.18 (s, 1H), 3.74 (s, 2H), 3.63 (s, 3H), 3.51 (s, 3H), 2.53-2.59 (m, 2H), 2.16 (t, J=7.2 Hz, 2H), 1.39 (quin, J=7.3 Hz, 2H), 1.28 (s, 6H)

Step 3: Methyl 1-benzyl-2,2-dimethyl-3-oxopiperidine-4-carboxylate

A solution of Methyl 4-(benzyl(1-methoxy-2-methyl-1-oxopropan-2-yl)amino)butanoate (590 mg, 1.92 mmol) in THF was stirred at room temperature with potassium tert-butoxide (2.0 equiv., 3.84 mmol) for 1 h. The reaction mixture was quenched with NaHCO$_3$ solution for 30 minutes and extracted twice with EtOAc. The organic solution was washed with brine, dried over Na$_2$SO$_4$ and evaporated under reduced pressure. The crude was purified by column chromatography on silica gel using ethyl acetate in hexane as mobile phase to give Methyl 1-benzyl-2,2-dimethyl-3-oxopiperidine-4-carboxylate (0.4 g, 76%) as an oil (85% purity by UPLCMS).

UPLC-MS (Basic Method, 2 min): rt 1.41 min, m/z 276.2 [M+H]$^+$ $^1$H NMR (400 MHz, DMSO-d6) δ ppm: 7.25-7.37 (m, 6H), 3.71 (s, 3H), 3.65 (s, 1H), 2.44 (s, 3H), 2.05-2.10 (m, 2H), 1.33 (s, 6H)

Step 4: 7-Benzyl-8,8-dimethyl-5,6,7,8-tetrahydropyrido[3,4-d]pyrimidine-2,4(1H,3H)-dione To a solution of Methyl 1-benzyl-2,2-dimethyl-3-oxopiperidine-4-carboxylate (400 mg, 1.45 mmol) in ethanol were added potassium tert-butoxide (2.5 equiv., 3.64 mmol) and urea (2.5 equiv., 3.64 mmol), and the resulting mixture was stirred under reflux for 18 h. The reaction mixture was quenched with water and solvent was evaporated under reduced pressure. The residue was diluted in water and extracted twice with EtOAc. The organic solution was washed with brine, dried over Na$_2$SO$_4$ and evaporated under reduced pressure. The crude was purified by column chromatography on silica gel using ethyl acetate in hexane as mobile phase to give 7-Benzyl-8,8-dimethyl-5,6,7,8-tetrahydropyrido[3,4-d]pyrimidine-2,4(1H,3H)-dione (0.2 g, 48%) as an oil (80% purity by UPLCMS). UPLC-MS (Basic Method, 2 min): rt 0.95 min, m/z 286.2 [M+H]+No NMR was reported.

Step 5: 7-Benzyl-2,4-dichloro-8,8-dimethyl-5,6,7,8-tetrahydropyrido[3,4-d]pyrimidine A solution of 7-Benzyl-8,8-dimethyl-5,6,7,8-tetrahydropyrido[3,4-d]pyrimidine-2,4(1H,3H)-dione (200 mg, 0.7 mmol) in POCl$_3$ (30 vol., 3.65 mL) in presence of catalytic DMF was stirred at 85° C. under N$_2$ for 18 h. The reaction mixture was quenched by slow addition of water and stirred 15 minutes. The aqueous solution was extracted with EtOAc 3 times then the organic solution was washed twice with NaHCO$_3$ solution and once with brine. The organic solution was dried over Na$_2$SO$_4$ and evaporated under reduced pressure to give 7-Benzyl-2,4-dichloro-8,8-dimethyl-5,6,7,8-tetrahydropyrido[3,4-d]pyrimidine (44 mg, 20%) as a yellow oil (87% purity by UPLCMS).

UPLC-MS (Basic Method, 2 min): rt 1.46 min, m/z 322.1 [M+H]+

Step 6: N-(2-(1H-indol-3-yl)ethyl)-7-benzyl-2-chloro-8,8-dimethyl-5,6,7,8-tetrahydropyrido[3,4-d]pyrimidin-4-amine (General method A)

Prepared according to general method A, using 7-Benzyl-2,4-dichloro-8,8-dimethyl-5,6,7,8-tetrahydropyrido[3,4-d]pyrimidine (44 mg) to give N-(2-(1H-indol-3-yl)ethyl)-7-benzyl-2-chloro-8,8-dimethyl-5,6,7,8-tetrahydropyrido[3,4-d]pyrimidin-4-amine (48 mg, 77%) as a brown gum (67% purity by UPLCMS, 26% tryptamine still present).

UPLC-MS (Basic Method, 2 min): rt 1.43 min, m/z 446.2 [M+H]$^+$ $^1$H NMR (400 MHz, DMSO-d6) δ ppm: 10.81 (br s, 1H), 7.27-7.35 (m, 6H), 6.92-7.09 (m, 5H), 3.67 (s, 2H), 3.53-3.63 (m, 2H), 2.91-2.97 (m, 2H), 2.84-2.91 (m, 2H), 2.77-2.84 (m, 2H), 1.39 (s, 6H)

Step 7: N-(2-(1H-indol-3-yl)ethyl)-7-benzyl-2-(5-fluoropyridin-3-yl)-8,8-dimethyl-5,6,7,8-tetrahydropyrido[3,4-d]pyrimidin-4-amine (Example 18a)

Prepared according to general method B, using N-(2-(1H-indol-3-yl)ethyl)-7-benzyl-2-chloro-8,8-dimethyl-5,6,7,8-tetrahydropyrido[3,4-d]pyrimidin-4-amine (48 mg) to give N-(2-(1H-indol-3-yl)ethyl)-7-benzyl-2-(5-fluoropyridin-3-yl)-8,8-dimethyl-5,6,7,8-tetrahydropyrido[3,4-d]pyrimidin-4-amine (48 mg, 77%) as a foam.

UPLC-MS (Basic Method, 4 min): rt 1.39 min, m/z 507.3 [M+H]$^+$ $^{19}$F NMR (400 MHz, DMSO-d$_6$) δ ppm −127.78 proton decoupled $^1$H NMR (400 MHz, DMSO-d6) δ ppm: 10.82 (s, 1H), 9.39 (t, J=1.6 Hz, 1H), 8.67 (d, J=2.9 Hz, 1H), 8.36-8.41 (m, 1H), 7.60 (d, J=7.8 Hz, 1H), 7.31-7.42 (m, 5H), 7.18-7.31 (m, 2H), 7.04-7.12 (m, 2H), 6.91-7.04 (m, 1H), 3.74-3.83 (m, 2H), 3.72 (s, 2H), 2.98-3.07 (m, 2H), 1.51 (s, 6H)

Step 8: N-(2-(1H-indol-3-yl)ethyl)-2-(5-fluoropyridin-3-yl)-8,8-dimethyl-5,6,7,8-tetrahydropyrido[3,4-d]pyrimidin-4-amine (Example 18b)

A slurry of 10% palladium on carbon (20 mg) in ethanol (2 mL) was added, under nitrogen to a solution of N-(2-(1H-indol-3-yl)ethyl)-7-benzyl-2-(5-fluoropyridin-3-yl)-8,8-dimethyl-5,6,7,8-tetrahydropyrido[3,4-d]pyrimidin-4-amine (22 mg) in THF (2 mL) and ethanol (8 mL). The mixture was hydrogenated at 1 atm for 24 hours. The catalyst was filtered off through a celite plug and washed through with further ethanol. The filtrate was evaporated to dryness. Purification on silica (4 g cartridge), eluting with a gradient of 7M ammonia in methanol (0-5%) in DCM, afforded the product as a colourless glass (8 mg, 44%).

UPLC-MS (Acidic Method, 4 min): rt 1.43 min, m/z 417.3 [M+H]$^+$ $^{19}$F NMR (400 MHz, DMSO-d$_6$) δ ppm −127.84 proton decoupled $^1$H NMR (400 MHz, DMSO-d6) δ ppm: 10.83 (s, 1H), 9.36 (t, J=1.6 Hz, 1H), 8.66 (d, J=2.9 Hz, 1H), 8.29-8.43 (m, 1H), 7.62 (d, J=7.9 Hz, 1H), 7.35 (d, J=8.0 Hz, 1H), 7.22 (d, J=2.3 Hz, 1H), 7.02-7.12 (m, 2H), 6.98 (td, J=7.4, 0.9 Hz, 1H), 3.66-3.91 (m, 2H), 3.01-3.08 (m, 2H), 2.98 (br t, J=5.7 Hz, 2H), 2.30-2.40 (m, 2H), 1.39 (s, 6H) (1H exchangeable not seen).

Example 19 Preparation of N-(2-(1H-benzo[d]imidazol-2-yl)ethyl)-2-(5-fluoropyridin-3-yl)-5,6,7,8-tetrahydropyrido[3,4-d]pyrimidin-4-amine

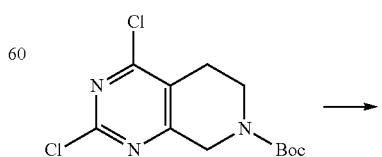

Chemical Formula: C$_{12}$H$_{15}$Cl$_2$N$_3$O$_2$
Molecular Weight: 304.17

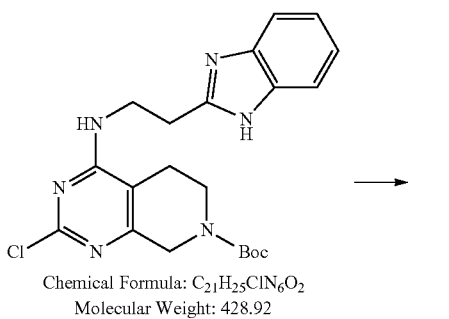

Chemical Formula: C$_{21}$H$_{25}$ClN$_6$O$_2$
Molecular Weight: 428.92

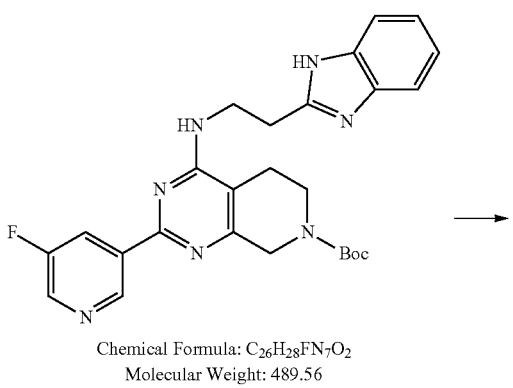

Chemical Formula: C$_{26}$H$_{28}$FN$_7$O$_2$
Molecular Weight: 489.56

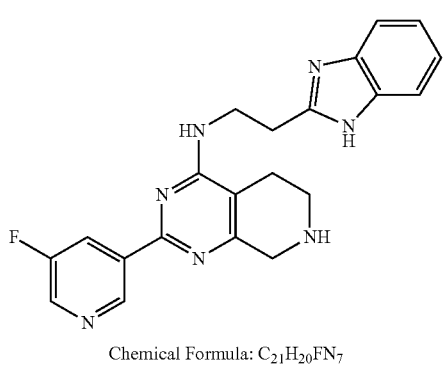

Chemical Formula: C$_{21}$H$_{20}$FN$_7$
Molecular Weight: 389.44

Step 1 tert-butyl 4-((2-(1H-benzo[d]imidazol-2-yl)ethyl)amino)-2-chloro-5,8-di hydropyrido[3,4-d]pyrimidine-7(6H)-carboxylate Prepared according to general method A, using tert-butyl 2,4-dichloro-5,8-dihydropyrido[3,4-d]pyrimidine-7(6H)-carboxylate (300 mg) and 2-(1H-2-benzoimidazolyl 0-ethylamine (160 mg, 1 equiv.) to give the desired product and corresponding regioisomer (8%) after purification using Biotage (Telos column 20 g, Eluent DCM-MeoH 0 to 5%) as a yellow solid (226 mg, 53%).

UPLC-MS (acidic Method, 2 min): rt 0.86 min, m/z 429/431 [M+H]$^+$ $^1$H NMR (400 MHz, CDCl$_3$-d) δ ppm 7.48-7.65 (m, 2H), 7.22-7.27 (m, 2H), 4.37-4.47 (m, 2H), 3.99-4.10 (m, 2H), 3.63-3.73 (m, 2H), 3.19-3.27 (m, 2H), 2.34-2.47 (m, 2H), 1.41-1.49 (m, 9H) (2H exchangeable not seen).

Step 2 tert-butyl 4-((2-(1H-benzo[d]imidazol-2-yl)ethyl)amino)-2-(5-fluoropyridin-3-yl)-5,8-dihydropyrido[3,4-d]pyrimidine-7(6H)-carboxylate Prepared according to general method B, using tert-butyl 4-((2-(1H-benzo[d]imidazol-2-yl)ethyl)amino)-2-chloro-5,8-dihydropyrido[3,4-d]pyrimidine-7(6H)-carboxylate (220 mg) and 5-fluoropyridine-3-boronic acid (140 mg) to give the desired product as a residue (130 mg, 50%).

UPLC-MS (acidic Method, 2 min): rt 0.90 min, m/z 490.2 [M+H]$^+$ $^{19}$F NMR (400 MHz, DMSO-d$_6$) δ ppm −127.69 proton decoupled $^1$H NMR (400 MHz, DMSO-d$_6$) δ ppm 12.23-12.31 (m, 1H), 9.29-9.36 (m, 1H), 8.63-8.69 (m, 1H), 8.35-8.44 (m, 1H), 7.49-7.57 (m, 1H), 7.31-7.43 (m, 2H), 7.04-7.15 (m, 2H), 4.35-4.46 (m, 2H), 3.91-4.02 (m, 2H), 3.59-3.70 (m, 2H), 3.18-3.22 (m, 2H), 2.40-2.47 (m, 2H), 1.41-1.49 (m, 9H)

Step 3 N-(2-(1H-benzo[d]imidazol-2-yl)ethyl)-2-(5-fluoropyridin-3-yl)-5,6,7,8-tetrahydropyrido[3,4-d]pyrimidin-4-amine Prepared according to general method C, using tert-butyl 4-((2-(1H-benzo[d]imidazol-2-yl)ethyl)amino)-2-(5-fluoropyridin-3-yl)-5,8-dihydropyrido[3,4-d]pyrimidine-7(6H)-carboxylate (120 mg) to afford the desired product (70 mg, 73%).

UPLC-MS (basic Method, 4 min): rt 1.22 min, m/z 390.2 [M+H]$^+$

19F NMR (400 MHz, DMSO-d$_6$) δ ppm −127.81 proton decoupled $^1$H NMR (400 MHz, DMSO-d$_6$) δ ppm 12.17-12.35 (m, 1H), 9.28-9.37 (m, 1H), 8.61-8.67 (m, 1H), 8.33-8.42 (m, 1H), 7.47-7.59 (m, 1H), 7.33-7.45 (m, 1H), 7.15-7.23 (m, 1H), 7.05-7.14 (m, 2H), 3.96 (br d, J=5.9 Hz, 2H), 3.71 (s, 2H), 3.19 (t, J=7.2 Hz, 2H), 2.98 (t, J=5.7 Hz, 2H), 2.68-2.92 (m, 1H), 2.28-2.38 (m, 2H).

Example 20 Preparation of N-(2-(1H-indol-3-yl)ethyl)-2-(5-methylpyridin-3-yl)-5,6,7,8-tetrahydropyrido[3,4-d]pyrimidin-4-amine

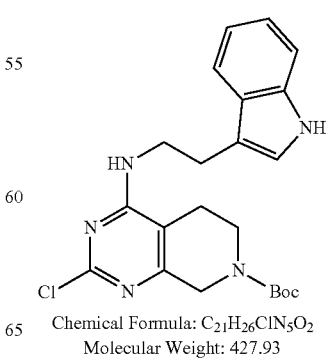

Chemical Formula: C$_{21}$H$_{26}$ClN$_5$O$_2$
Molecular Weight: 427.93

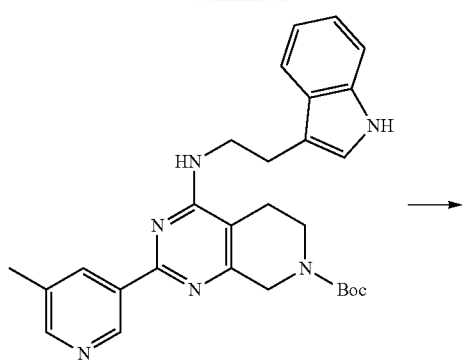

Chemical Formula: C₂₈H₃₂N₆O₂
Molecular Weight: 484.60

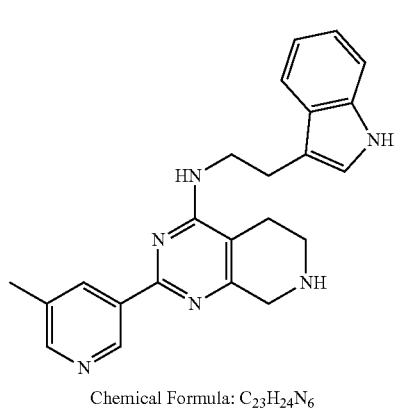

Chemical Formula: C₂₃H₂₄N₆
Molecular Weight: 384.49

Step 1 tert-butyl 4-((2-(1H-indol-3-yl)ethyl)amino)-2-(5-methylpyridin-3-yl)-5,8-dihydropyrido[3,4-d]pyrimidine-7(6H)-carboxylate Prepared according to general method B, using tert-butyl 4-((2-(1H-indol-3-yl)ethyl)amino)-2-chloro-5,8-dihydropyrido[3,4-d]pyrimidine-7(6H)-carboxylate (180 mg) and 5-methylpyridine-3-boronic acid (100 mg), to give the desired product as a residue (60 mg, 30%).
UPLC-MS (acidic Method, 4 min): rt 1.66 min, m/z 485.3 [M+H]⁺
¹H NMR (400 MHz, DMSO-d₆) δ ppm 10.80-10.88 (m, 1H), 9.24-9.32 (m, 1H), 8.46-8.52 (m, 1H), 8.36-8.43 (m, 1H), 7.57-7.63 (m, 1H), 7.32-7.38 (m, 1H), 7.21 (d, J=2.1 Hz, 2H), 7.03-7.11 (m, 1H), 6.93-7.00 (m, 1H), 4.34-4.45 (m, 2H), 3.73-3.85 (m, 2H), 3.60-3.69 (m, 2H), 3.00-3.09 (m, 2H), 2.41-2.46 (m, 2H), 2.35-2.39 (m, 3H), 1.44 (s, 9H)

Step 2 N-(2-(1H-indol-3-yl)ethyl)-2-(5-methylpyridin-3-yl)-5,6,7,8-tetrahydropyrido[3,4-d]pyrimidin-4-amine Prepared according to general method C, using tert-butyl 4-((2-(1H-indol-3-yl)ethyl)amino)-2-(5-methylpyridin-3-yl)-5,8-dihydropyrido[3,4-d]pyrimidine-7(6H)-carboxylate (50 mg), to afford the desired product (22 mg, 50%).
UPLC-MS (basic Method, 4 min): rt 1.55 min, m/z 385.2 [M+H]⁺
¹H NMR (400 MHz, DMSO-d₆) δ ppm 10.78-10.89 (m, 1H), 9.22-9.31 (m, 1H), 8.43-8.53 (m, 1H), 8.34-8.43 (m, 1H), 7.58-7.65 (m, 1H), 7.31-7.39 (m, 1H), 7.18-7.23 (m, 1H), 6.93-7.12 (m, 3H), 3.73 (br s, 4H), 2.89-3.15 (m, 4H), 2.26-2.43 (m, 5H) (1H exchangeable not seen).

Example 21 Preparation of N-(2-(1H-indol-3-yl)ethyl)-2-(5-fluoropyridin-3-yl)-5,6,7,8-tetrahydropyrido[4,3-d]pyrimidin-4-amine

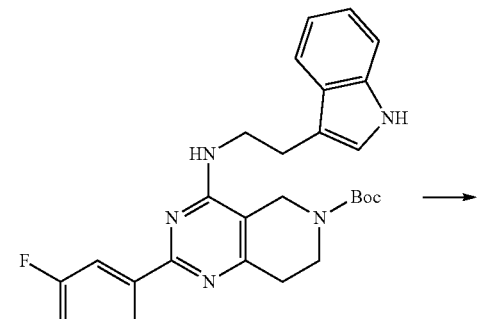

Chemical Formula: C₂₂H₂₆ClN₅O₂
Molecular Weight: 427.93

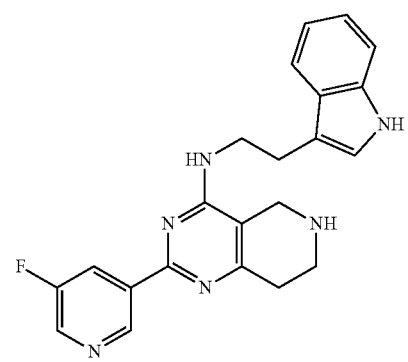

Chemical Formula: C₂₇H₂₉FN₆O₂
Molecular Weight: 488.57

Chemical Formula: C₂₂H₂₁FN₆
Molecular Weight: 388.45

Step 1 tert-butyl 4-((2-(1H-indol-3-yl)ethyl)amino)-2-(5-fluoropyridin-3-yl)-7,8-di hydropyrido[4,3-d]pyrimidine-6(5H)-carboxylate Prepared according to general method B, tert-butyl 4-((2-(1H-indol-3-yl)ethyl)amino)-2-chloro-7,8-dihydropyrido[4,3-d]pyrimidine-6(5H)-carboxylate (230 mg) and 5-fluoropyridine-3-boronic acid (90 mg) to give the desired product as a residue (130 mg, 49%).

UPLC-MS (Basic Method, 2 min): rt 1.29 min, m/z 489 [M+H]$^+$ $^{19}$F NMR (400 MHz, DMSO-d$_6$) δ ppm −127.96 proton decoupled $^1$H NMR (400 MHz, CDCl$_3$-d) δ ppm 9.41-9.47 (m, 1H), 8.50-8.55 (m, 1H), 8.33-8.41 (m, 1H), 8.05-8.14 (m, 1H), 7.60-7.65 (m, 1H), 7.37-7.42 (m, 1H), 7.20-7.26 (m, 1H), 7.12-7.18 (m, 1H), 7.07-7.11 (m, 1H), 4.52-4.66 (m, 1H), 4.07-4.18 (m, 2H), 3.93-4.02 (m, 2H), 3.66-3.75 (m, 2H), 3.10-3.21 (m, 2H), 2.81-2.90 (m, 2H), 1.50 (s, 9H)

Step 2 N-(2-(1H-indol-3-yl)ethyl)-2-(5-fluoropyridin-3-yl)-5,6,7,8-tetrahydropyrido[4,3-d]pyrimidin-4-amine 5N HCl in IPA (2 mL) was added to a solution of tert-butyl 4-((2-(1H-indol-3-yl)ethyl)amino)-2-(5-fluoropyridin-3-yl)-7,8-dihydropyrido[4,3-d]pyrimidine-6(5H)-carboxylate (130 mg) in DCM (5m L). The reaction mixture darkened in colour. After 7 h the reaction mixture was evaporated. Loose SCX resin (0.5 g) was added followed by water/methanol/acetonitrile. Spin to mix for about 10 min, then load into a fritted tube and allow to drain. The SCX cartridge so formed was washed through with methanol (10 mL). The product was eluted as the free base, eluting with 7M ammonia in methanol (10 mL) then DCM: 7M ammonia in methanol. The free based material was evaporated, then triturated with diethyl ether and filtered to afford the desired product as a white solid (55 mg, 53%). UPLC-MS (Basic Method, 4 min): rt 1.61 min, m/z 389 [M+H]$^+$ $^1$H NMR (400 MHz, DMSO-d$_6$+D2O) δ ppm 9.21 (s, 1H), 8.59 (d, J=2.8 Hz, 1H), 8.21-8.30 (m, 1H), 7.53-7.61 (m, 1H), 7.28-7.36 (m, 1H), 7.15 (s, 1H), 7.00-7.09 (m, 1H), 6.91-6.99 (m, 1H), 3.70-3.79 (m, 2H), 3.59 (s, 2H), 2.94-3.08 (m, 4H), 2.64-2.73 (m, 2H)

Example 22 Preparation of N-(2-(1H-indol-3-yl)ethyl)-2-(5-chloropyridin-3-yl)-5,6,7,8-tetrahydropyrido[3,4-d]pyrimidin-4-amine

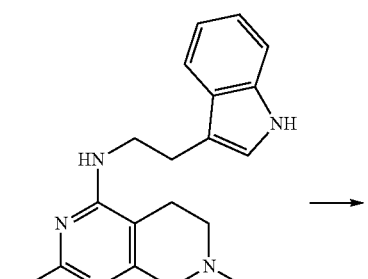

Chemical Formula: C$_{22}$H$_{26}$ClN$_5$O$_2$
Molecular Weight: 427.93

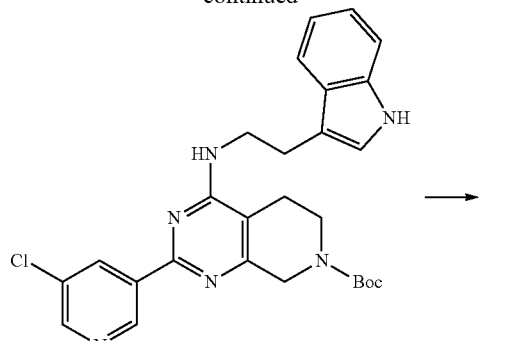

Chemical Formula: C$_{27}$H$_{29}$ClN$_6$O$_2$
Molecular Weight: 505.02

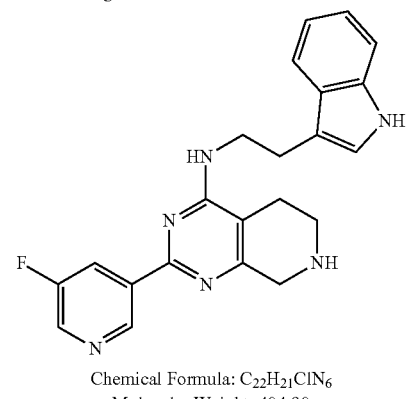

Chemical Formula: C$_{22}$H$_{21}$ClN$_6$
Molecular Weight: 404.90

Step 1 tert-butyl 4-((2-(1H-indol-3-yl)ethyl)amino)-2-(5-chloropyridin-3-yl)-5,8-di hydropyrido[3,4-d]pyrimidine-7(6H)-carboxylate Prepared according to general method B, using tert-butyl 4-((2-(1H-indol-3-yl)ethyl)amino)-2-chloro-5,8-dihydropyrido[3,4-d]pyrimidine-7(6H)-carboxylate (180 mg) and 5-chloropyridine-3-boronic acid (110 mg), to give the desired product as a residue (90 mg, 40%).

UPLC-MS (acidic Method, 4 min): rt 2.27 min, m/z 505.2/507.2 [M+H]$^+$ $^1$H NMR (400 MHz, DMSO-d$_6$) δ ppm 10.79-10.89 (m, 1H), 9.34-9.41 (m, 1H), 8.69-8.75 (m, 1H), 8.55-8.61 (m, 1H), 7.57-7.63 (m, 1H), 7.27-7.38 (m, 2H), 7.18-7.24 (m, 1H), 7.03-7.11 (m, 1H), 6.95-7.02 (m, 1H), 4.36-4.44 (m, 2H), 3.74-3.83 (m, 2H), 3.60-3.68 (m, 2H), 3.00-3.09 (m, 2H), 2.41-2.47 (m, 2H), 1.44 (s, 9H)

Step 2 N-(2-(1H-indol-3-yl)ethyl)-2-(5-chloropyridin-3-yl)-5,6,7,8-tetrahydropyrido[3,4-d]pyrimidin-4-amine Prepared according to general method C, using tert-butyl 4-((2-(1H-indol-3-yl)ethyl)amino)-2-(5-chloropyridin-3-yl)-5,8-dihydropyrido[3,4-d]pyrimidine-7(6H)-carboxylate (85 mg), to afford the desired product (45 mg, 65%).

UPLC-MS (basic Method, 4 min): rt 1.73 min, m/z 405.2/407.2 [M+H]$^+$ $^1$H NMR (400 MHz, DMSO-d$_6$) δ ppm 10.79-10.88 (m, 1H), 9.37 (d, J=1.4 Hz, 1H), 8.67-8.74 (m, 1H), 8.54-8.61 (m, 1H), 7.58-7.66 (m, 1H), 7.31-7.38 (m, 1H), 7.20 (d, J=1.6 Hz, 1H), 7.04-7.14 (m, 2H), 6.96-7.03 (m, 1H), 3.71 (s, 4H), 2.96-3.09 (m, 4H), 2.71-2.91 (m, 1H), 2.28-2.38 (m, 2H)

Example 23 Preparation of 5-(4-((2-(1H-indol-3-yl)ethyl)amino)-5,6,7,8-tetrahydro pyrido[3,4-d]pyrimidin-2-yl)nicotinonitrile

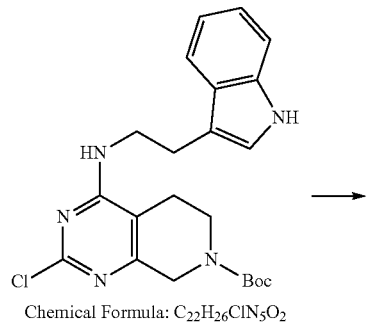

Chemical Formula: $C_{22}H_{26}ClN_5O_2$
Molecular Weight: 427.93

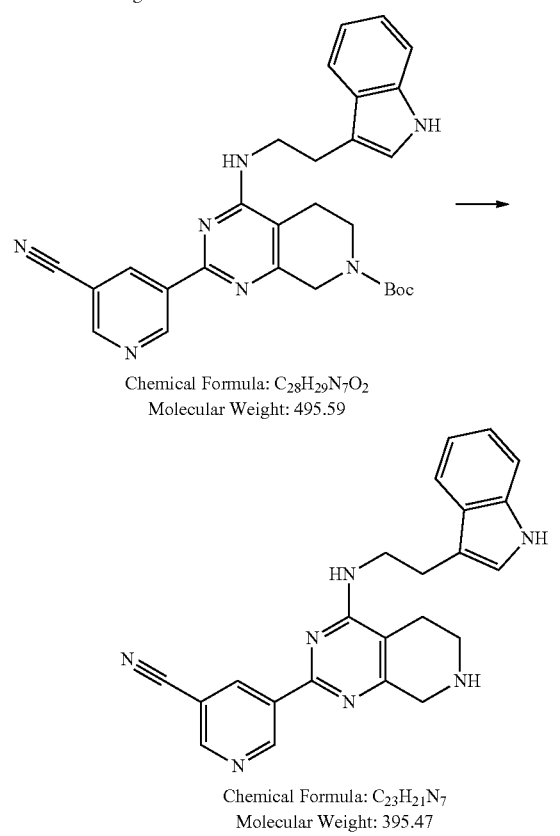

Chemical Formula: $C_{28}H_{29}N_7O_2$
Molecular Weight: 495.59

Chemical Formula: $C_{23}H_{21}N_7$
Molecular Weight: 395.47

Step 1 tert-butyl 4-((2-(1H-indol-3-yl)ethyl)amino)-2-(5-cyanopyridin-3-yl)-5,8-dihydropyrido[3,4-d]pyrimidine-7(6H)-carboxylate Prepared according to general method B, using tert-butyl 4-((2-(1H-indol-3-yl)ethyl)amino)-2-chloro-5,8-dihydropyrido[3,4-d]pyrimidine-7(6H)-carboxylate (180 mg) and 5-cyanopyridine-3-boronic acid (105 mg), to give the desired product as a residue (100 mg, 50%).
UPLC-MS (acidic Method, 4 min): rt 2.12 min, m/z 496.3 [M+H]⁺

$^1$H NMR (400 MHz, DMSO-d$_6$) δ ppm 10.76-10.85 (m, 1H), 9.63 (d, J=2.0 Hz, 1H), 9.10 (d, J=2.1 Hz, 1H), 8.88 (s, 1H), 7.56-7.62 (m, 1H), 7.32 (s, 2H), 7.18-7.22 (m, 1H), 7.03-7.09 (m, 1H), 6.96-7.02 (m, 1H), 4.35-4.45 (m, 2H), 3.75-3.85 (m, 2H), 3.59-3.69 (m, 2H), 2.99-3.07 (m, 2H), 2.40-2.48 (m, 2H), 1.44 (s, 9H)

Step 2 5-(4-((2-(1H-indol-3-yl)ethyl)amino)-5,6,7,8-tetrahydropyrido[3,4-d]pyrimidin-2-yl)nicotinonitrile Prepared according to general method C, using tert-butyl 4-((2-(1H-indol-3-yl)ethyl)amino)-2-(5-cyanopyridin-3-yl)-5,8-dihydropyrido[3,4-d]pyrimidine-7(6H)-carboxylate (90 mg), to afford the desired product (33 mg, 45%). UPLC-MS (basic Method, 4 min): rt 1.57 min, m/z 396.2 [M+H]⁺

$^1$H NMR (400 MHz, DMSO-d$_6$) δ ppm 10.79-10.85 (m, 1H), 9.61-9.67 (m, 1H), 9.06-9.12 (m, 1H), 8.83-8.90 (m, 1H), 7.57-7.65 (m, 1H), 7.30-7.37 (m, 1H), 7.17-7.23 (m, 1H), 7.11-7.17 (m, 1H), 7.03-7.10 (m, 1H), 6.96-7.03 (m, 1H), 3.75-3.85 (m, 2H), 3.72 (s, 2H), 2.96-3.07 (m, 4H), 2.68-2.85 (m, 1H), 2.30-2.37 (m, 2H)

Example 24 N-(2-(1H-indol-3-yl)ethyl)-2-(5-fluoropyridin-3-yl)-6,7-dihydro-5H-pyrrolo[3,4-d]pyrimidin-4-amine

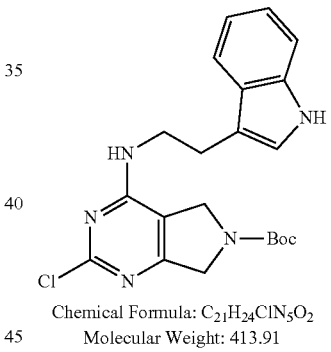

Chemical Formula: $C_{21}H_{24}ClN_5O_2$
Molecular Weight: 413.91

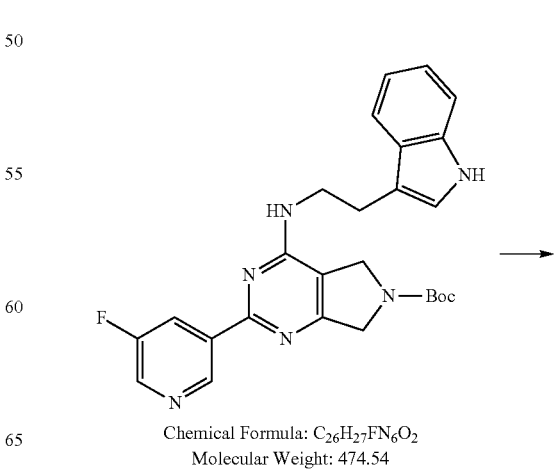

Chemical Formula: $C_{26}H_{27}FN_6O_2$
Molecular Weight: 474.54

63

-continued

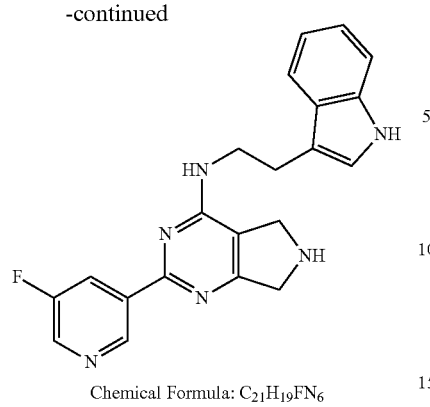

Chemical Formula: $C_{21}H_{19}FN_6$
Molecular Weight: 374.42

Step 1 t-Butyl 4-((2-(1H-indol-3-yl)ethyl)amino)-2-(5-fluoropyridin-3-yl)-5,7-dihydro-6H-pyrrolo[3,4-d]pyrimidine-6-carboxylate Prepared according to general method B, using t-butyl 4-((2-(1H-indol-3-yl)ethyl)amino)-2-chloro-5,7-dihydro-6H-pyrrolo[3,4-d]pyrimidine-6-carboxylate (520 mg) and 5-fluoropyridine-3-boronic acid (400 mg) to give the desired product as a white solid (550 mg, 90%).

UPLC-MS (acidic Method, 4 min): rt 2.00 min, m/z 475.2 [M+H]$^+$ $^{19}$F NMR (400 MHz, DMSO-d6) δ ppm –127.18-127.56 (1F, d) proton decoupled (rotamers)

$^1$H NMR (400 MHz, DMSO-d6) δ ppm: 10.82 (s, 1H), 9.31 (d, J=1.6 Hz, 1H), 8.68 (d, J=2.8 Hz, 1H), 8.31 (ddt, J=8.4, 3.3, 1.6 Hz, 1H), 7.72 (br d, J=3.3 Hz, 1H), 7.59 (br d, J=7.9 Hz, 1H), 7.34 (d, J=8.0 Hz, 1H), 7.21 (d, J=2.3 Hz, 1H), 7.03-7.11 (m, 1H), 6.94-7.02 (m, 1H), 4.71-4.81 (m, 1H), 4.37-4.53 (m, 4H), 3.78 (q, J=6.4 Hz, 2H), 3.03 (br t, J=7.5 Hz, 2H), 1.48 (d, J=4.8 Hz, 9H). (rotamers)

Step 2 N-(2-(1H-indol-3-yl)ethyl)-2-(5-fluoropyridin-3-yl)-6,7-dihydro-5H-pyrrolo[3,4-d]pyrimidin-4-amine TFA (3.0 mL) was added to a solution of t-butyl 4-((2-(1H-indol-3-yl)ethyl)amino)-2-(5-fluoropyridin-3-yl)-5,7-dihydro-6H-pyrrolo[3,4-d]pyrimidine-6-carboxylate (540 mg) in DCM (20 mL). Once complete as judged by UPLC, the reaction mixture was evaporated, then partitioned between 10% aqueous ammonia and ethyl acetate. The organic phase was separated and evaporated. The free base material was evaporated, then triturated sequentially with diethyl ether, then DCM and filtered to afford the desired product as a white solid (270 mg, 62%).

UPLC-MS (Acidic Method, 4 min): rt 1.02 min, m/z 375.2 [M+H]$^+$ $^{19}$F NMR (400 MHz, DMSO-d6) δ ppm –127.72 proton decoupled $^1$H NMR (400 MHz, DMSO-d6) δ ppm 10.83 (br s, 1H), 9.34 (s, 1H), 8.67 (d, J=2.9 Hz, 1H), 8.30-8.41 (m, 1H), 7.61 (d, J=7.8 Hz, 1H), 7.43 (br t, J=5.6 Hz, 1H), 7.35 (d, J=8.0 Hz, 1H), 7.21 (d, J=1.9 Hz, 1H), 7.08 (t, J=7.3 Hz, 1H), 6.94-7.03 (m, 1H), 3.98 (br d, J=5.6 Hz, 4H), 3.71-3.87 (m, 2H), 2.99-3.10 (m, 2H). 1H exchangeable not seen

64

Example 25 N-(2-(1H-indol-3-yl)ethyl)-2-(5-fluoropyridin-3-yl)-6-(methylsulfonyl)-6,7-dihydro-5H-pyrrolo[3,4-d]pyrimidin-4-amine

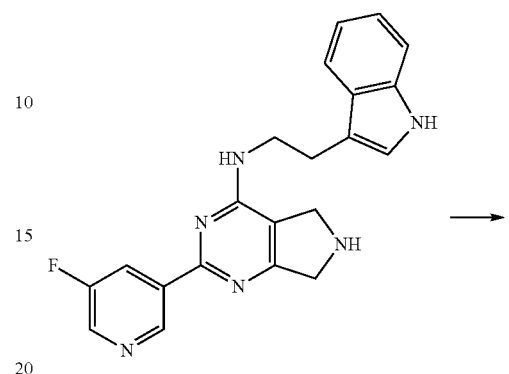

Chemical Formula: $C_{21}H_{19}FN_6$
Molecular Weight: 374.42

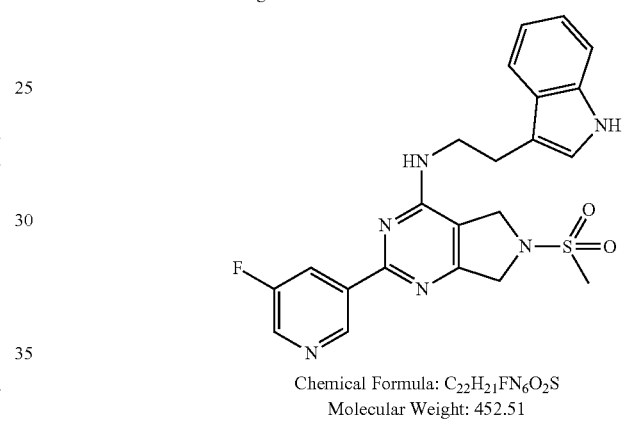

Chemical Formula: $C_{22}H_{21}FN_6O_2S$
Molecular Weight: 452.51

Step 1 N-(2-(1H-indol-3-yl)ethyl)-2-(5-fluoropyridin-3-yl)-6-(methylsulfonyl)-6,7-dihydro-5H-pyrrolo[3,4-d]pyrimidin-4-amine Methanesulfonyl chloride (50 μL) was added to a suspension of N-(2-(1H-indol-3-yl)ethyl)-2-(5-fluoropyridin-3-yl)-6,7-dihydro-5H-pyrrolo[3,4-d]pyrimidin-4-amine (90 mg) in DCM (10 mL), with triethyl amine (300 μL). After 2 hours, 33% aqueous ammonia (1 mL) was added. The reaction mixture was evaporated and purified on a silica cartridge eluting with a gradient of methanol (0-2%) in DCM. The product was purified further on a silica cartridge eluting with a gradient of ethyl acetate (10-80%) in hexane. Trituration in ether and filtered to afford the desired product as a white solid (50 mg, 45%).

UPLC-MS (Acidic Method, 4 min): rt 1.61 min, m/z 453.2 [M+H]$^+$ $^{19}$F NMR (400 MHz, DMSO-d$_6$) δ ppm –127.45 proton decoupled $^1$H NMR (400 MHz, DMSO-d$_6$) δ ppm 10.84 (br s, 1H), 9.33 (t, J=1.5 Hz, 1H), 8.70 (d, J=2.9 Hz, 1H), 8.30-8.37 (m, 1H), 7.74-7.78 (m, 1H), 7.59 (d, J=7.9 Hz, 1H), 7.34 (d, J=8.0 Hz, 1H), 7.24 (d, J=2.3 Hz, 1H), 7.04-7.11 (m, 1H), 6.94-7.02 (m, 1H), 4.44-4.63 (m, 4H), 3.77-3.84 (m, 2H), 2.99-3.11 (m, 5H).

Example 26 N-(2-(1H-indol-3-yl)ethyl)-2-(5-methylpyridin-3-yl)-5,6,7,8-tetrahydro pyrido[4,3-d]pyrimidin-4-amine

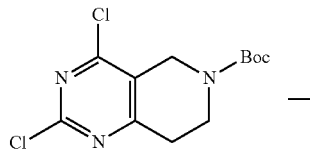

Chemical Formula: C₁₂H₁₅Cl₂N₃O₂
Molecular Weight: 304.17

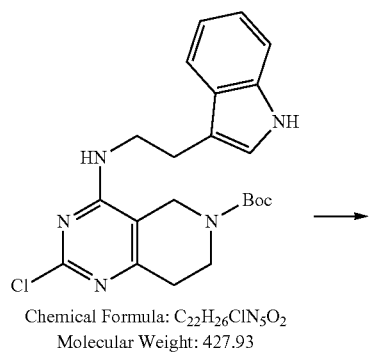

Chemical Formula: C₂₂H₂₆ClN₅O₂
Molecular Weight: 427.93

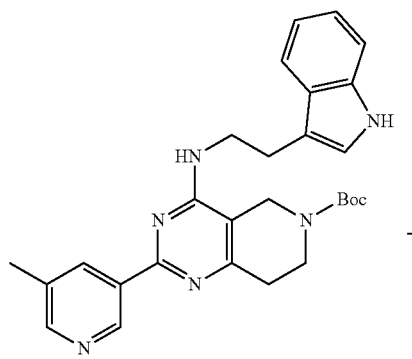

Chemical Formula: C₂₈H₃₂N₆O₂
Molecular Weight: 484.60

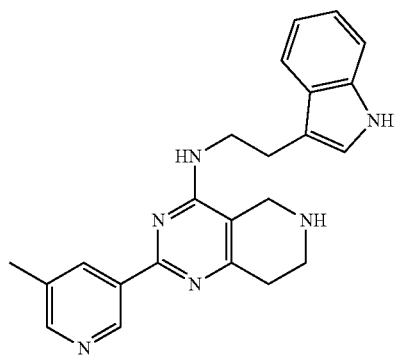

Chemical Formula: C₂₃H₂₄N₆
Molecular Weight: 384.49

Step 1 t-Butyl 4-((2-(1H-indol-3-yl)ethyl)amino)-2-chloro-7,8-dihydropyrido[4,3-d]pyrimidine-6(5H)-carboxylate Prepared according to general method A, using t-butyl 2,4-dichloro-7,8-dihydropyrido[4,3-d]pyrimidine-6(5H)-carboxylate (410 mg) to give the desired product as a solid (630 mg, >100%) UPLC-MS (Acidic Method, 2 min): rt 1.21 min, m/z 428/430 [M+H]⁺

¹H NMR (400 MHz, CDCl₃-d) δ ppm 7.97-8.18 (m, 1H), 7.59-7.68 (m, 1H), 7.34-7.44 (m, 1H), 7.19-7.26 (m, 1H), 7.11-7.18 (m, 1H), 7.05-7.09 (m, 1H), 4.09-4.17 (m, 2H), 3.79-3.90 (m, 2H), 3.59-3.68 (m, 2H), 3.04-3.15 (m, 2H), 2.70-2.80 (m, 2H), 1.46-1.52 (m, 9H).

Step 2 tert-butyl 4-((2-(1H-indol-3-yl)ethyl)amino)-2-(5-methylpyridin-3-yl)-7,8-dihydropyrido[4,3-d]pyrimidine-6(5H)-carboxylate Prepared according to general method B, using t-butyl 4-((2-(1H-indol-3-yl)ethyl)amino)-2-chloro-7,8-dihydropyrido[4,3-d]pyrimidine-6(5H)-carboxylate (180 mg) and 5-methylpyridine-3-boronic acid (100 mg) to give the desired product as a cream foam (100 mg, 49%).

UPLC-MS (Acidic Method, 2 min): rt 1.04 min, m/z 485 [M+H]⁺

¹H NMR (400 MHz, CDCl₃-d) δ ppm 9.35-9.39 (m, 1H), 8.81-8.88 (m, 1H), 8.50-8.54 (m, 1H), 8.26-8.37 (m, 1H), 7.56-7.62 (m, 1H), 7.35-7.41 (m, 1H), 7.16-7.23 (m, 1H), 7.08-7.15 (m, 2H), 4.12-4.19 (m, 2H), 3.93-4.02 (m, 2H), 3.67-3.75 (m, 2H), 3.11-3.22 (m, 2H), 2.86-2.94 (m, 2H), 2.53 (s, 3H), 1.50 (s, 9H) (2H exchangeable not seen).

Step 3 N-(2-(1H-indol-3-yl)ethyl)-2-(5-methylpyridin-3-yl)-5,6,7,8-tetrahydropyrido[4,3-d]pyrimidin-4-amine Prepared according to general method C, using tert-butyl 4-((2-(1H-indol-3-yl)ethyl)amino)-2-(5-methylpyridin-3-yl)-7,8-dihydropyrido[4,3-d]pyrimidine-6(5H)-carboxylate (100 mg), to afford the desired product as a white solid (26 mg, 56%).

UPLC-MS (Basic Method, 4 min): rt 1.53 min, m/z 385 [M+H]⁺

¹H NMR (400 MHz, DMSO-d₆) δ ppm 10.78-10.90 (m, 1H), 9.23-9.32 (m, 1H), 8.44-8.51 (m, 1H), 8.35-8.44 (m, 1H), 7.56-7.67 (m, 1H), 7.30-7.41 (m, 1H), 7.16-7.25 (m, 1H), 7.02-7.13 (m, 1H), 6.94-7.01 (m, 1H), 6.84-6.93 (m, 1H), 3.70-3.83 (m, 2H), 3.56 (s, 2H), 3.00-3.09 (m, 2H), 2.93-3.00 (m, 2H), 2.63 (br s, 2H), 2.37 (s, 3H) (1H exchangeable not seen).

Example 27 Preparation of N-(2-(1H-indol-3-yl)ethyl)-2-(5-chloropyridin-3-yl)-5,6,7,8-tetrahydropyrido[4,3-d]pyrimidin-4-amine

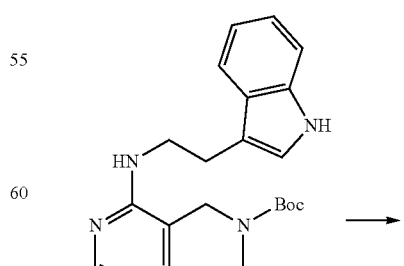

Chemical Formula: C₂₂H₂₆ClN₅O₂
Molecular Weight: 427.93

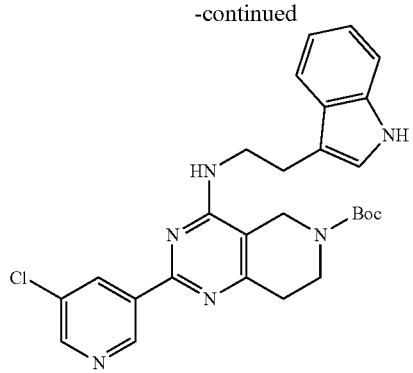

Chemical Formula: C₂₇H₂₉ClN₆O₂
Molecular Weight: 505.02

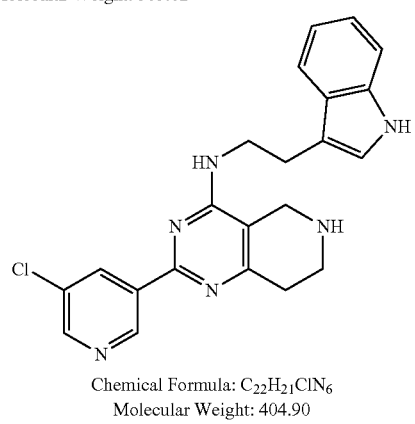

Chemical Formula: C₂₂H₂₁ClN₆
Molecular Weight: 404.90

Step 1 tert-butyl 4-((2-(1H-indol-3-yl)ethyl)amino)-2-(5-chloropyridin-3-yl)-7,8-dihydro pyrido[4,3-d]pyrimidine-6(5H)-carboxylate Prepared according to general method B, using tert-butyl 4-((2-(1H-indol-3-yl)ethyl)amino)-2-chloro-7,8-dihydropyrido[4,3-d]pyrimidine-6(5H)-carboxylate (180 mg) and 5-chloropyridine-3-boronic acid (100 mg) to give the desired product as a residue (130 mg, 53%).

UPLC-MS (Acidic Method, 2 min): rt 1.21 min, m/z 505/507 [M+H]⁺

¹H NMR (400 MHz, CDCl₃-d) δ ppm 9.44-9.46 (m, 1H), 8.61-8.65 (m, 1H), 7.59-7.65 (m, 1H), 7.35-7.43 (m, 3H), 7.08-7.08 (m, 1H), 6.89 (s, 1H), 6.62-6.69 (m, 1H), 6.11-6.20 (m, 1H), 4.12-4.15 (m, 2H), 3.99-4.02 (m, 2H), 3.69-3.72 (m, 2H), 3.14-3.18 (m, 2H), 2.95-2.98 (m, 2H), 1.49-1.50 (m, 9H)

Step 2 tetrahydropyrido[4,3-d]pyrimidin-4-amine

Prepared according to general method C, using tert-butyl 4-((2-(1H-indol-3-yl)ethyl)amino)-2-(5-chloropyridin-3-yl)-7,8-dihydropyrido[4,3-d]pyrimidine-6(5H)-carboxylate (130 mg), to afford the desired product as a white solid (50 mg, 48%).

UPLC-MS (Basic Method, 4 min): rt 1.73 min, m/z 405/407 [M+H]⁺

¹H NMR (400 MHz, DMSO-d₆) δ ppm 10.77-10.90 (m, 1H), 9.34-9.42 (m, 1H), 8.68-8.73 (m, 1H), 8.56-8.61 (m, 1H), 7.57-7.65 (m, 1H), 7.31-7.38 (m, 1H), 7.17-7.23 (m, 1H), 7.03-7.12 (m, 1H), 6.94-7.03 (m, 2H), 3.71-3.82 (m, 2H), 3.55 (s, 2H), 2.92-3.08 (m, 4H), 2.59-2.65 (m, 2H) (1H exchangeable not seen).

Example 28 Preparation of N-(2-(1H-benzo[d]imidazol-2-yl)ethyl)-2-(5-fluoropyridin-3-yl)-5,6,7,8-tetrahydropyrido[4,3-d]pyrimidin-4-amine

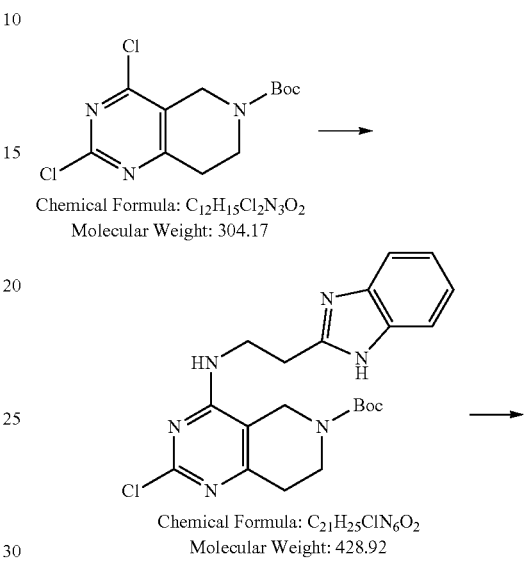

Chemical Formula: C₁₂H₁₅Cl₂N₃O₂
Molecular Weight: 304.17

Chemical Formula: C₂₁H₂₅ClN₆O₂
Molecular Weight: 428.92

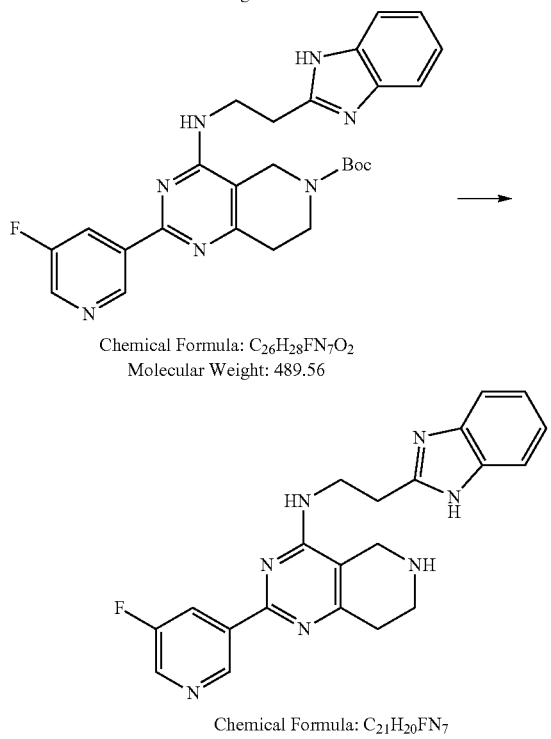

Chemical Formula: C₂₆H₂₈FN₇O₂
Molecular Weight: 489.56

Chemical Formula: C₂₁H₂₀FN₇
Molecular Weight: 389.44

Step 1 tert-butyl-4-((2-(1H-benzo[d]imidazol-2-yl)ethyl)amino)-2-chloro-7,8-di hydropyrido[4,3-d]pyrimidine-6(5H)-carboxylate Prepared according to general method A, using tert-butyl 2,4-dichloro-7,8-dihydropyrido[4,3-d]pyrimidine-6(5H)- carboxylate (200 mg) and 2-(1H-2-benzoimidazolyl 0-ethylamine (105 mg, 1 equiv.) to give the desired product after filtration and DCM rinse as a white solid (105 mg, 37%).

UPLC-MS (acidic Method, 2 min): rt 0.85 min, m/z 429/431 [M+H]$^+$ $^1$H NMR (400 MHz, DMSO-d$_6$) δ ppm 7.50-7.67 (m, 2H), 7.37-7.45 (m, 1H), 7.05-7.18 (m, 2H), 4.16 (s, 2H), 3.74-3.87 (m, 2H), 3.57 (s, 2H), 3.07-3.17 (m, 2H), 2.56-2.65 (m, 2H), 1.41 (s, 9H) (1H exchangeable not seen).

Step 2 tert-butyl-4-((2-(1H-benzo[d]imidazol-2-yl)ethyl)amino)-2-(5-fluoropyridin-3-yl)-7,8-dihydropyrido[4,3-d]pyrimidine-6(5H)-carboxylate Prepared according to general method B, using tert-butyl 4-((2-(1H-benzo[d]imidazol-2-yl)ethyl)amino)-2-chloro-7,8-dihydropyrido[4,3-d]pyrimidine-6(5H)-carboxylate (100 mg) and 5-fluoropyridine-3-boronic acid (70 mg) to give the desired product (60 mg, 75%).

UPLC-MS (acidic Method, 2 min): rt 0.90 min, m/z 490 [M+H]$^+$ $^{19}$F NMR (400 MHz, DMSO-d$_6$) δ ppm −127.69 proton decoupled $^1$H NMR (400 MHz, DMSO-d$_6$) δ ppm 12.21-12.31 (m, 1H), 9.31-9.36 (m, 1H), 8.66 (d, J=2.9 Hz, 1H), 8.35-8.43 (m, 1H), 7.50-7.57 (m, 1H), 7.33-7.42 (m, 2H), 7.07-7.13 (m, 2H), 4.25 (s, 2H), 3.93-4.02 (m, 2H), 3.60-3.68 (m, 2H), 3.16-3.24 (m, 2H), 2.69-2.77 (m, 2H), 1.43 (s, 9H)

Step 3 N-(2-(1H-benzo[d]imidazol-2-yl)ethyl)-2-(5-fluoropyridin-3-yl)-5,6,7,8-tetrahydropyrido[4,3-d]pyrimidin-4-amine Prepared according to general method C, using tert-butyl 4-((2-(1H-benzo[d]imidazol-2-yl)ethyl)amino)-2-(5-fluoropyridin-3-yl)-7,8-dihydropyrido[4,3-d]pyrimidine-6(5H)-carboxylate (55 mg) to afford the desired product as an off white solid (25 mg, 58%).

UPLC-MS (basic Method, 4 min): rt 1.22 min, m/z 390 [M+H]$^+$ $^{19}$F NMR (400 MHz, DMSO-d$_6$) δ ppm −127.82 proton decoupled $^1$H NMR (400 MHz, DMSO-d$_6$) δ ppm 12.17-12.36 (m, 1H), 9.33 (s, 1H), 8.64 (d, J=2.9 Hz, 1H), 8.32-8.45 (m, 1H), 7.47-7.58 (m, 1H), 7.36-7.44 (m, 1H), 7.01-7.16 (m, 3H), 3.88-4.02 (m, 2H), 3.55 (s, 2H), 3.12-3.26 (m, 2H), 2.89-3.03 (m, 2H), 2.59-2.67 (m, 2H) (1H exchangeable not seen).

Example 29 Preparation of N-(2-(6-fluoro-1H-indol-3-yl)ethyl)-2-(5-fluoropyridin-3-yl)-5,6,7,8-tetrahydropyrido[3,4-d]pyrimidin-4-amine

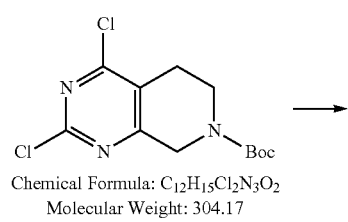

Chemical Formula: C$_{12}$H$_{15}$Cl$_2$N$_3$O$_2$
Molecular Weight: 304.17

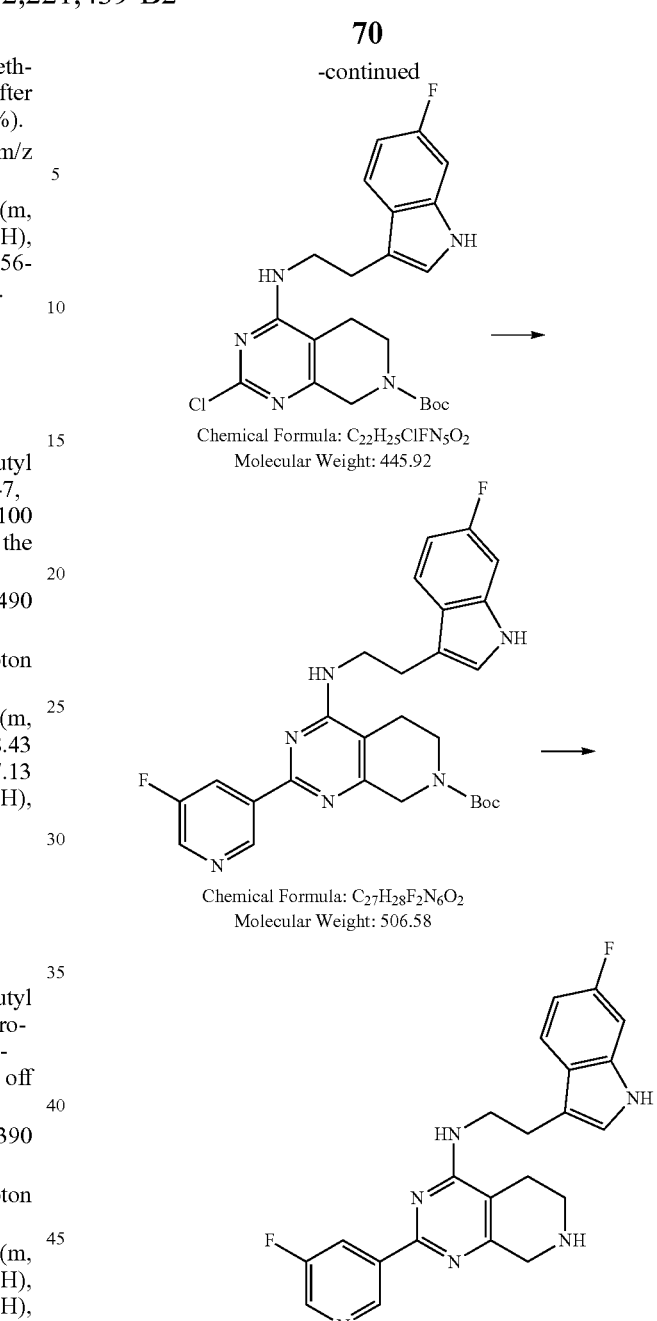

Chemical Formula: C$_{22}$H$_{25}$ClFN$_5$O$_2$
Molecular Weight: 445.92

Chemical Formula: C$_{27}$H$_{28}$F$_2$N$_6$O$_2$
Molecular Weight: 506.58

Chemical Formula: C$_{22}$H$_{20}$F$_2$N$_6$
Molecular Weight: 406.44

Step 1 tert-butyl 2-chloro-4-((2-(6-fluoro-1H-indol-3-yl)ethyl)amino)-5,8-dihydro pyrido[3,4-d]pyrimidine-7(6H)-carboxylate Prepared according to general method A, using t-butyl 2,4-dichloro-5,6-dihydropyrido[3,4-d]pyrimidine-7(8H)-carboxylate (250 mg) and 2-(6-fluoro-1H-indol-3-yl)ethanamine hydrochloride (176 mg, 1 equiv.). Purification by trituration with DCM gave the desired product as a white solid (110 mg, 30%). UPLC-MS (acidic Method, 2 min): rt 1.23 min, m/z 446/448 [M+H]$^+$ $^{19}$F NMR (400 MHz, DMSO-d$_6$) δ ppm −122.42 proton decoupled ¹H NMR (400 MHz, DMSO-d₆) δ ppm 10.84-10.93 (m, 1H), 7.60-7.67 (m, 1H), 7.49-7.58 (m, 1H), 7.15-7.20 (m, 1H), 7.06-7.13 (m, 1H), 6.79-6.87 (m, 1H), 4.26 (br s, 2H), 3.53-3.65 (m, 4H), 2.89-2.96 (m, 2H), 2.30-2.40 (m, 2H), 1.42 (s, 9H)

Step 2 tert-butyl 4-((2-(6-fluoro-1H-indol-3-yl)ethyl)amino)-2-(5-fluoropyridin-3-yl)-5,8-dihydropyrido[3,4-d]pyrimidine-7(6H)-carboxylate Prepared according to general method B, using tert-butyl 2-chloro-4-((2-(6-fluoro-1H-indol-3-yl)ethyl)amino)-5,8-dihydropyrido[3,4-d]pyrimidine-7(6H)-carboxylate (105 mg) and 5-fluoropyridine-3-boronic acid (65 mg) to give the desired product as a solid (55 mg, 74%).

UPLC-MS (acidic Method, 2 min): rt 1.26 min, m/z 507 [M+H]⁺

¹⁹F NMR (400 MHz, DMSO-d₆) δ ppm −122.49/−127.68 proton decoupled

¹H NMR (400 MHz, DMSO-d₆) δ ppm 10.86-10.93 (m, 1H), 9.26-9.33 (m, 1H), 8.64-8.70 (m, 1H), 8.25-8.32 (m, 1H), 7.52-7.58 (m, 2H), 7.18-7.22 (m, 1H), 7.06-7.13 (m, 1H), 6.77-6.85 (m, 1H), 4.37-4.44 (m, 2H), 3.74-3.83 (m, 2H), 3.60-3.68 (m, 2H), 2.98-3.06 (m, 2H), 2.39-2.46 (m, 2H), 1.44 (s, 9H)

Step 3 1N-(2-(6-fluoro-1H-indol-3-yl)ethyl)-2-(5-fluoropyridin-3-yl)-5,6,7,8-tetrahydropyrido[3,4-d]pyrimidin-4-amine Prepared according to general method C, using tert-butyl 4-((2-(6-fluoro-1H-indol-3-yl)ethyl)amino)-2-(5-fluoropyridin-3-yl)-5,8-dihydropyrido[3,4-d]pyrimidine-7(6H)-carboxylate (55 mg) to afford the desired product as a brown solid (14 mg, 32%).

UPLC-MS (Basic Method, 4 min): rt 1.65 min, m/z 407 [M+H]⁺

¹⁹F NMR (400 MHz, DMSO-d₆) δ ppm −122.48, −127.80 proton decoupled

¹H NMR (400 MHz, DMSO-d₆) δ ppm 10.83-10.95 (m, 1H), 9.24-9.33 (m, 1H), 8.60-8.68 (m, 1H), 8.21-8.32 (m, 1H), 7.53-7.62 (m, 1H), 7.17-7.23 (m, 1H), 7.04-7.14 (m, 2H), 6.76-6.87 (m, 1H), 3.67-3.85 (m, 4H), 2.95-3.08 (m, 4H), 2.28-2.40 (m, 2H) (1H exchangeable not seen).

Example 30 Preparation of N-(2-(5-fluoro-1H-indol-3-yl)ethyl)-2-(5-fluoropyridin-3-yl)-5,6,7,8-tetrahydropyrido [3,4-d]pyrimidin-4-amine

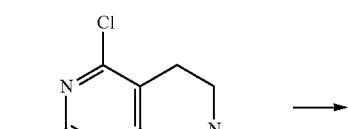

Chemical Formula: C₁₂H₁₅Cl₂N₃O₂
Molecular Weight: 304.17

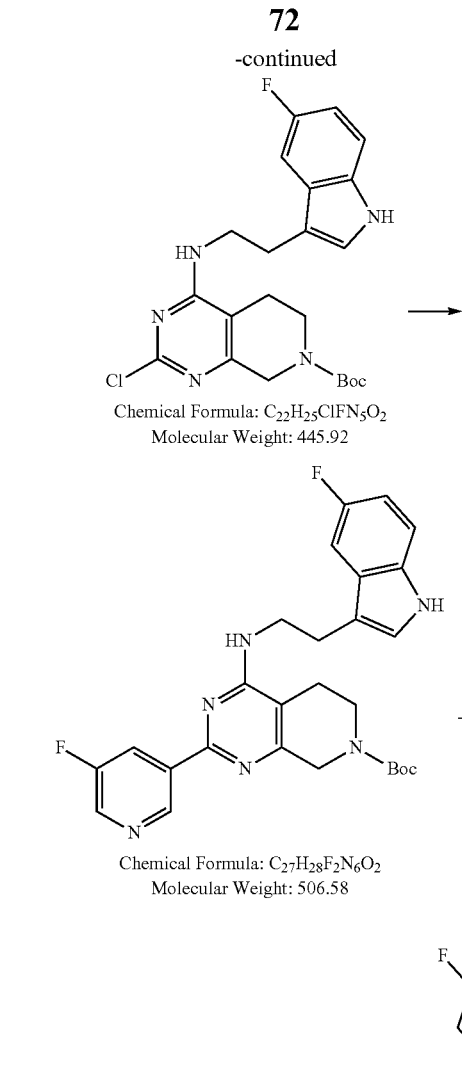

Chemical Formula: C₂₂H₂₅ClFN₅O₂
Molecular Weight: 445.92

Chemical Formula: C₂₇H₂₈F₂N₆O₂
Molecular Weight: 506.58

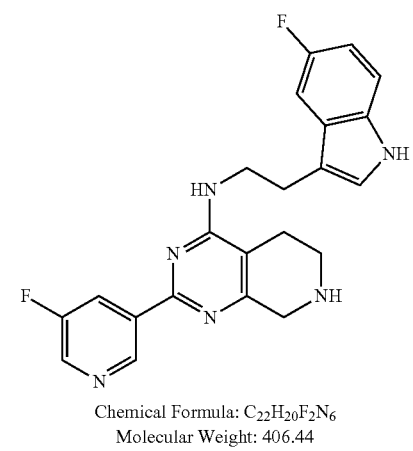

Chemical Formula: C₂₂H₂₀F₂N₆
Molecular Weight: 406.44

Step 1 tert-butyl 2-chloro-4-((2-(5-fluoro-1H-indol-3-yl)ethyl)amino)-5,8-dihydro pyrido[3,4-d]pyrimidine-7(6H)-carboxylate Prepared according to general method A, using tert-butyl 2,4-dichloro-5,8-dihydropyrido[3,4-d]pyrimidine-7(6H)-carboxylate (250 mg) and 2-(5-fluoro-1H-indol-3-yl)ethanamine hydrochloride (176 mg, 1 equiv.). Purification by trituration with DCM afforded the desired product as a white solid (157 mg, 43%).

UPLC-MS (acidic Method, 2 min): rt 1.22 min, m/z 446/448 [M+H]⁺

<sup>19</sup>F NMR (400 MHz, DMSO-d<sub>6</sub>) δ ppm −125.70 proton decoupled

<sup>1</sup>H NMR (400 MHz, DMSO-d<sub>6</sub>) δ ppm 10.88-10.97 (m, 1H), 7.49-7.65 (m, 1H), 7.38-7.46 (m, 1H), 7.38-7.46 (m, 1H), 7.29-7.35 (m, 1H), 7.23-7.29 (m, 1H), 6.85-6.95 (m, 1H), 4.19-4.31 (m, 2H), 3.57 (br d, J=5.9 Hz, 4H), 2.85-2.98 (m, 2H), 2.30-2.41 (m, 2H), 1.42 (s, 9H)

Step 2 tert-butyl 4-((2-(5-fluoro-1H-indol-3-yl)ethyl)amino)-2-(5-fluoropyridin-3-yl)-5,8-dihydropyrido[3,4-d]pyrimidine-7(6H)-carboxylate Prepared according to general method B, using tert-butyl 2-chloro-4-((2-(5-fluoro-1H-indol-3-yl)ethyl)amino)-5,8-dihydropyrido[3,4-d]pyrimidine-7(6H)-carboxylate (150 mg) and 5-fluoropyridine-3-boronic acid (120 mg) to give the desired product as a white solid (100 mg, 59%).

UPLC-MS (Basic Method, 2 min): rt 1.29 min, m/z 507 [M+H]<sup>+</sup>

<sup>19</sup>F NMR (400 MHz, DMSO-d<sub>6</sub>) δ ppm −125.66/−127.62 proton decoupled <sup>1</sup>H NMR (400 MHz, DMSO-d<sub>6</sub>) δ ppm 10.89-10.96 (m, 1H), 9.25-9.31 (m, 1H), 8.63-8.69 (m, 1H), 8.24-8.32 (m, 1H), 7.24-7.34 (m, 4H), 6.84-6.93 (m, 1H), 4.35-4.43 (m, 2H), 3.72-3.84 (m, 2H), 3.60-3.68 (m, 2H), 2.95-3.04 (m, 2H), 2.41-2.46 (m, 2H), 1.44 (s, 9H)

Step 3 N-(2-(5-fluoro-1H-indol-3-yl)ethyl)-2-(5-fluoropyridin-3-yl)-5,6,7,8-tetrahydropyrido[3,4-d]pyrimidin-4-amine Prepared according to general method C, using tert-butyl 4-((2-(5-fluoro-1H-indol-3-yl)ethyl)amino)-2-(5-fluoropyridin-3-yl)-5,8-dihydropyrido[3,4-d]pyrimidine-7(6H)-carboxylate (100 mg) to afford the desired product as a white solid (23 mg, 28%).

UPLC-MS (Basic Method, 4 min): rt 1.63 min, m/z 407 [M+H]<sup>+</sup>

<sup>19</sup>F NMR (400 MHz, DMSO-d<sub>6</sub>) δ ppm −125.66/−127.78 proton decoupled <sup>1</sup>H NMR (400 MHz, DMSO-d<sub>6</sub>) δ ppm 10.92 (br s, 1H), 9.28 (s, 1H), 8.64 (d, J=2.9 Hz, 1H), 8.22-8.32 (m, 1H), 7.26-7.34 (m, 3H), 7.06 (s, 1H), 6.89 (s, 1H), 3.77 (br d, J=7.0 Hz, 2H), 3.64-3.73 (m, 2H), 3.17 (d, J=5.1 Hz, 3H), 2.88-3.10 (m, 6H), 2.32 (br s, 4H)

Example 31 Preparation of N-(2-(6-fluoro-1H-indol-3-yl)ethyl)-2-(5-fluoropyridin-3-yl)-5,6,7,8-tetrahydropyrido[4,3-d]pyrimidin-4-amine

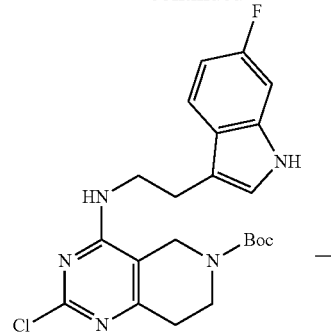

Chemical Formula: C<sub>12</sub>H<sub>15</sub>Cl<sub>2</sub>N<sub>3</sub>O<sub>2</sub>
Molecular Weight: 304.17

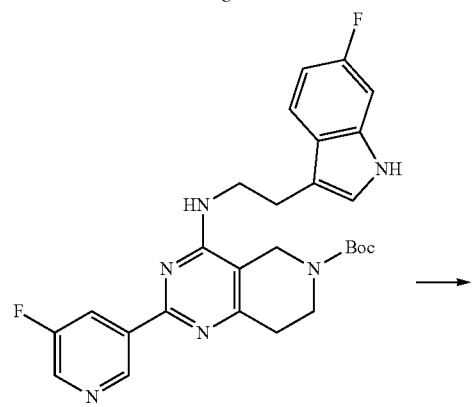

Chemical Formula: C<sub>22</sub>H<sub>25</sub>ClFN<sub>5</sub>O<sub>2</sub>
Molecular Weight: 445.92

Chemical Formula: C<sub>27</sub>H<sub>28</sub>F<sub>2</sub>N<sub>6</sub>O<sub>2</sub>
Molecular Weight: 506.58

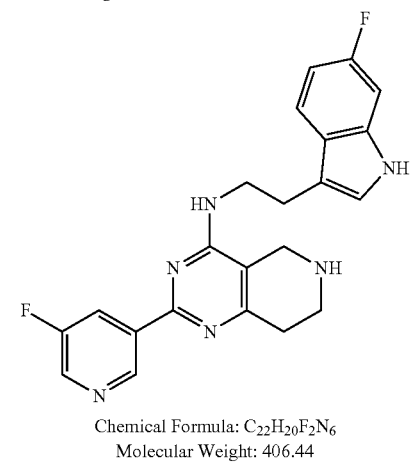

Chemical Formula: C<sub>22</sub>H<sub>20</sub>F<sub>2</sub>N<sub>6</sub>
Molecular Weight: 406.44

Step 1 tert-butyl 2-chloro-4-((2-(6-fluoro-1H-indol-3-yl)ethyl)amino)-7,8-dihydro pyrido [4,3-d]pyrimidine-6(5H)-carboxylate Prepared according to general method A, using tert-butyl 2,4-dichloro-7,8-dihydropyrido[4,3-d]pyrimidine-6(5H)-carboxylate (250 mg) and 2-(6-fluoro-1H-indol-3-yl)ethanamine hydrochloride (176 mg, 1 equiv.). Purification using Biotage (Telos 12 g, Eluent DCM/MeOH 0 to 5%) gave the desired product as a beige foam (346 mg, 94%) (Contain 10% of regioisomer).

UPLC-MS (acidic Method, 2 min): rt 1.22 min, m/z 446/448 [M+H]<sup>+</sup>

$^{19}$F NMR (400 MHz, DMSO-d$_6$) δ ppm −122.41 proton decoupled $^1$H NMR (400 MHz, DMSO-d$_6$) δ ppm 10.84-10.93 (m, 1H), 7.61-7.68 (m, 1H), 7.48-7.58 (m, 1H), 7.16-7.20 (m, 1H), 7.07-7.14 (m, 1H), 6.84 (br dd, J=2.3, 1.1 Hz, 1H), 4.16 (s, 2H), 3.52-3.64 (m, 4H), 2.88-2.98 (m, 2H), 2.55-2.65 (m, 2H), 1.43 (s, 9H)

Step 2 tert-butyl 4-((2-(6-fluoro-1H-indol-3-yl)ethyl)amino)-2-(5-fluoropyridin-3-yl)-7,8-dihydropyrido[4,3-d]pyrimidine-6(5H)-carboxylate Prepared according to general method B, using tert-butyl 2-chloro-4-((2-(6-fluoro-1H-indol-3-yl)ethyl)amino)-7,8-dihydropyrido[4,3-d]pyrimidine-6(5H)-carboxylate (160 mg) and 5-fluoropyridine-3-boronic acid (120 mg) to give the desired product as a white solid (160 mg, 88%).

UPLC-MS (Basic Method, 2 min): rt 1.30 min, m/z 507 [M+H]$^+$ $^{19}$F NMR (400 MHz, DMSO-d$_6$) δ ppm −122.48, −127.66 proton decoupled $^1$H NMR (400 MHz, DMSO-d$_6$) δ ppm 10.85-10.96 (m, 1H), 9.29 (s, 1H), 8.62-8.70 (m, 1H), 8.24-8.33 (m, 1H), 7.51-7.60 (m, 1H), 7.25-7.38 (m, 1H), 7.17-7.24 (m, 1H), 7.06-7.13 (m, 1H), 6.75-6.87 (m, 1H), 4.25 (s, 2H), 3.72-3.85 (m, 2H), 3.59-3.69 (m, 2H), 2.98-3.09 (m, 2H), 2.68-2.77 (m, 2H), 1.45 (s, 9H)

Step 3 N-(2-(6-fluoro-1H-indol-3-yl)ethyl)-2-(5-fluoropyridin-3-yl)-5,6,7,8-tetrahydropyrido[4,3-d]pyrimidin-4-amine Prepared according to general method C, using tert-butyl 4-((2-(6-fluoro-1H-indol-3-yl)ethyl)amino)-2-(5-fluoropyridin-3-yl)-7,8-dihydropyrido[4,3-d]pyrimidine-6(5H)-carboxylate (160 mg) to afford the desired product as a white solid (17 mg, 14%).

UPLC-MS (Basic Method, 4 min): rt 1.63 min, m/z 407 [M+H]$^+$ $^{19}$F NMR (400 MHz, DMSO-d$_6$) δ ppm −122.50/−127.82 proton decoupled $^1$H NMR (400 MHz, DMSO-d$_6$) δ ppm 10.89 (br s, 1H), 9.29 (s, 1H), 8.65 (d, J=2.9 Hz, 1H), 8.23-8.32 (m, 1H), 7.51-7.61 (m, 1H), 7.20 (d, J=2.0 Hz, 1H), 7.10 (dd, J=10.2, 2.3 Hz, 1H), 6.97 (t, J=5.5 Hz, 1H), 6.82 (s, 1H), 3.76 (br d, J=7.3 Hz, 2H), 3.55 (s, 2H), 2.88-3.06 (m, 5H), 2.61-2.68 (m, 2H).

Example 32 N-(2-(5-fluoro-1H-indol-3-yl)ethyl)-2-(5-fluoropyridin-3-yl)-5,6,7,8-tetrahydropyrido[4,3-d]pyrimidin-4-amine

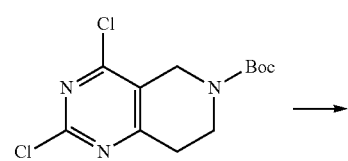

Chemical Formula: C$_{12}$H$_{15}$Cl$_2$N$_3$O$_2$
Molecular Weight: 304.17

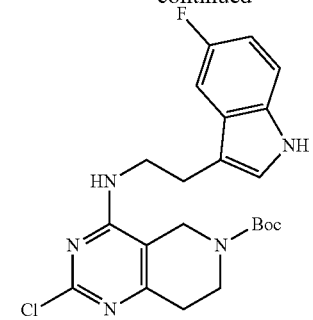

Chemical Formula: C$_{22}$H$_{25}$ClFN$_5$O$_2$
Molecular Weight: 445.92

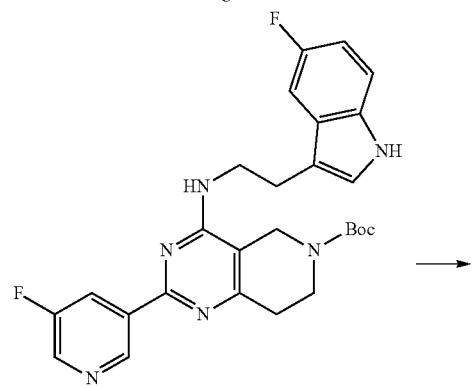

Chemical Formula: C$_{27}$H$_{28}$F$_2$N$_6$O$_2$
Molecular Weight: 506.58

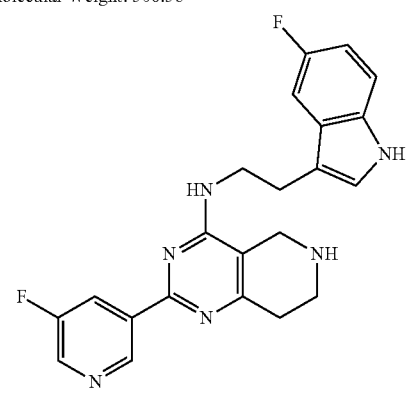

Chemical Formula: C$_{22}$H$_{20}$F$_2$N$_6$
Molecular Weight: 406.44

Step 1 tert-butyl 2-chloro-4-((2-(5-fluoro-1H-indol-3-yl)ethyl)amino)-7,8-dihydro pyrido[4,3-d]pyrimidine-6(5H)-carboxylate Prepared according to general method A, using tert-butyl 2,4-dichloro-7,8-dihydropyrido[4,3-d]pyrimidine-6(5H)-carboxylate (250 mg) and 2-(5-fluoro-1H-indol-3-yl)ethanamine hydrochloride (176 mg, 1 equiv.). Purification using Biotage (Telos 12 g, Eluent DCM/MeOH 0 to 5%) afforded the desired product as a beige foam (348 mg, 95%) (Contain 10% of regioisomer).

UPLC-MS (acidic Method, 2 min): rt 1.21 min, m/z 446/448 [M+H]$^+$ $^{19}$F NMR (400 MHz, DMSO-d$_6$) δ ppm −125.67 proton decoupled ¹H NMR (400 MHz, DMSO-d₆) δ ppm 10.88-10.96 (m, 1H), 7.48-7.63 (m, 1H), 7.39-7.46 (m, 1H), 7.30-7.35 (m, 1H), 7.26 (d, J=2.3 Hz, 1H), 6.86-6.94 (m, 1H), 4.16 (s, 2H), 3.58 (br d, J=5.9 Hz, 4H), 2.86-2.95 (m, 2H), 2.56-2.64 (m, 2H), 1.40-1.46 (m, 9H)

Step 2 tert-butyl 4-((2-(5-fluoro-1H-indol-3-yl)ethyl)amino)-2-(5-fluoropyridin-3-yl)-7,8-dihydropyrido[4,3-d]pyrimidine-6(5H)-carboxylate Prepared according to general method B, using tert-butyl 2-chloro-4-((2-(5-fluoro-1H-indol-3-yl)ethyl)amino)-7,8-dihydropyrido[4,3-d]pyrimidine-6(5H)-carboxylate (160 mg) and 5-fluoropyridine-3-boronic acid (120 mg) to give the desired product as a white solid (150 mg, 82%).

UPLC-MS (Basic Method, 2 min): rt 1.29 min, m/z 507 [M+H]⁺

¹⁹F NMR (400 MHz, DMSO-d₆) δ ppm −125.64, −127.61 proton decoupled

¹H NMR (400 MHz, DMSO-d₆) δ ppm 10.89-10.97 (m, 1H), 9.26-9.32 (m, 1H), 8.63-8.68 (m, 1H), 8.24-8.32 (m, 1H), 7.22-7.36 (m, 4H), 6.83-6.94 (m, 1H), 4.19-4.30 (m, 2H), 3.72-3.84 (m, 2H), 3.58-3.69 (m, 2H), 2.97-3.05 (m, 2H), 2.69-2.78 (m, 2H), 1.45 (s, 9H)

Step 3 N-(2-(5-fluoro-1H-indol-3-yl)ethyl)-2-(5-fluoropyridin-3-yl)-5,6,7,8-tetrahydropyrido[4,3-d]pyrimidin-4-amine Prepared according to general method C, using tert-butyl 4-((2-(5-fluoro-1H-indol-3-yl)ethyl)amino)-2-(5-fluoropyridin-3-yl)-7,8-dihydropyrido[4,3-d]pyrimidine-6(5H)-carboxylate (150 mg) to afford the desired product as a white solid (11 mg, 9%).

UPLC-MS (Basic Method, 4 min): rt 1.61 min, m/z 407 [M+H]⁺

¹⁹F NMR (400 MHz, DMSO-d₆) δ ppm −125.66/-127.78 proton decoupled

¹H NMR (400 MHz, DMSO-d₆) δ ppm 10.92 (br s, 1H), 9.29 (t, J=1.6 Hz, 1H), 8.64 (d, J=2.9 Hz, 1H), 8.23-8.33 (m, 1H), 7.23-7.35 (m, 3H), 6.83-6.98 (m, 2H), 3.75 (br d, J=7.7 Hz, 2H), 3.55 (s, 2H), 2.87-3.08 (m, 6H), 2.57-2.68 (m, 3H)

Examples were tested in selected biological assays two or more times. Data are reported as the arithmetic mean of the pIC$_{50}$ (−log$_{10}$IC$_{50}$) values, where IC$_{50}$ is defined as the concentration of compound producing a 50% inhibition of the agonist (KYNA) response.

The in vitro activity of the compounds of the present invention was assessed in the following assays:

In Vitro Assay 1: AhR Antagonism in U937 Cells (Promega P450-Glo™ Assay)

AhR antagonism was assessed in U937 cells (myeloid lineage cell line derived from a human histiocytic lymphoma).). Ligand binds the AhR in the cytoplasm, and the AhR-ligand complex translocates to the nucleus and forms a heterodimer with AhR nuclear translocator (Arnt). This complex binds the xenobiotic response element (XRE) in the 5' upstream region of the CYP1A1 promoter, enhancing CYP1A1 expression. CYP1A1 activity is subsequently determined by assessing the conversion of Luciferin-CEE to luciferin, which in turn reacts with luciferase to produce light. The amount of light produced is directly proportional to cytochrome P450 activity. U937 cells in Ultraculture serum free media (Lonza) were plated at 100,000 cells per well in a round bottom 96 well tissue culture plate. Seven concentrations of test compound (final [DMSO] 1%) were added and incubated for 10 minutes before the addition of 300M KYNA. The plates were then placed in an incubator at 37° C., >85% humidity, 5% CO₂ for 24 hrs. After aspiration of the supernatant the CYP1A1 substrate Luciferin-CEE ([Final] 83 µM) was added and incubated for 3 hrs before the reaction was stopped by adding luciferin detection reagent and luminescence was read after 20 minutes.

In Vitro Assay 22: CYP7A Inhibition Assay

The direct CYP1A1 inhibitory activity of test compounds was also assessed using the Promega P450-Glo™ assay system. Seven concentrations of test compound were added to a ½ area white 96 well plate. Cypex CYP6A. bactosomes ([final] 0.5 pmol) and CYPA substrate Luciferin-CEE ([final] 30 µM) were prepared in 0.1M potassium phosphate buffer and incubated with test compounds at 37° C. for 5 minutes. 0.2m NADPH was then added to the plates and incubated at 37° C., for 10 minutes. The reaction was stopped by adding luciferin detection reagent and luminescence was read after 20 minutes.

Results

| Example no. | U937 pIC50 | cyp1A1 pIC50 |
| --- | --- | --- |
| 1 | 8.80 | 6.00 |
| 2 | 8.90 | 6.20 |
| 3 | 8.20 | 6.80 |
| 4 | 8.20 | 6.10 |
| 5 | 8.00 | 6.40 |
| 6 | 8.30 | 6.50 |
| 7 | 8.00 | 6.70 |
| 8 | 7.80 | 7.00 |
| 9 | 7.70 | 6.60 |
| 10 | 7.90 | 6.80 |
| 11 | 8.50 | 6.40 |
| 12 | 9.00 | 6.10 |
| 13 | 8.50 | 5.70 |
| 14 | 8.90 | 6.10 |
| 15 | 8.70 | 6.00 |
| 16 | 8.20 | 7.00 |
| 17a | 7.60 | 6.20 |
| 17b | 7.80 | 6.10 |
| 18a | 8.30 | 6.20 |
| 18b | 7.70 | 5.90 |
| 19 | 5.50 | 5.10 |
| 20 | 7.60 | 6.40 |
| 21 | 7.70 | 6.40 |
| 22 | 8.00 | 6.50 |
| 23 | 8.00 | 6.70 |
| 24 | 7.90 | 6.60 |
| 25 | 8.30 | 6.20 |
| 26 | 8.21 | 7.2 |
| 27 | 8.35 | 7.2 |
| 28 | <5.0 | 5.5 |
| 29 | 8.10 | 6.7 |
| 30 | 7.58 | 6.5 |
| 31 | 8.29 | 7.2 |
| 32 | 8.22 | 7.1 |

The invention claimed is:

1. A compound of formula (I)

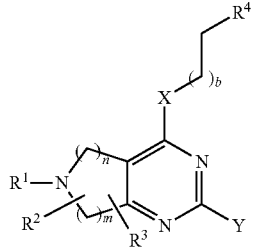

(I)

wherein:

Y is a 5 or 6 membered aromatic ring optionally containing 1, 2, or 3 heteroatoms selected from N, O and S, substituted with $R^5$ and $R^6$;

$R^1$ is H, $C_{1-3}$ alkyl, $(-CH_2)$ pCN, $-COC_{1-3}$ alkyl, $-CO(CH_2)$ $qNR^7R^8$, $-SO_2C_{1-3}$ alkyl, $-SO_2NR^7R^8$, $-(CH_2)qPh$, or $-C(O)Z$;

$R^2$ is H or $C_{1-3}$ alkyl;

$R^3$ is H or $C_{1-3}$ alkyl;

$R^4$ is a 9 or 10 membered heteroaryl bearing substituents $R^9$ and $R^{10}$, wherein said heteroaryl haswith at least one heteroatom selected from N, O or S—;

$R^5$ is H, hydroxy, halogen, CN, a $C_{1-3}$ alkyl group, $-CO(CH_2)$ qNR7R8,-SO2C1-3 alkyl, or-SO2 NR7R8;

$R^6$ is hydroxy, halogen, CN, a C1-3 alkyl group,-CO(CH2)qNR$^7$R$^8$, $-SO_2$C1-3 alkyl, or-SO2 NR$^7$R$^8$;

$R^7$ is H or $C_{1-3}$ alkyl;

$R^8$ is H or $C_{1-3}$ alkyl;

$R^9$ is H, hydroxy, halogen, CN, a $C_{1-3}$ alkyl group, $-CO(CH_2)q$ $NR^7R^8$, $-SO_2C_{1-3}$ alkyl, or $-SO_2NR^7R^8$, $R^{10}$ is H, hydroxy, halogen, CN, a $C_{1-3}$ alkyl group, $-CO(CH_2)q$ $NR^7R^8$, $-SO_2C_{1-3}$ alkyl, or $-SO_2NR^7R^8$;

$R^{11}$ is H or $C_{1-3}$ alkyl;

X is $NR^{11}$;

Z is a 5 or 6 membered heteroaryl with at least one heteroatom selected from N, O and S, optionally bearing one or two substituents selected from hydroxy, halogen, CN, or C1-3 alkyl;

b is an integer 1 or 2;

p is an integer 1, 2 or 3;

q is 0, 1, 2 or 3 wherein:

n is 2 and m is 1, or n is 1 and m is 2, or a pharmaceutically acceptable salt thereof.

2. A compound of formula (II)

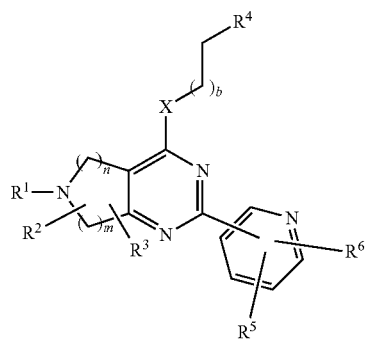

(II)

wherein X, $R^1$, $R^2$, $R^3$, $R^4$, $R^5$, $R^6$, b, are defined above for compounds of formula (I), and n is 2 and m is 1, or n is 1 and m is 2, or a pharmaceutically acceptable salt thereof.

3. A compound according to claim 1, of formula (IV):

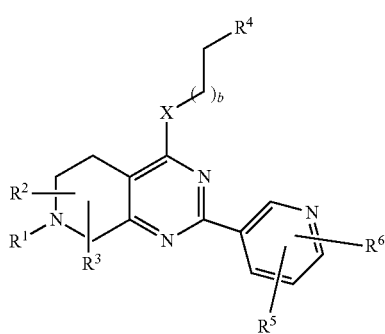

(IV)

or a pharmaceutically acceptable salt thereof, wherein X, $R^1$, $R^2$, $R^3$, $R^4$, $R^5$, $R^6$, and b are defined above for compounds of formula (I).

4. A compound according to claim 1, of formula (V):

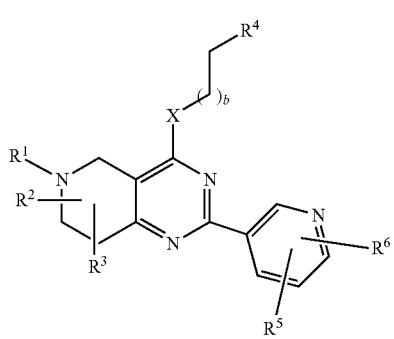

(V)

or a pharmaceutically acceptable salt thereof, wherein X, $R^1$, $R^2$, $R^3$, $R^4$, $R^5$, $R^6$, and b are defined above for compounds of formula (I).

5. A compound according to claim 1, wherein $R^1$ is independently selected from H, $CH^3$, $-CH_2CH_3$, $-CH_2CH_2CH_3$, $-CH(CH_3)_2$, $-C(O)NH_2$, $-C(O)$ NHCH$_3$, —C(O)N(CH$_3$)$_2$, —CH$_2$CN, —SO$_2$NH$_2$, —SO$_2$CH$_3$, —SO$_2$N(CH$_3$)$_2$, —CH$_2$Ph, and —C(O)1-Me-Pyrazol-5-yl.

6. A compound according to claim 5, wherein R$^1$ is selected from H, —CH$_2$CN, —SO$_2$CH$_3$, —SO$_2$N(CH$_3$)$_2$, and —C(O)N(CH$_3$)$_2$.

7. A compound according to claim 1, wherein R$^2$ is H or —CH$_3$.

8. A compound according to claim 7, wherein R$^2$ is H.

9. A compound according to claim 1, wherein R$^3$ is H or —CH$_3$.

10. A compound according to claim 1, wherein R$^4$ is selected from indolyl and benzimidazolyl.

11. A compound according to claim 1, wherein R$^5$ is selected from H, Fl, Cl, CN and —CH$_3$.

12. A compound according to claim 1, wherein R$^6$ is H, Fl, Cl, CN or —CH$_3$.

13. A compound according to claim 1, wherein R$^7$ is selected from H and —CH$^3$.

14. A compound according to claim 13, wherein R$^7$ is —CH$_3$.

15. A compound according to claim 1, wherein R$^8$ is selected from H and —CH$_3$.

16. A compound according to claim 15, wherein R$^8$ is H.

17. A compound according to claim 1, wherein R$^{11}$ is H.

18. A pharmaceutical composition comprising a compound according to claim 1 and an excipient, diluent or carrier.

19. A compound according to claim 1, wherein the compound is selected from: 1-(4-((2-(1H-indol-3-yl) ethyl) amino)-2-(5-fluoropyridin-3-yl)-5,8-dihydropyrido[3,4-d]pyrimidin-7 (6H)-yl)ethan-1-one;
- N-(2-(1H-indol-3-yl)ethyl)-2-(5-fluoropyridin-3-yl)-7-(methyl sulfonyl)-5,6,7,8-tetrahydropyrido[3,4-d]pyrimidin-4-amine;
- 5-(4-((2-(1H-indol-3-yl)ethyl)amino)-7-(cyanomethyl)-5,6,7,8-tetrahydropyrido [3,4-d]pyrimidin-2-yl) nicotinonitrile;
- 2-(4-((2-(1H-indol-3-yl) ethyl)amino)-2-(5-fluoropyridin-3-yl)-5,8-dihydropyrido [3,4-d]pyrimidin-7 (6H)-yl) acetonitrile;
- N-(2-(1H-indol-3-yl) ethyl)-2-(5-fluoropyridin-3-yl)-7-isopropyl-5,6,7,8-tetra hydropyrido[3,4-d]pyrimidin-4-amine;
- N-(2-(1H-indol-3-yl) ethyl)-2-(5-fluoropyridin-3-yl)-7-methyl-5,6,7,8-tetrahydropyrido [3,4-d]pyrimidin-4-amine;
- 4-((2-(1H-indol-3-yl)ethyl)amino)-2-(5-fluoropyridin-3-yl) -N,N-dimethyl-5,8-dihydropyrido[3,4-d]pyrimidine-7 (6H)-sulfonamide;
- 4-((2-(1H-indol-3-yl)ethyl)amino)-2-(5-fluoropyridin-3-yl) -N,N-dimethyl-5,8-dihydropyrido [3,4-d]pyrimidine-7 (6H)-carboxamide;
- 4-((2-(1H-indol-3-yl)ethyl)amino)-2-(5-fluoropyridin-3-yl) -N-methyl-5,8-dihydropyrido [3,4-d]pyrimidine-7 (6H)-carboxamide;
- 4-((2-(1H-indol-3-yl)ethyl)amino)-2-(5-fluoropyridin-3-yl) -5,8-dihydropyrido [3,4-d]pyrimidin-7 (6H)-yl) (1-methyl-1H-pyrazol-5-yl)methanone;
- 1-(4-((2-(1H-indol-3-yl)ethyl)amino)-2-(5-fluoropyridin-3-yl)-5,8-dihydropyrido [3,4-d]pyrimidin-7 (6H)-yl)-2-aminoethan-1-one;
- N-(2-(1H-indol-3-yl)ethyl)-7-benzyl-2-(5-fluoropyridin-3-yl)-8,8-dimethyl-5,6,7,8-tetrahydropyrido[3,4-d] pyrimidin-4-amine;
- N-(2-(1H-indol-3-yl) ethyl)-2-(5-fluoropyridin-3-yl)-8,8-dimethyl-5,6,7,8-tetrahydropyrido[3,4-d]pyrimidin-4-amine;
- N-(2-(1H-benzo [d]imidazol-2-yl) ethyl)-2-(5-fluoropyridin-3-yl)-5,6,7,8-tetrahydropyrido[3,4-d]pyrimidin-4-amine;
- N-(2-(1H-indol-3-yl)ethyl)-2-(5-methylpyridin-3-yl)-5,6,7,8-tetrahydropyrido[3,4-d]pyrimidin-4-amine;
- N-(2-(1H-indol-3-yl)ethyl)-2-(5-fluoropyridin-3-yl)-5,6,7,8-tetrahydropyrido[4,3-d]pyrimidin-4-amine;
- N-(2-(1H-indol-3-yl)ethyl)-2-(5-chloropyridin-3-yl)-5,6,7,8-tetrahydropyrido[3,4-d]pyrimidin-4-amine;
- 5-(4-((2-(1H-indol-3-yl) ethyl) amino)-5,6,7,8-tetrahydro pyrido [3,4-d]pyrimidin-2-yl) nicotinonitrile;
- N-(2-(1H-indol-3-yl)ethyl)-2-(5-methylpyridin-3-yl)-5,6,7,8-tetrahydro pyrido [4,3-d]pyrimidin-4-amine;
- N-(2-(1H-indol-3-yl)ethyl)-2-(5-chloropyridin-3-yl)-5,6,7,8-tetrahydropyrido [4,3-d]pyrimidin-4-amine;
- N-(2-(1H-benzo [d]imidazol-2-yl) ethyl)-2-(5-fluoropyridin-3-yl)-5,6,7,8-tetrahydropyrido [4,3-d]pyrimidin-4-amine;
- N-(2-(6-fluoro-1H-indol-3-yl) ethyl)-2-(5-fluoropyridin-3-yl)-5,6,7,8-tetrahydropyrido[3,4-d] pyrimidin-4-amine;
- N-(2-(5-fluoro-1H-indol-3-yl) ethyl)-2-(5-fluoropyridin-3-yl)-5,6,7,8-tetrahydropyrido[3,4-d]pyrimidin-4-amine;
- N-(2-(6-fluoro-1H-indol-3-yl) ethyl)-2-(5-fluoropyridin-3-yl)-5,6,7,8-tetrahydropyrido[4,3-d]pyrimidin-4-amine;
- N-(2-(5-fluoro-1H-indol-3-yl) ethyl)-2-(5-fluoropyridin-3-yl)-5,6,7,8-tetrahydropyrido [4,3-d]pyrimidin-4-amine.

20. A compound according to claim 1, wherein the compound is N-(2-(1H-indol-3-yl)ethyl)-2-(5-fluoropyridin-3-yl)-5,6,7,8-tetrahydropyrido [3,4-d]pyrimidin-4-amine.

* * * * *